US012799201B2

(12) United States Patent
Wang et al.

(10) Patent No.: US 12,799,201 B2
(45) Date of Patent: Nov. 17, 2026

(54) ANTI-CD22 NANO ANTIBODY AND USE THEREOF

(71) Applicant: SIMCERE ZAIMING PHARMACEUTICAL CO., LTD., Hainan (CN)

(72) Inventors: Qiong Wang, Shanghai (CN); Cuiqing Yang, Shanghai (CN); Zhuoxiao Cao, Shanghai (CN); Renhong Tang, Shanghai (CN); Jinsheng Ren, Nanjing (CN)

(73) Assignee: Simcere Zaiming Pharmaceutical Co., Ltd., Hainani (CN)

( * ) Notice: Subject to any disclaimer, the term of this patent is extended or adjusted under 35 U.S.C. 154(b) by 662 days.

(21) Appl. No.: 18/265,150

(22) PCT Filed: Dec. 2, 2021

(86) PCT No.: PCT/CN2021/135058

§ 371 (c)(1),
(2) Date: Jun. 2, 2023

(87) PCT Pub. No.: WO2022/117032

PCT Pub. Date: Jun. 9, 2022

(65) Prior Publication Data

US 2023/0416360 A1 Dec. 28, 2023

(30) Foreign Application Priority Data

Dec. 3, 2020 (CN) ......................... 202011395861.6

(51) Int. Cl.
*C07K 16/28* (2006.01)
*A61K 40/42* (2025.01)

(52) U.S. Cl.
CPC ...... *C07K 16/2803* (2013.01); *A61K 40/4212* (2025.01); *C07K 2317/22* (2013.01); *C07K 2317/33* (2013.01); *C07K 2317/569* (2013.01); *C07K 2317/92* (2013.01)

(58) Field of Classification Search
None
See application file for complete search history.

(56) References Cited

U.S. PATENT DOCUMENTS

2010/0143368 A1 6/2010 King et al.

FOREIGN PATENT DOCUMENTS

| | | |
|---|---|---|
| CN | 109970858 | 7/2019 |
| CN | 111100207 A | 5/2020 |
| CN | 111217908 | 6/2020 |
| CN | 111518217 | 8/2020 |
| WO | WO 2020053634 | 3/2020 |

OTHER PUBLICATIONS

Konning et al., Curr. Opin. Structural Biol. 45:10-16, 2017 (Year: 2017).*
Rabia et al., Biochem Eng J. Jun. 5, 2018;137:365-374, (Year: 2018).*
Faraji et al., “Functional Study of a Camelid Single Domain Anti-CD22 Antibody,” International Journal of Peptide Research and Therapeutics, Jun. 2019, 26:633-639, 7 pages.
International Search Report and Written Opinion in International Appln. No. PCT/CN2021/135058, mailed on Mar. 7, 2022, 19 pages (with English translation).
Wu et al., “Construction and Characterization of a Non-Immune Llama Variable Heavy Chain Phage Display Antibody Library” Current Immunology, Sep. 2011, 31(5):353-357, 6 pages (with English abstract).
Faraji et al., “Development and characterization of a camelid single-domain antibody directed to human CD22 biomarker,” Biotechnology and Applied Biochemistry, Mar. 2018, 65(5):718-725.

* cited by examiner

*Primary Examiner* — Daniel C Gamett
(74) *Attorney, Agent, or Firm* — Fish & Richardson P.C.

(57) ABSTRACT

Provided are an CD22 nano antibody, and a preparation method therefor and an application thereof. The CD22 nano antibody has high affinity with a CD22 protein, and can be used for preparing drugs for treating tumors, autoimmune diseases, etc.

22 Claims, 16 Drawing Sheets

Specification includes a Sequence Listing.

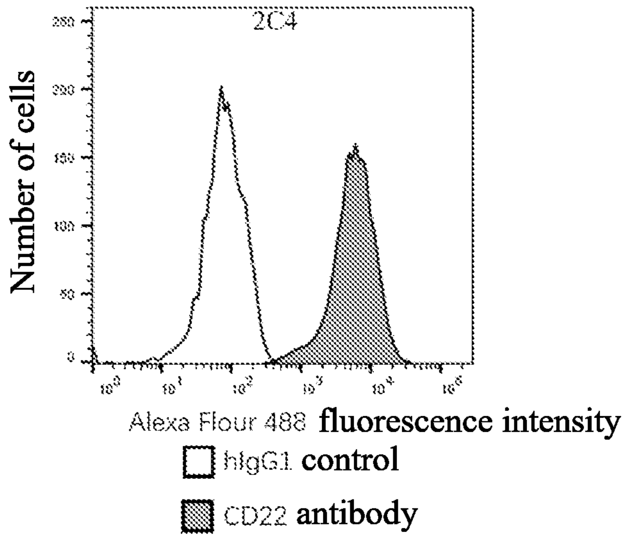
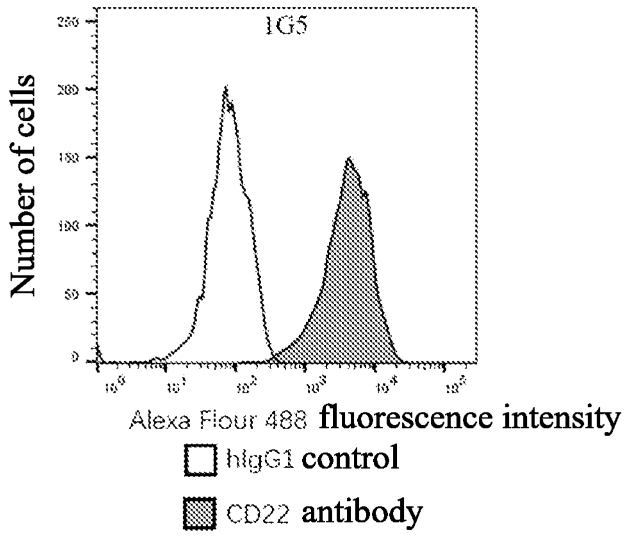
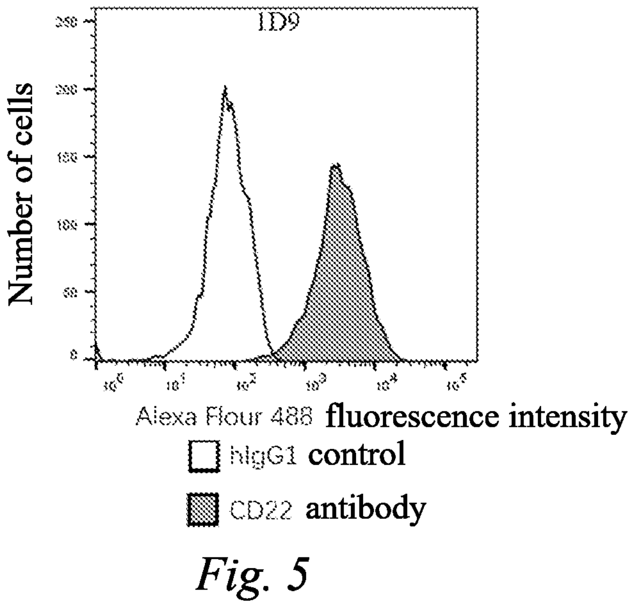
*Fig. 5*

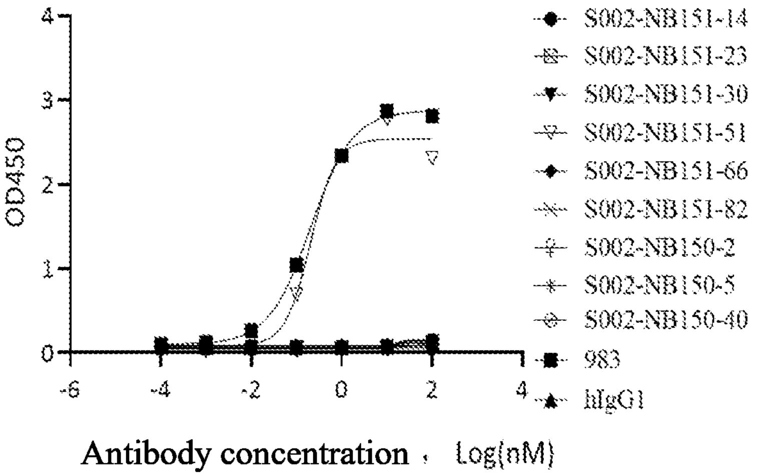
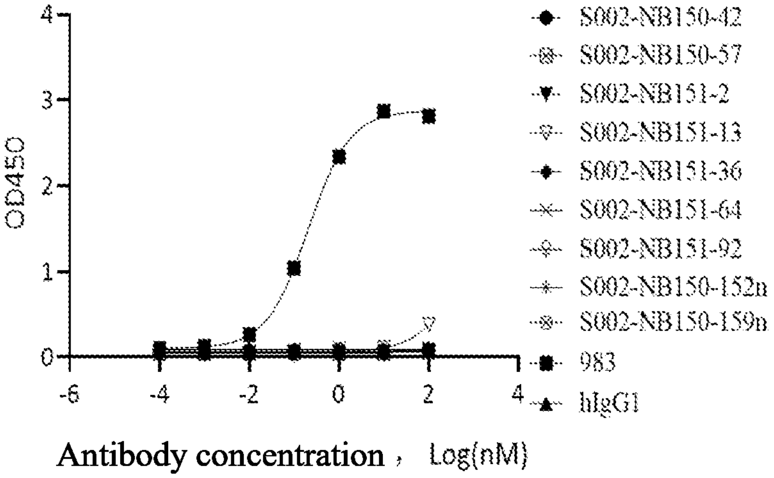
*Fig. 8*

| Designation of antibody | EC80 (μg/mL) | soluble 25μg/mL / cotiang 2μg/mL | S002-NB151-23 | HA22 | S002-NB151-64 | S002-NB151-66 | S002-NB150-2 | S002-NB150-5 | S002-NB150-40 | S002-NB150-42 | S002-NB150-57 | S002-NB150-152n | hL22 | S002-NB151-82 | S002-NB151-36 | S002-NB151-14 | S002-NB151-2 | S002-NB151-92 | S002-NB150-159n | S002-NB151-30 | S002-NB151-51 | S002-NB151-13 | m971 |
|---|---|---|---|---|---|---|---|---|---|---|---|---|---|---|---|---|---|---|---|---|---|---|---|
| S002-NB151-23 | 0.24 | S002-NB151-23 | 92% | 91% | 87% | 91% | 83% | 89% | 95% | 84% | 96% | 96% | 79% | -21% | -104% | -80% | -43% | -35% | -8% | -79% | -89% | -95% | -36% |
| HA22 | 0.06 | HA22 | 21% | 29% | 25% | 43% | 17% | 28% | 39% | 31% | 41% | 49% | 37% | -1% | -3% | -16% | 8% | -25% | 21% | -9% | -3% | -11% | -5% |
| S002-NB151-64 | 1.32 | S002-NB151-64 | 84% | 87% | 93% | 83% | 74% | 89% | 78% | 86% | 89% | 90% | 49% | 9% | -98% | -81% | -39% | -3% | -174% | -99% | -111% | -74% | -270% |
| S002-NB151-66 | 0.21 | S002-NB151-66 | 81% | 104% | 93% | 65% | 84% | 86% | 86% | 76% | 85% | 86% | 89% | 60% | 5% | 13% | 26% | 21% | 33% | -1% | 1% | -4% | -3% |
| S002-NB150-2 | 0.13 | S002-NB150-2 | 34% | 102% | 84% | 79% | 82% | 85% | 64% | 71% | 72% | 69% | 56% | 30% | -63% | -63% | 11% | -13% | 23% | -55% | -82% | -31% | -57% |
| S002-NB150-5 | 0.28 | S002-NB150-5 | 94% | 104% | 95% | 89% | 93% | 97% | 97% | 92% | 89% | 91% | 80% | -13% | -63% | -43% | -38% | -18% | -103% | -66% | -31% | -47% | -154% |
| S002-NB150-40 | 0.18 | S002-NB150-40 | 79% | 94% | 92% | 80% | 77% | 80% | 83% | 83% | 72% | 81% | 69% | 7% | -24% | -36% | 4% | -9% | 8% | -24% | -48% | -12% | -10% |
| S002-NB150-42 | 0.17 | S002-NB150-42 | 77% | 91% | 93% | 88% | 88% | 87% | 85% | 81% | 82% | 82% | 50% | 8% | -29% | -88% | -44% | -12% | 9% | -85% | -71% | -54% | -9% |
| S002-NB150-57 | 0.12 | S002-NB150-57 | 85% | 95% | 95% | 93% | 92% | 88% | 89% | 84% | 89% | 90% | 66% | -6% | -80% | -44% | -7% | -5% | 1% | -56% | -56% | -18% | -18% |
| S002-NB150-152n | 0.30 | S002-NB150-152n | 91% | 97% | 98% | 95% | 95% | 100% | 87% | 94% | 95% | 94% | 63% | 2% | -62% | -60% | -7% | -34% | 5% | -65% | -50% | -30% | -29% |
| hL22 | 0.07 | hLL2 | 57% | 77% | 57% | 54% | 50% | 56% | 68% | 46% | 63% | 75% | 62% | 41% | 3% | -3% | 7% | -6% | 43% | 9% | 14% | 11% | -8% |
| S002-NB151-82 | 0.30 | S002-NB151-82 | -83% | -5% | -74% | -51% | -29% | -44% | -33% | -40% | -35% | -40% | -41% | 96% | 93% | 0% | -52% | -46% | -22% | -99% | -102% | -84% | -110% |
| S002-NB151-36 | 0.83 | S002-NB151-36 | -18% | -45% | -16% | -16% | -33% | -34% | -47% | -35% | -39% | -38% | -26% | 89% | 85% | 74% | 5% | -31% | 11% | -19% | -15% | -37% | -8% |
| S002-NB151-14 | 2.42 | S002-NB151-14 | -47% | -20% | -63% | -49% | -15% | -30% | -26% | -20% | -23% | -28% | -14% | 61% | 9% | 25% | -27% | -8% | 19% | -63% | -59% | -50% | 16% |
| S002-NB151-2 | 1.56 | S002-NB151-2 | -88% | -270% | -99% | -68% | -194% | -159% | -141% | -144% | -156% | -117% | -114% | -75% | -36% | -32% | 41% | 26% | 13% | -64% | -135% | -159% | -16% |
| S002-NB151-92 | 1.17 | S002-NB151-92 | -210% | -150% | -179% | -132% | -62% | -73% | -60% | -52% | -65% | -57% | -89% | 26% | -146% | -120% | 68% | 49% | 91% | -210% | -213% | -189% | 26% |
| S002-NB150-159n | 0.43 | S002-NB150-159n | -170% | -320% | -129% | -124% | -157% | -162% | -151% | -122% | -147% | -140% | -267% | -71% | -96% | -28% | 52% | -9% | 49% | -175% | -125% | -232% | -25% |
| S002-NB151-30 | 0.61 | S002-NB151-30 | -49% | -58% | -65% | -51% | -63% | -72% | -78% | -75% | -78% | 22% | -52% | -5% | -45% | -58% | 14% | -30% | 22% | 70% | 50% | -33% | -35% |
| S002-NB151-51 | 0.12 | S002-NB151-51 | 9% | -3% | -27% | 13% | -18% | -14% | -21% | -8% | -14% | -4% | 11% | -48% | -8% | 1% | 3% | -6% | 8% | 59% | 37% | 7% | -24% |
| S002-NB151-13 | 6.01 | S002-NB151-13 | -10% | -4% | -17% | -16% | 13% | 10% | 10% | 6% | 0% | -27% | -27% | 51% | -18% | -12% | 34% | 29% | 44% | -7% | -8% | 62% | -19% |
| m971 | 0.16 | m971 | -41% | -15% | -48% | -35% | -18% | -21% | -17% | -22% | -23% | -32% | -20% | -6% | -28% | -23% | 24% | 11% | 23% | -17% | -26% | -32% | 93% |

*Fig. 13*

ANTI-CD22 NANO ANTIBODY AND USE THEREOF

CROSS-REFERENCE TO RELATED APPLICATIONS

The present disclosure application is a U.S. national phase application under 35 U.S.C. § 371 of International Patent Application No. PCT/CN2021/135058 filed Dec. 2, 2021, which claims the right of priority of Chinese patent application no. 202011395861.6 titled "ANTI-CD22 NANO ANTIBODY AND USE THEREOF" and filed with the China Patent Office on Dec. 3, 2020, which is incorporated in the present disclosure by reference in its entirety.

SEQUENCE LISTING

This application contains a Sequence Listing that has been submitted electronically as an ASCII text file named "54736-0004US1_SL_ST25.txt." The ASCII text file, created on May 31, 2023, is 108,652 bytes in size. The material in the ASCII text file is hereby incorporated by reference in its entirety.

TECHNICAL FIELD

The present invention relates to the fields of bioengineering and biomedicine, and mainly relates to an anti-human CD22 nano body or an antigen-binding fragment thereof, and an encoding nucleic acid, an expression vector and an expression cell, a preparation method, a pharmaceutical composition therefor, and their use for treating diseases, such as use for treating tumors and autoimmune diseases.

BACKGROUND ART

CD22 is a type I transmembrane glycoprotein, which belongs to the sialic acid-binding immunoglobulin like lectins (Siglec) family. As a B cell differentiation antigen, it is specifically expressed in B cells. The expression of CD22 begins from the pre-B cell (pre-B cell) stage, and stops after B cells differentiate into plasma cells. The broad-spectrum expression of CD22 in B cell development makes it an attractive molecule for targeting B cells.

The extracellular region of CD22 consists of 7 Ig-like domains and 12 predicted N-linked glycosylation sites, and its N-terminal (i.e., distal end of membrane) domain 1 is V Type Ig-like domain, which, as a ligand binding site, can recognize $\alpha$2,6-coupled sialic acid. The intracellular region of CD22 has immunoreceptor tyrosine-based inhibitory motifs (ITIMs). When the tyrosine on the ITIMs is phosphorylated by the Src family protein kinase, binding sites for molecules containing SH2 (Src homology2) domain would be generated, then SHP-1 (Src homology region 2 domain-containing phosphatase-1) was recruited to inhibit the BCR (B-cell receptor) signaling pathway of normal B cells.

$\alpha$2,6-coupled sialoglycoprotein exists in hematopoietic cells, some endothelial cells, T cells and B cells, and CD22 protein itself also produces $\alpha$2,6-coupled sialic acid, so CD22 can form cis-interaction with itself and other sialoglycoproteins on the surface of B cells, and trans-interaction with sialoglycoproteins on the surface of other types of cells. In resting B cells, the cis-interaction between CD22 molecules makes the ligand-binding site of CD22 masked, but once the ligand is presented by an adjacent cell, the masked ligand-binding site of CD22 is exposed and interacts with the ligand of the adjacent cells to form trans-interaction. The cis-interaction between CD22 molecules forms homo-oligomers on the B cell surface and the homo-oligomers can form a dynamic nanocluster and generate an antigen binding signal threshold that must be reached before B cell activation, thereby regulating B cell signaling pathway.

CD22 is expressed in 60% to 90% of B cell malignancies and is not expressed in hematopoietic stem cells. In an early clinical study on acute lymphoblastic leukemia (ALL), CD22 is expressed in 60% to 85% of ALL. In another study, the positive rate of CD22 in B-lineage ALL patients reaches 93%. CD22 is expressed in more than 85% of patients with diffuse large B-cell lymphomas (DLBCLs). There are many clinical trials investigating the effectiveness of drugs that target CD22. Epratuzumab is a CD22 monoclonal antibody that has certain effects in adults and children with B-ALL. CD22 antibody-conjugated drugs have a certain therapeutic effect on B-ALL.

Nano antibody (Nanobody, Nb) is a genetically engineered antibody containing only a single domain. In 1993, Belgian scientist Hamers-Casterman C discovered a natural heavy chain antibody in camel blood that only contained heavy chains but no light chains. Compared with a normal antibody, the heavy chain antibody has no light chains, but still retains the ability to bind to an antigen. After cloning the variable region of the heavy chain antibody in camels, the obtained single domain antibody (sdAb) consisting of only one heavy chain variable region is called nanobody or VHH antibody (variable heavy chain domain of a heavy chain antibody). The nanobody not only has a molecular weight which is only 1/10 of that of a normal antibody, but also has more flexible chemical properties, good stability, high solubility, and high tumor tissue penetration, and is easily expressed and easily coupled to other molecules. Therefore, the nanobody technology has broad prospects of application in development of a therapeutic antibody against CD22.

SUMMARY OF THE INVENTION

The present invention provides a nanobody or an antigen-binding fragment that specifically binds to CD22, a nucleic acid encoding the antibody and the antigen-binding fragment, a pharmaceutical composition and a kit comprising the antibody and the antigen-binding fragment, and they can be used in the preparation of drugs for treating tumors, autoimmune diseases, etc.

In some embodiments, the nanobody or the antigen-binding fragment that specifically binds CD22, the nanobody or the antigen-binding fragment comprises a combination of CDRs, the combination of CDRs comprises: CDR1, CDR2, and CDR3; the CDR1, CDR2 and CDR3 have any sequence combination selected from the following, or a sequence combination with 1, 2, 3 or more amino acid insertions, deletions and/or substitutions compared to the sequence combination:

| | SEQ ID NO. | | |
|---|---|---|---|
| No. | CDR1 | CDR2 | CDR3 |
| VH1 | SEQ ID NO. 57 | SEQ ID NO. 58 | SEQ ID NO. 59 |
| VH2 | SEQ ID NO. 60 | SEQ ID NO. 61 | SEQ ID NO. 62 |
| VH3 | SEQ ID NO. 63 | SEQ ID NO. 64 | SEQ ID NO. 65 |
| VH4 | SBQ ID NO. 66 | SEQ ID NO. 67 | SEQ ID NO. 68 |
| VHS | SBQ ID NO. 69 | SEQ ID NO. 70 | SEQ ID NO. 71 |
| VH6 | SEQ ID NO. 72 | SEQ ID NO. 73 | SEQ ID NO. 74 |
| VH7 | SEQ ID NO. 75 | SEQ ID NO. 76 | SEQ ID NO. 77 |
| VH8 | SEQ ID NO. 78 | SEQ ID NO. 79 | SEQ ID NO. 80 |

-continued

| | SEQ ID NO. | | |
|---|---|---|---|
| No. | CDR1 | CDR2 | CDR3 |
| VH9 | SEQ ID NO. 81 | SEQ ID NO. 82 | SEQ ID NO. 83 |
| VH10 | SEQ ID NO. 84 | SEQ ID NO. 85 | SEQ ID NO. 86 |
| VH11 | SEQ ID NO. 87 | SEQ ID NO. 88 | SEQ ID NO. 89 |
| VH12 | SEQ ID NO. 90 | SEQ ID NO. 91 | SEQ ID NO. 92 |
| VH13 | SEQ ID NO. 93 | SEQ ID NO. 94 | SEQ ID NO. 95 |
| VH14 | SEQ ID NO. 96 | SEQ ID NO. 97 | SEQ ID NO. 98 |
| VH15 | SEQ ID NO. 99 | SEQ ID NO. 100 | SEQ ID NO. 101 |
| VH16 | SEQ ID NO. 102 | SEQ ID NO. 103 | SEQ ID NO. 104 |
| VH17 | SEQ ID NO. 105 | SEQ ID NO. 106 | SEQ ID NO. 107 |
| VH18 | SEQ ID NO. 108 | SEQ ID NO. 109 | SEQ ID NO. 110 |
| VH19 | SEQ ID NO. 111 | SEQ ID NO. 112 | SEQ ID NO. 113 |
| VH20 | SEQ ID NO. 114 | SEQ ID NO. 115 | SEQ ID NO. 116 |
| VH21 | SEQ ID NO. 117 | SEQ ID NO. 118 | SEQ ID NO. 119 |
| VH22 | SEQ ID NO. 120 | SEQ ID NO. 121 | SEQ ID NO. 122 |
| VH23 | SEQ ID NO. 123 | SEQ ID NO. 124 | SEQ ID NO. 125 |
| VH24 | SEQ ID NO. 126 | SEQ ID NO. 127 | SEQ ID NO. 128 |
| VH25 | SEQ ID NO. 129 | SEQ ID NO. 130 | SEQ ID NO. 131 |
| VH26 | SEQ ID NO. 132 | SEQ ID NO. 133 | SEQ ID NO. 134 |
| VH27 | SEQ ID NO. 135 | SEQ ID NO. 136 | SEQ ID NO. 137 |
| VH28 | SEQ ID NO. 138 | SEQ ID NO. 139 | SEQ ID NO. 140 |
| VH29 | SEQ ID NO. 141 | SEQ ID NO. 142 | SEQ ID NO. 143 |
| VH30 | SEQ ID NO. 144 | SEQ ID NO. 145 | SEQ ID NO. 146 |
| VH31 | SEQ ID NO. 147 | SEQ ID NO. 148 | SEQ ID NO. 149 |
| VH32 | SEQ ID NO. 150 | SEQ ID NO. 151 | SEQ ID NO. 152 |
| VH33 | SEQ ID NO. 153 | SEQ ID NO. 154 | SEQ ID NO. 155 |
| VH34 | SEQ ID NO. 156 | SEQ ID NO. 157 | SEQ ID NO. 158 |
| VH35 | SEQ ID NO. 159 | SEQ ID NO. 160 | SEQ ID NO. 161 |
| VH36 | SEQ ID NO. 162 | SEQ ID NO. 163 | SEQ ID NO. 164 |
| VH37 | SEQ ID NO. 165 | SEQ ID NO. 166 | SEQ ID NO. 167 |
| VH38 | SEQ ID NO. 168 | SEQ ID NO. 169 | SEQ ID NO. 170 |
| VH39 | SEQ ID NO. 171 | SEQ ID NO. 172 | SEQ ID NO. 173 |
| VH40 | SEQ ID NO. 174 | SEQ ID NO. 175 | SEQ ID NO. 176 |
| VH41 | SEQ ID NO. 177 | SEQ ID NO. 178 | SEQ ID NO. 179 |
| VH42 | SEQ ID NO. 180 | SEQ ID NO. 181 | SEQ ID NO. 182 |
| VH43 | SEQ ID NO. 183 | SEQ ID NO. 184 | SEQ ID NO. 185 |
| VH44 | SEQ ID NO. 186 | SEQ ID NO. 187 | SEQ ID NO. 188 |
| VH45 | SEQ ID NO. 189 | SEQ ID NO. 190 | SEQ ID NO. 191 |
| VH46 | SEQ ID NO. 192 | SEQ ID NO. 193 | SEQ ID NO. 194 |
| VH47 | SEQ ID NO. 195 | SEQ ID NO. 196 | SEQ ID NO. 197 |
| VH48 | SEQ ID NO. 198 | SEQ ID NO. 199 | SEQ ID NO. 200 |
| VH49 | SEQ ID NO. 201 | SEQ ID NO. 202 | SEQ ID NO. 203 |
| VH50 | SEQ ID NO. 204 | SEQ ID NO. 205 | SEQ ID NO. 206 |
| VH51 | SEQ ID NO. 207 | SEQ ID NO. 208 | SEQ ID NO. 209 |
| VH52 | SEQ ID NO. 210 | SEQ ID NO. 211 | SEQ ID NO. 212 |
| VH53 | SEQ ID NO. 213 | SEQ ID NO. 214 | SEQ ID NO. 215 |
| VH54 | SEQ ID NO. 216 | SEQ ID NO. 217 | SEQ ID NO. 218 |

each CDR1, CDR2 and CDR3 is coded according to the prevailing analysis methods of KABAT, Chothia or IMGT;

preferably, the substitution is a conservative amino acid substitution.

In particular, for example, the nanobody or the antigen-binding fragment of the invention, wherein:

(1) the CDR1, CDR2 and CDR3 have sequences as shown in SEQ ID NO. 57, 58 and 59, respectively;

(2) the CDR1, CDR2 and CDR3 have sequences as shown in SEQ ID NO. 60, 61 and 62, respectively;

(3) the CDR1, CDR2 and CDR3 have sequences as shown in SEQ ID NO. 63, 64 and 65, respectively;

(4) the CDR1, CDR2 and CDR3 have sequences as shown in SEQ ID NO. 66, 67 and 68, respectively;

(5) the CDR1, CDR2 and CDR3 have sequences as shown in SEQ ID NO. 69, 70 and 71, respectively;

(6) the CDR1, CDR2 and CDR3 have sequences as shown in SEQ ID NO. 72, 73 and 74, respectively;

(7) the CDR1, CDR2 and CDR3 have sequences as shown in SEQ ID NO. 76 and 77, respectively;

(8) the CDR1, CDR2 and CDR3 have sequences as shown in SEQ ID NO. 78, 79 and 80, respectively;

(9) the CDR1, CDR2 and CDR3 have sequences as shown in SEQ ID NO. 81, 82 and 83, respectively;

(10) the CDR1, CDR2 and CDR3 have sequences as shown in SEQ ID NO. 84, 85 and 86, respectively;

(11) the CDR1, CDR2 and CDR3 have sequences as shown in SEQ ID NO. 87, 88 and 89, respectively;

(12) the CDR1, CDR2 and CDR3 have sequences as shown in SEQ ID NO. 91 and 92, respectively;

(13) the CDR1, CDR2 and CDR3 have sequences as shown in SEQ ID NO. 93, 94 and 95, respectively;

(14) the CDR1, CDR2 and CDR3 have sequences as shown in SEQ ID NO. 96, 97 and 98, respectively;

(15) the CDR1, CDR2 and CDR3 have sequences as shown in SEQ ID NO. 99, 100 and 101, respectively;

(16) the CDR1, CDR2 and CDR3 have sequences as shown in SEQ ID NO. 102, 103 and 104, respectively;

(17) the CDR1, CDR2 and CDR3 have sequences as shown in SEQ ID NO. 105, 106 and 107, respectively;

(18) the CDR1, CDR2 and CDR3 have sequences as shown in SEQ ID NO. 108, 109 and 110, respectively;

(19) the CDR1, CDR2 and CDR3 have sequences as shown in SEQ ID NO. 111, 112 and 113, respectively;

(20) the CDR1, CDR2 and CDR3 have sequences as shown in SEQ ID NO. 114, 115 and 116, respectively;

(21) the CDR1, CDR2 and CDR3 have sequences as shown in SEQ ID NO. 117, 118 and 119, respectively;

(22) the CDR1, CDR2 and CDR3 have sequences as shown in SEQ ID NO. 120, 121 and 122, respectively;

(23) the CDR1, CDR2 and CDR3 have sequences as shown in SEQ ID NO. 123, 124 and 125, respectively;

(24) the CDR1, CDR2 and CDR3 have sequences as shown in SEQ ID NO. 126, 127 and 128, respectively;

(25) the CDR1, CDR2 and CDR3 have sequences as shown in SEQ ID NO. 129, 130 and 131, respectively;

(26) the CDR1, CDR2 and CDR3 have sequences as shown in SEQ ID NO. 132, 133 and 134, respectively;

(27) the CDR1, CDR2 and CDR3 have sequences as shown in SEQ ID NO. 135, 136 and 137, respectively;

(28) the CDR1, CDR2 and CDR3 have sequences as shown in SEQ ID NO. 138, 139 and 140, respectively;

(29) the CDR1, CDR2 and CDR3 have sequences as shown in SEQ ID NO. 141, 142 and 143, respectively;

(30) the CDR1, CDR2 and CDR3 have sequences as shown in SEQ ID NO. 144, 145 and 146, respectively;

(31) the CDR1, CDR2 and CDR3 have sequences as shown in SEQ ID NO. 147, 148 and 149, respectively;

(32) the CDR1, CDR2 and CDR3 have sequences as shown in SEQ ID NO. 150, 151 and 152, respectively;

(33) the CDR1, CDR2 and CDR3 have sequences as shown in SEQ ID NO. 153, 154 and 155, respectively;

(34) the CDR1, CDR2 and CDR3 have sequences as shown in SEQ ID NO. 156, 157 and 158, respectively;

(35) the CDR1, CDR2 and CDR3 have sequences as shown in SEQ ID NO. 159, 160 and 161, respectively;

(36) the CDR1, CDR2 and CDR3 have sequences as shown in SEQ ID NO. 162, 163 and 164, respectively;

(37) the CDR1, CDR2 and CDR3 have sequences as shown in SEQ ID NO. 165, 166 and 167, respectively;

(38) the CDR1, CDR2 and CDR3 have sequences as shown in SEQ ID NO. 168, 169 and 170, respectively;

(39) the CDR1, CDR2 and CDR3 have sequences as shown in SEQ ID NO. 171, 172 and 173, respectively;

(40) the CDR1, CDR2 and CDR3 have sequences as shown in SEQ ID NO. 174, 175 and 176, respectively;

(41) the CDR1, CDR2 and CDR3 have sequences as shown in SEQ ID NO. 177, 178 and 179, respectively;

(42) the CDR1, CDR2 and CDR3 have sequences as shown in SEQ ID NO. 180, 181 and 182, respectively;
(43) the CDR1, CDR2 and CDR3 have sequences as shown in SEQ ID NO. 183, 184 and 185, respectively;
(44) the CDR1, CDR2 and CDR3 have sequences as shown in SEQ ID NO. 186, 187 and 188, respectively;
(45) the CDR1, CDR2 and CDR3 have sequences as shown in SEQ ID NO. 189, 190 and 191, respectively;
(46) the CDR1, CDR2 and CDR3 have sequences as shown in SEQ ID NO. 192, 193 and 194, respectively;
(47) the CDR1, CDR2 and CDR3 have sequences as shown in SEQ ID NO. 195, 196 and 197, respectively;
(48) the CDR1, CDR2 and CDR3 have sequences as shown in SEQ ID NO. 198, 199 and 200, respectively;
(49) the CDR1, CDR2 and CDR3 have sequences as shown in SEQ ID NO. 201, 202 and 203, respectively;
(50) the CDR1, CDR2 and CDR3 have sequences as shown in SEQ ID NO. 204, 205 and 206, respectively;
(51) the CDR1, CDR2 and CDR3 have sequences as shown in SEQ ID NO. 207, 208 and 209, respectively;
(52) the CDR1, CDR2 and CDR3 have sequences as shown in SEQ ID NO. 210, 211 and 212, respectively;
(53) the CDR1, CDR2 and CDR3 have sequences as shown in SEQ ID NO. 213, 214 and 215, respectively;
(54) the CDR1, CDR2 and CDR3 have sequences as shown in SEQ ID NO. 216, 217 and 218, respectively; or, The CDR1, CDR2 and CDR3 have a sequence combination having 1, 2, 3 or more amino acid insertions, deletions and/or substitutions compared with the above sequence combinations (1)-(54).

In another specific embodiment, the invention provides an antibody or an antigen-binding fragment thereof comprising:

(1) a variable region having a sequence as shown in SEQ ID NO: 21, or a sequence with 70%, 75%, 80%, 85%, 90%, 95%, 96%, 97%, 98%, 99% or greater identity with the sequence shown above;
(2) a variable region having a sequence as shown in SEQ ID NO: 23, or a sequence with 70%, 75%, 80%, 85%, 90%, 95%, 96%, 97%, 98%, 99% or greater identity with the sequence shown above;
(3) a variable region having a sequence as shown in SEQ ID NO: 25, or a sequence with 70%, 75%, 80%, 85%, 90%, 95%, 96%, 97%, 98%, 99% or greater identity with the sequence shown above;
(4) a variable region having a sequence as shown in SEQ ID NO: 27, or a sequence with 70%, 75%, 80%, 85%, 90%, 95%, 96%, 97%, 98%, 99% or greater identity with the sequence shown above;
(5) a variable region having a sequence as shown in SEQ ID NO: 29, or a sequence with 70%, 75%, 80%, 85%, 90%, 95%, 96%, 97%, 98%, 99% or greater identity with the sequence shown above;
(6) a variable region having a sequence as shown in SEQ ID NO: 31, or a sequence with 70%, 75%, 80%, 85%, 90%, 95%, 96%, 97%, 98%, 99% or greater identity with the sequence shown above;
(7) a variable region having a sequence as shown in SEQ ID NO: 33, or a sequence with 70%, 75%, 80%, 85%, 90%, 95%, 96%, 97%, 98%, 99% or greater identity with the sequence shown above;
(8) a variable region having a sequence as shown in SEQ ID NO: 35, or a sequence with 70%, 75%, 80%, 85%, 90%, 95%, 96%, 97%, 98%, 99% or greater identity with the sequence shown above;
(9) a variable region having a sequence as shown in SEQ ID NO: 37, or a sequence with 70%, 75%, 80%, 85%, 90%, 95%, 96%, 97%, 98%, 99% or greater identity with the sequence shown above;
(10) a variable region having a sequence as shown in SEQ ID NO: 39, or a sequence with 70%, 75%, 80%, 85%, 90%, 95%, 96%, 97%, 98%, 99% or greater identity with the sequence shown above; (11) a variable region having a sequence as shown in SEQ ID NO: 41, or a sequence with 70%, 75%, 80%, 85%, 90%, 95%, 96%, 97%, 98%, 99% or greater identity with the sequence shown above;
(12) a variable region having a sequence as shown in SEQ ID NO: 43, or a sequence with 70%, 75%, 80%, 85%, 90%, 95%, 96%, 97%, 98%, 99% or greater identity with the sequence shown above;
(13) a variable region having a sequence as shown in SEQ ID NO: 45, or a sequence with 70%, 75%, 80%, 85%, 90%, 95%, 96%, 97%, 98%, 99% or greater identity with the sequence shown above;
(14) a variable region having a sequence as shown in SEQ ID NO: 47, or a sequence with 70%, 75%, 80%, 85%, 90%, 95%, 96%, 97%, 98%, 99% or greater identity with the sequence shown above;
(15) a variable region having a sequence as shown in SEQ ID NO: 49, or a sequence with 70%, 75%, 80%, 85%, 90%, 95%, 96%, 97%, 98%, 99% or greater identity with the sequence shown above;
(16) a variable region having a sequence as shown in SEQ ID NO: 51, or a sequence with 70%, 75%, 80%, 85%, 90%, 95%, 96%, 97%, 98%, 99% or greater identity with the sequence shown above;
(17) a variable region having a sequence as shown in SEQ ID NO: 53, or a sequence with 70%, 75%, 80%, 85%, 90%, 95%, 96%, 97%, 98%, 99% or greater identity with the sequence shown above; or,
(18) a variable region having a sequence as shown in SEQ ID NO: 55, or a sequence with 70%, 75%, 80%, 85%, 90%, 95%, 96%, 97%, 98%, 99% or greater identity with the sequence shown above.

In a preferred embodiment, the antibody or the antigen-binding fragment thereof of the present invention binds to human CD22 with a dissociation constant (KD) of no more than 50 nM.

In a preferred embodiment, the antibody or the antigen-binding fragment thereof of the present invention comprises a sequence of the constant region of any one of human or murine antibody IgG1, IgG2, IgG3, IgG4, IgA, IgM, IgE or IgD; preferably, comprises a sequence of the constant region of human or murine antibody IgG1, IgG2, IgG3 or IgG4.

In a preferred embodiment, the antibody or the antigen-binding fragment thereof of the invention further comprises a heavy chain constant region sequence without a CH1 fragment.

In a preferred embodiment, the antibody or the antigen-binding fragment thereof of the present invention further comprises a heavy chain constant region sequence with CH2 and CH3 fragments.

In a preferred embodiment, the antibody or the antigen-binding fragment thereof of the invention is chimeric or humanized or fully human; preferably, the antibody or the antigen-binding fragment is selected from a monoclonal antibody, a polyclonal antibody, a natural antibody, an engineered antibody, a monospecific antibody, a multispecific antibody (for example, a bispecific antibody), a monovalent antibody, a multivalent antibody, a full-length antibody, an antibody fragment, a naked antibody, a conjugated antibody, a humanized antibody, a fully human antibody, Fab, Fab', F(ab')2, Fd, Fv, scFv, a diabody or a single domain antibody.

In a preferred embodiment, the antibody or the antigen-binding fragment thereof of the invention is further coupled with a therapeutic agent or a tracer; preferably, the therapeutic agent is selected from a radioisotope, a chemotherapeutic agent or an immunomodulator, and the tracer is selected from a radiological contrast agent, a paramagnetic ion, a metal, a fluorescent label, a chemiluminescence label, a ultrasound contrast agent or a photosensitizer.

In a preferred embodiment, the present invention also provides a multispecific antigen-binding molecule; preferably, the multispecific antigen-binding molecule comprises a first antigen-binding module and a second antigen-binding module, the first antigen-binding module comprises the antibody or the antigen-binding fragment described in any one of the above, the second antigen-binding module specifically binds to other antigens than CD22 or binds to a different CD22 epitope than the first antigen-binding module;

- preferably, the other antigens are selected from CD3, CD16, CD16A, CD4, CD5, CD8, CD14, CD15, CD19, CD20, CD21, CD23, CD25, CD33, CD37, CD38, CD40, CD40L, CD46, CD52, CD54, CD66(a-d), CD74, CD80, CD126, CD138, B7, MUC, Ia, HLA-DR, tenascin, VEGF, P1GF, ED-B fibronectin, oncogene products, IL-2, IL-6, TRAIL-R1 or TRAIL-R2;
- preferably, the multispecific antibody is "bispecific", "trispecific" or "tetraspecific".

In a preferred embodiment, the present invention provides a chimeric antigen receptor (CAR); preferably, the chimeric antigen receptor at least comprises an extracellular antigen-binding domain, a transmembrane domain and an intracellular signaling domain, and the extracellular antigen-binding domain comprises any of the CD22 antibody or the antigen-binding fragment described above.

In a preferred embodiment, the present invention provides an immune effector cell; preferably, the immune effector cell comprises the chimeric antigen receptor described above or a nucleic acid fragment encoding the chimeric antigen receptor described above;

- preferably, the immune effector cell is selected from a T cell, a NK cell (a natural killer cell), a NKT cell (a natural killer T cell), a monocyte, a macrophage, a dendritic cell or a mast cell; the T cell may be selected from an inflammatory T cell, a cytotoxic T cell, a regulatory T cell (Treg) or a helper T cell;
- preferably, the immune effector cell is an allogeneic immune effector cell or an autologous immune cell.

In a preferred embodiment, the present invention provides an isolated nucleic acid molecule encoding the nanobody, the antigen-binding fragment, or any combination thereof according to any one of the above aspects of the present invention, the multispecific antigen-binding molecule described above or the chimeric antigen receptor described above.

In some embodiments, the present invention provides an expression vector comprising the isolated nucleic acid molecule of the present invention described above.

In some embodiments, the present invention provides a host cell comprising the isolated nucleic acid molecule or the expression vector of the present invention described above.

In a preferred embodiment, the host cell is a eukaryotic cell or a prokaryotic cell; more preferably, the host cell is derived from a mammalian cell, a yeast cell, an insect cell, *Escherichia coli* and/or *Bacillus subtilis*; more preferably, the host cell is selected from HEK293E or Chinese hamster ovary (CHO) cell.

In some embodiments, the present invention provides a method for preparing an antibody or an antigen-binding fragment or a multispecific antigen-binding molecule, the method comprises culturing the host cell of the present invention described above under appropriate conditions, and isolating the antibody or the antigen-binding fragment or the multispecific antigen-binding molecule.

In some embodiments, the present invention provides a method for preparing an immune effector cell, wherein the CAR nucleic acid fragment described above is introduced into the immune effector cell, preferably, the method further comprises enabling the immune effector cell to express the CAR described above.

In some embodiments, the present invention provides a pharmaceutical composition comprising the antibody or the antigen-binding fragment of the present invention described above, the multispecific antigen-binding molecule of the present invention described above, the chimeric antigen receptor of the present invention described above, the immune effector cell of the present invention described above, the isolated nucleic acid molecule of the present invention described above, the expression vector of the present invention described above, the cell of the present invention described above, or a product (e.g., an antibody and an antigen-binding fragment) prepared by the method of the invention described above, and a pharmaceutically acceptable carrier.

In a preferred embodiment, the pharmaceutical composition further comprises a pharmaceutically acceptable carrier, diluent or adjuvant; more preferably, the pharmaceutical composition further comprises an additional antineoplastic agent.

In some embodiments, the present invention provides a method for preventing and/or treating a B cell disease, the method comprises administering the antibody or the antigen-binding fragment of the present invention described above, the multispecific antigen-binding molecule of the present invention described above, the chimeric antigen receptor of the present invention described above, the immune effector cell of the present invention described above, the isolated nucleic acid molecule of the present invention described above, the expression vector of the present invention described above, the cell of the present invention described above, a product (e.g., an antibody and an antigen-binding fragment) prepared by the method of the invention described above, or the pharmaceutical composition of the invention described above to a patient in need thereof. The B cell disease is preferably a tumor or an autoimmune disease;

- preferably, the tumor is selected from lymphoma or leukemia, the lymphoma or leukemia is selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, multiple myeloma;
- preferably, the autoimmune disease is selected from systemic lupus erythematosus (SLE), antiphospholipid antibody syndrome, multiple sclerosis, ulcerative colitis, Crohn's disease, rheumatoid arthritis, Sjogren's syndrome, Guillain-Barre syndrome, myasthenia gravis, large vessel vasculitis, medium vessel vasculitis, polyarteritis nodosa, pemphigus, scleroderma, pulmonary hemorrhage-nephritic syndrome, glomerular nephritis, primary biliary cirrhosis, Graves' disease, membranous nephropathy, autoimmune hepatitis, sprue, Addison's disease, polymyositis/dermatomyositis, monoclonal gamma globulin disease, factor VIII deficiency, cryoglobulinemia, peripheral neuropathy, IgM polyneuropathy, chronic neuropathy, and chronic lymphocytic thyroiditis.

In some embodiments, the present invention provides the use of the antibody or the antigen-binding fragment of the present invention described above, the multispecific antigen-binding molecule of the present invention described above, the chimeric antigen receptor of the present invention described above, the immune effector cell of the present invention described above, the isolated nucleic acid molecule of the present invention described above, the expression vector of the present invention described above, the cell of the present invention described above, a product (e.g., an antibody and an antigen-binding fragment) prepared by the method of the invention described above, or the pharmaceutical composition of the invention described above in the preparation of a drug for preventing and/or treating a B cell disease, and the B cell disease is preferably a tumor or an autoimmune disease;

preferably, the tumor is selected from lymphoma or leukemia, the lymphoma or leukemia is selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, multiple myeloma;

preferably, the autoimmune disease is selected from systemic lupus erythematosus (SLE), antiphospholipid antibody syndrome, multiple sclerosis, ulcerative colitis, Crohn's disease, rheumatoid arthritis, Sjogren's syndrome, Guillain-Barre syndrome, myasthenia gravis, large vessel vasculitis, medium vessel vasculitis, polyarteritis nodosa, pemphigus, scleroderma, pulmonary hemorrhage-nephritic syndrome, glomerular nephritis, primary biliary cirrhosis, Graves' disease, membranous nephropathy, autoimmune hepatitis, sprue, Addison's disease, polymyositis/dermatomyositis, monoclonal gamma globulin disease, factor VIII deficiency, cryoglobulinemia, peripheral neuropathy, IgM polyneuropathy, chronic neuropathy, and chronic lymphocytic thyroiditis.

In some embodiments, the present invention provides the antibody or the antigen-binding fragment of the present invention described above, the multispecific antigen-binding molecule of the present invention described above, the chimeric antigen receptor of the present invention described above, the immune effector cell of the present invention described above, the isolated nucleic acid molecule of the present invention described above, the expression vector of the present invention described above, the cell of the present invention described above, a product (e.g., an antibody and an antigen-binding fragment) prepared by the method of the invention described above, or the pharmaceutical composition of the invention described above for preventing and/or treating a B cell disease; The B cell disease is preferably a tumor or an autoimmune disease;

preferably, the tumor is selected from lymphoma or leukemia, the lymphoma or leukemia is selected from B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, multiple myeloma;

preferably, the autoimmune disease is selected from systemic lupus erythematosus (SLE), antiphospholipid antibody syndrome, multiple sclerosis, ulcerative colitis, Crohn's disease, rheumatoid arthritis, Sjogren's syndrome, Guillain-Barre syndrome, myasthenia gravis, large vessel vasculitis, medium vessel vasculitis, polyarteritis nodosa, pemphigus, scleroderma, pulmonary hemorrhage-nephritic syndrome, glomerular nephritis, primary biliary cirrhosis, Graves' disease, membranous nephropathy, autoimmune hepatitis, sprue, Addison's disease, polymyositis/dermatomyositis, monoclonal gamma globulin disease, factor VIII deficiency, cryoglobulinemia, peripheral neuropathy, IgM polyneuropathy, chronic neuropathy, and chronic lymphocytic thyroiditis.

In some embodiments, the present invention provides a kit comprising the antibody or the antigen-binding fragment of the present invention described above, the multispecific antigen-binding molecule of the present invention described above, the chimeric antigen receptor of the present invention described above, the immune effector cell of the present invention described above, the isolated nucleic acid molecule of the present invention described above, the expression vector of the present invention described above, the cell of the present invention described above, or a product (e.g., an antibody and an antigen-binding fragment) prepared by the method of the invention described above, or the pharmaceutical composition of the invention described above, and instructions for use.

Definition and Description of Terminology

Unless otherwise specified, the terms used herein have the meanings commonly understood by those of ordinary skill in the art. For a term that is explicitly defined herein, the meaning of the term is to be determined based on the definition.

As used herein, the term "antibody" (Ab) refers to an immunoglobulin molecule that specifically binds to or is immunoreactive with an antigen of interest and includes polyclonal, monoclonal, genetically engineered, and other modified forms of an antibody (including but not limited to a chimeric antibody, a humanized antibody, a fully human antibody, a heteroconjugate antibody (e.g. a bispecific, trispecific and tetraspecific antibody, a diabody, a triabody and a tetrabody, a antibody conjugate)) and an antigen-binding fragment of an antibody (including, for example, Fab', F(ab')2, Fab, Fv, rIgG and scFv fragment). Furthermore, unless otherwise indicated, the term "monoclonal antibody" (mAb) is intended to include both an intact antibody molecule and an incomplete antibody fragment (such as Fab and F(ab')2 fragment, which lacks the Fc fragment of the intact antibody (cleared more quickly from circulation in animals), thus lacking Fc-mediated effector function) capable of specifically binding to a target protein (see Wahl et al., J. Nucl. Med. 24:316, 1983; the content of which is incorporated herein by reference).

An "antibody" herein may be derived from any animal, including but not limited to humans and non-human animals selected from primates, mammals, rodents and vertebrates, such as camelids, llamas, guanaco, alpaca, sheep, rabbits, mice, rats or cartilaginous fishes (such as sharks).

The term "natural antibody" herein refers to an antibody produced and paired by the immune system of a multicellular organism. The term "engineered antibody" herein refers to a non-natural antibody obtained through genetic engineering, antibody engineering, etc. For example, "engineered antibody" includes a humanized antibody, a small molecule antibody (such as scFv, etc.), a bispecific antibody, etc.

The term "monospecific" herein refers to having one or more binding sites, wherein each binding site binds the same epitope of the same antigen.

The term "multispecific" herein refers to having at least two antigen binding sites, each of which binds a different epitope of the same antigen or a different epitope of a different antigen. Thus, terms such as "bispecific", "trispecific", "tetraspecific" and the like refer to the number of different epitopes to which an antibody/an antigen-binding molecule can bind.

The term "valence" herein refers to the presence of a defined number of binding sites in an antibody/an antigen-binding molecule. Thus, the terms "monovalent", "bivalent", "tetravalent" and "hexavalent" refer to the presence of one binding site, two binding sites, four binding site and six binding sites in an antibody/an antigen-binding molecule, respectively.

"Full-length antibody", "complete antibody" and "intact antibody" are used interchangeably herein to mean that they have a structure substantially similar to that of a natural antibody.

As used herein, the term "antigen-binding fragment" refers to one or more antibody fragments that retain the ability to specifically bind to a target antigen. The antigen-binding function of an antibody can be performed by a fragment of a full-length antibody. The antibody fragment can be Fab, F(ab')2, scFv, SMIP, a diabody, a triabody, an affibody, a nanobody, an aptamer or a domain antibody. Examples of a binding fragment encompassed by the term "antigen-binding fragment" of an antibody include, but are not limited to: (i) an Fab fragment, which is a monovalent fragment consisting of VL, VH, CL and CH1 domains; (ii) an F(ab)2 fragment, which is a bivalent fragment comprising two Fab fragments connected by a disulfide bond in the hinge region; (iii) an Fd fragment consisting of VH and CH1 domains; (iv) an Fv fragment consisting of the VL and VH domains of a single arm of an antibody; (V) dAb comprising VH and VL domains; (vi) dAb fragment consisting of a VH domain (Ward et al., Nature 341:544-546, 1989); (vii) dAb consisting of VH or VL domains; (viii) an isolated complementarity determining region (CDR); and (ix) a combination of two or more isolated CDRs, the CDRs may optionally be linked by a synthetic linker. Furthermore, although the two domains VL and VH of the Fv fragment are encoded by separate genes, these two domains can be joined using a recombinant method through a linker that enables forming a single protein chain (referred to as a single chain Fv (scFv); see e.g., Bird et al., Science 242:423-426, 1988 and Huston et al., Proc. Natl. Acad. Sci. USA 85:5879-5883, 1988) in which the VL and VH regions pair to form a monovalent molecule. These antibody fragments can be obtained using conventional techniques known to those skilled in the art, and these fragments are screened for use in the same manner as an intact antibody. The antigen-binding fragment can be produced by recombinant DNA techniques, enzymatic or chemical cleavage of an intact immunoglobulin, or in some embodiments by chemical peptide synthesis procedures known in the art.

As used herein, the term "CD22" refers to Siglec-2, a molecule belonging to the SIGLEC lectin family, which is present on the surface of mature B cells and to a lesser extent on certain immature B cells. The term "CD22" includes CD22 proteins of any human and non-human animal species, and specifically includes human CD22 as well as CD22 of non-human mammals.

As used herein, the term "bispecific antibody" refers to an antibody, typically a human or humanized antibody, that has monoclonal binding specificities for at least two different antigens. In the present invention, one of the binding specificities can be detected against an antigen epitope of CD22, and the other can be detected against another antigen epitope of CD22 or any other antigen except CD22, such as a cell surface protein, a receptor, a receptor subunit, a tissue-specific antigen, a virus-derived protein, a virus-encoded envelope protein, a bacterium-derived protein, or a bacterial surface protein.

As used herein, the term "chimeric" antibody refers to an antibody that has a variable sequence derived from an immunoglobulin of one organism (such as a rat or mouse) and a constant region derived from an immunoglobulin of a different organism, such as human. Methods for producing the chimeric antibody are known in the art. See, e.g., Morrison, 1985, Science 229(4719):1202-7; Oi et al., 1986, Bio Techniques 4:214-221; Gillies et al., 1985 J Immunol Methods 125:191-202; The above documents are incorporated herein by reference.

As used herein, the term "heavy chain antibody" refers to an antibody that lacks the light chains of an conventional antibody. The term specifically includes, but is not limited to, a homodimeric antibody comprising a VH antigen binding domain and CH2 and CH3 constant domains in the absence of a CH1 domain.

As used herein, the term "nanobody" refers to a natural heavy chain antibody without light chains in camel and cloning its variable region can obtain a single domain antibody, also known as VHH (Variable domain of heavy chain of heavy chain antibody), which only consists of a heavy chain variable region, and is the smallest functional antigen-binding fragment. For a further description of VHH and nanobody, reference is made to the review article by Muyldermans (2001, Reviews in Molecular Biotechnology 74:277-302), and to the following patent applications mentioned as general background art: WO 94/04678, WO 95/04079 and WO 96/34103 of the Free University of Brussels; WO 94/25591, WO 99/3768, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of Vlaams Instituut voor Biotechnologie (VIB); WO 03/050531 of Algonomics N.V. and Ablynx N.V.; WO 01/90190 of the National Research Council of Canada; WO 03/025020 (=EP 1433793) of the Institute of Antibodies; and WO 04/041867, WO 04/041862, WO 04/041865, WO 04/041863, WO 04/062551, WO 05/044858, WO 06/40153, WO 06/079372, WO 06/122786, WO 06/122787 and WO 06/122825 of Ablynx N.V., and further published patent applications of Ablynx N.V. Reference is also made to the additional prior art mentioned in these applications, in particular the list of references mentioned on pages 41-43 of International Application WO 06/040153, which list and references are incorporated herein by reference. As described in these references, nanobody (in particular VHH sequences and partially humanized nanobody) may inter alia be characterized by the presence of one or more "signature residues" in one or more framework sequences. Further descriptions of nanobody can be found in, for example, WO 08/101985 and WO 08/142164, including humanization and/or camelization of nanobody, as well as other modifications, parts or fragments, derivatives or "nanobody fusion", multivalent constructs (including some non-limiting examples of linker sequences) and various modifications that increase the half-life of a nanobody and a formulation thereof. For a further general description of nanobody, reference is made to the prior art cited herein, for example WO 08/020079 (page 16).

As used herein, the term "complementarity determining region" (CDR) refers to hypervariable regions found in both light and heavy chain variable domains. The more conserved portions in variable domains are called the framework regions (FR). As understood in the art, the amino acid positions representing the hypervariable regions of an antibody can vary according to the context and various definitions known in the art. Some positions within variable domains can be considered heterozygous hypervariable positions because these positions can be considered to be within the hypervariable regions under one set of criteria (such as IMGT or KABAT) but outside the hypervariable regions under a different set of criteria (such as KABAT or IMGT). One or more of these positions may also be found in extended hypervariable regions. The invention includes an antibody comprising modifications in these hybrid hypervariable positions. The variable domains of the native heavy and light chains respectively comprise four framework regions that largely adopt a sheet configuration and connected by three CDRs (CDR1, CDR2, and CDR3) that form loops connecting the sheets, and in some cases form part of the sheet structure. The CDRs in each chain are held tightly together by the FR regions in the order of FR1-CDR1-FR2-CDR2-FR3-CDR3-FR4, and together with CDRs from other antibody chains contribute to the formation of the antibody's antigen-binding site (see Kabat et al., Sequences of Proteins of Immunological Interest, National Institute of Health, Bethesda, Md. 1987; which is incorporated herein by reference). For example, herein, CDR1-VH, CDR2-VH, and CDR3-VH refer to the first CDR, the second CDR, and the third CDR of the heavy chain variable region (VH), respectively, and these three CDRs constitute the CDR combination (VHCDR combination) of the heavy chain (or its variable region); CDR1-VL, CDR2-VL, and CDR3-VL refer to the first CDR, the second CDR, and the third CDR of the light chain variable region (VL), respectively, and these three CDRs constitute the CDR combination (VLCDR combination) of the light chain (or its variable region).

As used herein, the term "monoclonal antibody" refers to an antibody derived from a single clone (including any eukaryotic, prokaryotic, or phage clone), without limitation by the method by which the antibody is produced.

As used herein, the term "VH" refers to the variable region of an immunoglobulin heavy chain of an antibody, including the heavy chain of an Fv, scFv or Fab. The term "VL" refers to the variable region of an immunoglobulin light chain, including the light chain of an Fv, scFv, dsFv or Fab.

The term "heavy chain constant region" herein refers to the carboxy-terminal portion of the heavy chain of an antibody, which is not directly involved in the binding of the antibody to an antigen, but exhibits effector functions, such as interaction with Fc receptors, and has a more conserved amino acid sequence relative to the antibody's variable domain. A "heavy chain constant region" comprises at least one of the following: a CH1 domain, a hinge region, a CH2 domain, a CH3 domain, or a variant or fragment thereof "Heavy chain constant region" includes "full-length heavy chain constant region" and "heavy chain constant region fragment", the former has a structure substantially similar to that of a natural antibody constant region, while the latter only includes "a part of the full-length heavy chain constant region". For example, a typical "full-length antibody heavy chain constant region" consists of CH1 domain-hinge region-CH2 domain-CH3 domain; when the antibody is IgE, it also includes a CH4 domain; when the antibody is a heavy chain antibody, it does not include the CH1 domain. For example, a typical "heavy chain constant region fragment" can be selected from CH1, Fc or CH3 domains.

The term "light chain constant region" herein refers to the carboxy-terminal portion of the light chain of an antibody, which is not directly involved in the binding of the antibody to an antigen. The light chain constant region may be selected from a constant κ domain or a constant λ domain.

The term "Fc" herein refers to the carboxy-terminal portion of an antibody obtained by papain hydrolysis of the intact antibody, which typically includes the CH3 and CH2 domains of the antibody. Fc region includes, for example, a native sequence Fc region, a recombinant Fc region and a variant Fc region. Although the boundary of the Fc region of an immunoglobulin heavy chain can vary slightly, the Fc region of a human IgG heavy chain is generally defined as extending from the amino acid residue at position Cys226 or from Pro230 to the carboxyl terminus. The C-terminal lysine of the Fc region (residue 447 according to the EU numbering system) may be removed, for example, during the production or purification of the antibody, or by recombinant engineering of the nucleic acid encoding the heavy chain of the antibody, thus the Fc region may comprise or may not comprise Lys447.

The term "humanized antibody" herein refers to a genetically engineered non-human antibody whose amino acid sequence has been modified to increase sequence homology with a human antibody. Generally speaking, all or part of the CDR regions of a humanized antibody are derived from a non-human antibody (donor antibody), and all or part of the non-CDR regions (for example, variable region FR and/or constant region) are derived from human Immunoglobulin (recipient antibody). Humanized antibody usually retain or partially retain the expected properties of the donor antibody, including but not limited to, antigen specificity, affinity, reactivity, ability to enhance immune cell activity, ability to enhance immune response, etc.

The term "fully human antibody" herein refers to an antibody having variable regions in which both the FRs and CDRs are derived from human germline immunoglobulin sequences. Furthermore, if the antibody comprises a constant region, the constant region also is derived from human germline immunoglobulin sequences. Fully human antibody herein may include amino acid residues not encoded by human germline immunoglobulin sequences (for example, mutations introduced by random or site-specific mutagenesis in vitro or by somatic mutation in vivo). However, a "fully human antibody" herein is not intended to include an antibody in which CDR sequences derived from the germline of another mammalian species (for example, mouse) have been grafted onto human framework sequences.

The term "naked antibody" herein refers to an antibody that is not linked, fused or conjugated to another agent or molecule (for example, label or drug), peptide or polypeptide. In specific embodiments, the naked antibody expressed by a mammalian host cell can be glycosylated by the host cell's glycosylation machinery (for example, glycosylase). In certain embodiments, the naked antibody is not glycosylated when expressed by a host cell that does not have its own glycosylation machinery (for example, glycosylase). In certain embodiments, the naked antibody is an intact antibody, while in other embodiments, the naked antibody is the antigen-binding fragment of an inact antibody, such as Fab antibody.

The term "conjugated antibody" herein refers to an antibody that can be associated with a pharmaceutically acceptable carrier or diluent and can be a monoclonal antibody, a chimeric antibody, a humanized antibody, or a human antibody.

The term "diabody" herein refers to bivalent bispecific antibody that can bind to different epitopes on the same or different antigens.

As used herein, the term "percent (%) sequence identity" refers to the percentage of amino acid (or nucleotide) residues of the candidate sequence that are identical to those of the reference sequence after aligning the sequences and introducing gaps (if necessary) in order to achieve maximum percentage sequence identity (for example, for optimal alignment, gaps can be introduced in one or both of the candidate sequence and the reference sequence, and non-homologous sequences can be ignored for comparison purpose). For purpose of determining percent sequence identity, alignment can be achieved in a variety of ways well known to those skilled in the art, for example, using publicly available computer software such as BLAST, ALIGN or Megalign (DNASTAIi) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence shows sequence identity from 50% to 100% in the full length of the candidate sequence or in the selected part of the continuous amino acid (or nucleotide) residues of the candidate sequence. The length of the candidate sequence aligned for comparison purpose is at least 30% (e.g., 30%, 40%, 50%, 60%, 70%, 80%, 90% or 100%) of the length of the reference sequence. When a position in the candidate sequence is occupied by the same amino acid (or nucleotide) residue as the corresponding position in the reference sequence, then the molecules are identical at that position.

The term "conservative amino acid" herein generally refers to amino acids that belong to the same class or have similar characteristics (for example, charge, side chain size, hydrophobicity, hydrophilicity, backbone conformation, and rigidity). For example, the amino acids in each of the following groups belong to each other's conservative amino acid residues, and the substitution of amino acid residues in the group belongs to the conservative amino acid substitution:

(1) acidic amino acids: Asp(D) and Glu(E);
(2) basic amino acids: Lys (K), Arg (R) and His (H);
(3) hydrophilic uncharged amino acids: Ser (S), Thr (T), Asn (N) and Gin (Q);
(4) Aliphatic uncharged amino acids: Gly (G), Ala (A), Val (V), Leu (L) and Ile (I);
(5) nonpolar uncharged amino acids: Cys (C), Met (M) and Pro (P);
(6) aromatic amino acids: Phe (F), Tyr (Y) and Trp (W).

The term "Kabat numbering system" herein generally refers to the immunoglobulin alignment and numbering system proposed by Elvin A. Kabat (see, for example, Kabat et al., Sequences of Proteins of Immunological Interest, 5th Ed. Public Health Service, National Institutes of Health, Bethesda, Md., 1991; which is incorporated herein by reference).

The term "Chothia numbering system" herein generally refers to the immunoglobulin numbering system proposed by Chothia et al., which is a classical rule for identifying the boundaries of CDR regions based on the location of structural loop regions (see, for example, Chothia & Lesk (1987) J. Mol. Biol. 196:901-917; Chothia et al. (1989) Nature 342:878-883; which is incorporated herein by reference).

The term "IMGT numbering system" herein generally refers to the immunoglobulin numbering system proposed by Chothia et al., which is a classical rule for identifying the boundaries of CDR regions based on the location of structural loop regions (see, for example, Chothia & Lesk (1987) J. Mol. Biol. 196:901-917; Chothia et al. (1989) Nature 342:878-883; which is incorporated herein by reference).

As used herein, the term "specific binding" refers to a binding reaction that determines the presence of an antigen in a heterogeneous population of proteins and other biomolecules, the proteins and other biomolecules are for example specifically recognized by an antibody or an antigen-binding fragment thereof. An antibody or an antigen-binding fragment thereof that specifically binds to an antigen would bind to the antigen with a $K_D$ of less than 100 nM. For example, an antibody or an antigen-binding fragment thereof that specifically binds to an antigen would bind to the antigen with a KD of up to 100 nM (for example, between 1 pM and 100 nM). An antibody or an antigen-binding fragment thereof that does not exhibit specific binding to a particular antigen or an epitope thereof would exhibit a KD for the particular antigen or the epitope thereof of greater than 100 nM (for example, greater than 500 nM, 1 μM, 100 μM, 500 μM, or 1 mM). Various immunoassays are available to select for an antibody that reacts specifically with a specific protein or carbohydrate. For example, solid-phase ELISA immunoassay is routinely used to select for an antibody that reacts specifically with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), which describes immunoassay methods and conditions that can be used to determine specific immunoreactivity.

As used herein, the term "antibody conjugate" refers to a coupled entity/conjugate formed by chemically bonding an antibody molecule to another molecule either directly or through a linker. Examples include antibody-drug conjugate (ADC), in which the drug molecule is said another molecule.

The term "chimeric antigen receptor (CAR)" herein refers to a recombinant protein comprising at least (1) an extracellular antigen-binding domain, such as a variable heavy or light chain of an antibody, and (2) a transmembrane domain used to make the anchored CAR enter immune effector cells, and (3) an intracellular signaling domain. In certain embodiments, the extracellular antigen binding domain of the CAR comprises a scFv. The scFv can be derived from the variable heavy and light regions of a fusion antibody. Alternatively or additionally, the scFv may be derived from Fab's (rather than an antibody, for example obtained from a Fab library). In certain embodiments, the scFv is fused to the transmembrane domain and then to the intracellular signaling domain.

Herein the term "nucleic acid" includes any compound and/or substance comprising a polymer of nucleotides. Each nucleotide consists of a base, specifically a purine or pyrimidine base (i.e., cytosine (C), guanine (G), adenine (A), thymine (T) or uracil (U)), a sugar (i.e., deoxyribose or ribose) and a phosphate group. Typically, the nucleic acid molecule is described by a sequence of bases, whereby the bases represent the primary structure (linear structure) of the nucleic acid molecule. The sequence of bases is usually expressed as 5' to 3'. In this context, the term nucleic acid molecule encompasses deoxyribonucleic acid (DNA), including for example complementary DNA (cDNA) and genomic DNA, ribonucleic acid (RNA), especially messenger RNA (mRNA), synthetic forms of DNA or RNA, and a polymer containing a mixture of two or more of these molecules. The nucleic acid molecule can be linear or circular. Furthermore, the term nucleic acid molecule includes both sense strand and antisense strand, as well as single-stranded form and double-stranded form. Furthermore, the nucleic acid molecules described herein may contain naturally occurring or non-naturally occurring nucleotides. Examples of non-naturally occurring nucleotides include modified nucleotide bases with derivatized sugar or phosphate backbone linkages or chemically modified residues. The nucleic acid molecule also encompasses DNA and RNA molecules which are suitable as vectors for direct expression of the antibody of the invention in vitro and/or in vivo, for example in a host or patient. Such DNA (for example cDNA) or RNA (for example mRNA) vectors may be unmodified or modified. For example, mRNA can be chemically modified to enhance the stability of the RNA vector and/or the expression of the encoded molecule, so that the mRNA can be injected into a subject to generate an antibody in vivo (see, for example, Stadler et al., Nature Medicine 2017, Published online Jun. 12, 2017, doi: 10.1038/nm.4356 or EP 2 101 823 B1).

As used herein, the term "vector" includes a nucleic acid vector, such as a DNA vector (such as a plasmid), an RNA vector, a virus or other suitable replicons (such as viral vectors). A variety of vectors have been developed for the delivery of polynucleotides encoding foreign proteins into prokaryotic or eukaryotic cells. The expression vector of the invention contains polynucleotide sequences together with additional sequence elements, for example, for expressing proteins and/or integrating these polynucleotide sequences into the genome of mammalian cells. Certain vectors that can be used to express the antibody and the antibody fragment of the invention include plasmids that contain regulatory sequences (such as promoter and enhancer regions) that direct transcription of the gene. Other useful vectors for expressing the antibody and the antibody fragment contain polynucleotide sequences that enhance the rate of translation of these genes or improve the stability or nuclear export of mRNA transcripted from the genes. These sequence elements include, for example, 5' and 3' untranslated regions, internal ribosomal entry site (IRES), and polyadenylation signal site in order to direct the efficient transcription of the genes carried on the expression vector. The expression vector of the present invention may also contain a polynucleotide encoding a marker for selection of cells containing such a vector. Examples of suitable markers include genes encoding resistance to antibiotics such as ampicillin, chloramphenicol, kanamycin or nourseothyrcin.

The term "host cell" herein refers to a cell into which a foreign nucleic acid is introduced, including the progenys of such a cell. The host cell includes "transformant" and "transformed cell" which include the primary transformed cell and progeny derived therefrom, regardless of the number of passages. The progeny may not be identical to the parental cell in nucleic acid content, and may contain a mutation. The mutant progeny with the same function or biological activity as those screened or selected in the initially transformed cells are included herein.

As used herein, the term "pharmaceutical composition" refers to a preparation that is present in a form which allows the active ingredients contained therein to be biologically effective and does not contain additional ingredients that would be unacceptably toxic to the subject to which the pharmaceutical composition is administered.

As used herein, the terms "subject", "object" and "patient" refer to an organism receiving treatment for a particular disease or condition, such as a cancer or an infectious disease, as described herein. Examples of subjects and patients include mammals, such as humans, primates, pigs, goats, rabbits, hamsters, cats, dogs, guinea pigs, members of the bovid family (cattle, bison, buffalo, elk, yak, etc.), sheep, and horses receiving treatment for a disease or a condition (for example, a cell proliferative disorder, such as a cancer or an infectious disease).

As used herein, the term "treatment" refers to surgical or therapeutic treatment, the purpose of which is to prevent, slow down (reduce) an undesired physiological change or pathology in the subject being treated, such as the progress of a cell proliferative disorder (such as a cancer or an infectious disease). Beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial response or complete response), whether detectable or undetectable. Subjects in need of treatment include subjects who already have a condition or a disease, subjects who are prone to a condition or a disease or subjects who intend to prevent a condition or a disease. When referring to the terms slow down, alleviation, diminishment, palliation, remission, etc., the meaning of eliminate, disappear, not occur, etc. is also included.

The term "effective amount" herein refers to an amount of a therapeutic agent effective to prevent or relieve a disease or a condition or the progression of the disease when administered alone or in combination with another therapeutic agent to a cell, tissue or subject. "Effective amount" also refers to an amount of a compound sufficient to relieve symptoms, for example, treat, cure, prevent or relieve the associated medical conditions, or to increase the rate of treatment, cure, prevent or relieve such conditions. When the active ingredient is administered to an individual alone, a therapeutically effective dose refers to the ingredient alone. When a combination is used, a therapeutically effective dose refers to the combined amounts of the active ingredients that produce a therapeutic effect, whether administered in combination, sequentially or simultaneously.

The term "appropriate condition" herein refers to a condition suitable for culturing various host cells, including eukaryotic cells and prokaryotic cells.

The term "cancer" herein refers to or describes the physiological condition in mammals that is typically characterized by unregulated cell growth. Both benign and malignant cancers are included in this definition.

The term "tumor" herein refers to all neoplastic cell growth and proliferation, whether malignant or benign, and to all pre-cancerous and cancerous cells and tissues. The terms "cancer" and "tumor" are not mutually exclusive when referred to herein.

The term "anti-tumor agent" herein refers to an anti-tumor drug, which is a class of drugs for the treatment of tumor diseases, including a chemotherapy drug, a biological agent and the like.

The term "EC50" herein refers to the half-maximal effective concentration, which includes the concentration of an antibody that induces a response halfway between baseline and maximum after a specified exposure time. EC50 essentially represents the concentration of an antibody at which 50% of its maximal effect is observed and which can be measured by methods known in the art.

The term "EC80" herein refers to the concentration of an antibody that elicits 80% of the maximal effect.

BRIEF DESCRIPTION OF THE DRAWINGS

Unless otherwise defined herein, scientific and technical terms related to the present invention shall have the meanings understood by those of ordinary skill in the art.

FIG. 5 shows the FACS screen and detection results of CHO-K1 cells transfected with human CD22 protein.

FIG. 8 shows the binding reaction of the VHH-Fc antibodies of the present invention with murine CD22-ECD-His protein detected by ELISA; The positive control is 983; the negative control is hIgG1;

FIG. 13 shows the inhibition rate between VI-1H antibodies of the present invention detected by competitive ELISA.

DETAILED DESCRIPTION OF EMBODIMENTS

The present invention will be further described below in conjunction with specific examples, and the advantages and characteristics of the present invention will become clearer along with the description. If specific conditions are not specified in the examples, conventional conditions or conditions recommended by a manufacturer are followed. The reagents or instruments used therein for which manufacturers are not specified are all conventional products that are commercially available.

The examples of the present invention are merely exemplary, and do not limit the scope of the present invention in any way. Those skilled in the art should understand that the details and forms of the technical solutions of the present invention can be modified or replaced without departing from the spirit and scope of the present invention, but these modifications and replacements all fall within the protection scope of the present invention.

Example 1 Screening of Single Domain Antibody Against Human CD22

1.1 Immunization and Serum Titer Detection of Alpaca

Figure 1A:
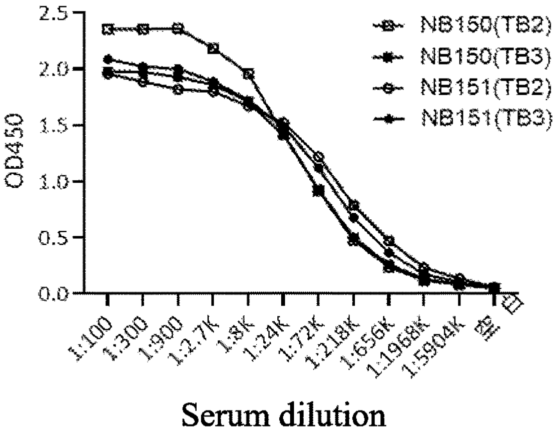
FIG. 1A shows the serum antibody titer of alpaca immunized with human CD22-ECD protein detected by ELISA.
Figure 1B:
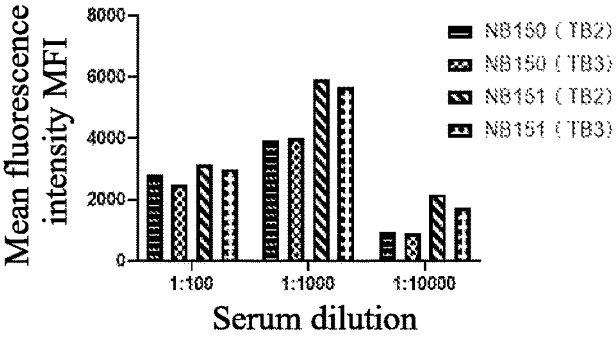
FIG. 1B shows the serum antibody titer of alpaca immunized with human CD22-ECD protein detected by FACS.

The human CD22 (Asp20-Arg687)-His protein used for immunization was purchased from ACRO Biosystems (catalog number: CD2-H52H8). Two alpacas (Llama) were selected for immunization, and each alpaca was immunized four times with an interval of 3 weeks. After the third immunization and after the fourth immunization, peripheral blood was collected and serum was separated, and enzyme-linked immunosorbent assay (ELISA) and flow cytometry (FACS) were used to detect the antibody titer and specificity against human CD22 in serum, and the results are shown in FIGS. 1A-1B and Table 1. Table 1 shows that for the alpaca immunized with human CD22, the serum after immunization has different degrees of binding to the immunogen, showing antigen-antibody reactions, and the highest dilution is about 5.9 million. The blank control is 1% (w/w) BSA, and the batch refers to the alpaca serum on the seventh day after the third (TB2) and fourth (TB3) immunization, and the data in the table are OD450 nm values.

TABLE 1

The serum antibody titer of alpaca immunized with human CD22 protein detected by ELISA OD450 nm

| | Batch | | | |
|---|---|---|---|---|
| Serum dilution | NB150 (TB2) | NB150 (TB3) | NB151 (TB2) | NB151 (TB3) |
| 1:100 | 2.36 | 1.98 | 1.96 | 2.09 |
| 1:300 | 2.36 | 1.98 | 1.89 | 2.02 |
| 1:900 | 2.36 | 1.93 | 1.82 | 2.00 |
| 1:2700 | 2.18 | 1.86 | 1.80 | 1.89 |
| 1:8100 | 1.96 | 1.71 | 1.67 | 1.72 |
| 1:24300 | 1.42 | 1.41 | 1.52 | 1.49 |
| 1:72900 | 0.92 | 0.93 | 1.22 | 1.12 |
| 1:218700 | 0.48 | 0.50 | 0.79 | 0.68 |
| 1:656100 | 0.24 | 0.26 | 0.47 | 0.37 |
| 1:1968300 | 0.12 | 0.14 | 0.23 | 0.18 |
| 1:5904900 | 0.09 | 0.09 | 0.14 | 0.11 |
| Blank control | 0.050 | 0.05 | 0.06 | 0.05 |

1.2 Library Construction

A total of 100 mL of alpaca peripheral blood was collected after three immunizations and after four immunizations; Lymphocyte separation medium was used to isolate PBMC, RNAiso Plus reagent (Takara, catalog number: #9108/9109) was used to extract total RNA, and PrimeScript™ II 1st Strand cDNA Synthesis Kit (Takara, catalog number: 6210A) was used to reverse transcribe the extracted RNA into cDNA. Nested PCR was used to amplify the variable region nucleic acid fragment encoding the nanobody:

the first round of PCR:

```
upstream primer:
                                    (SEQ ID NO. 16)
CTTGGTGGTCCTGGCTGC

downstream primer:
                                    (SEQ ID NO. 17)
GGTACGTGCTGTTGAACTGTTCC
```

the second round of PCR:

the first round PCR product was used as a template,

```
upstream primer:
                                    (SEQ ID NO. 18)
CATGCCATGACTGTGGCCCAGGCGGCCCAGKT
GCAGCTCGTGGAGTC

downstream primer-1:
                                    (SEQ ID NO. 19)
CATGCCATGACTCGCGGCCGGCCTGGCCATGGGGGTCTTCGCTGTG
GTGCG

downstream primer-2:
                                    (SEQ ID NO. 20)
CATGCCATGACTCGCGGCCGGCCTGGCCGTCTTGTGGTTTTGGTGT
CTTGGG
```

The nucleic acid fragment of the nanobody of interest was recovered and cloned into the phage display vector pcomb3XSS (from Sichuan NB Biolab Co., Ltd) using the restriction endonuclease SfiI (NEB, catalog number: R0123S). The product was then electrotransformed into *Escherichia coli* electroporation competent cell TG1, and a nanobody phage display library target against CD22 was constructed and tested. By serial dilution plating, the calculated capacity is $2.0\times10^9$. To test the insertion rate of the library, 48 clones were randomly selected for colony PCR. The results showed that the insertion rate reached 100%.

1.3 Panning of Nanobody VHH Against CD22

The plate was coated with human CD22-llama Fc fusion protein (ACRO Biosystems, catalog number: 512-H525a) at 0.5 μg/well, and placed at 4° C. overnight; The next day, after blocking with 3% BSA-PBS at 37° C. for 1 hour, 100 μl of phage display library was added and incubated at 37° C. for 1 hour; After that, the plate was washed 6 times with PBST and 2 times with PBS to wash away unbound phages. Finally, 100 μL of Gly-HCl eluent was added to elute the phages that specifically bind to CD22 to enrich positive clones.

1.4 Screening of Specific Single Positive Clones by Phage Enzyme-Linked Immunoassay After panning, blank *Escherichia coli* were infected with the obtained CD22-binding positive phages and plated. Then 96 single colonies were selected for proliferation and culture. The plates were coated with human CD22-llama Fc and human CD22-His proteins respectively at 4° C. overnight, the phage culture supernatant was added, and incubated at 37° C. for 1 hour. After washing, TMB chromogenic solution was added to develop color, and the optical density was measured at a wavelength of 450 nm. Human CD22-llama Fc and human CD22-His double-positive clones were selected for sequencing. The sequencing results were analyzed using MOE software, and the evolutionary tree was constructed according to the amino acid sequence coding the VHH protein. According to the sequence similarity, 18 clones were obtained by eliminating the sequences that were close to each other on the evolutionary tree, and the CDR sequences of the 18 clones were analyzed by KABAT, Chothia or IMGT software respectively, and the corresponding sequence information was shown in the following table 2-4. Wherein Table 2 showed the antibody sequences represented by amino acids of 18 nanobody molecules, and Table 3 showed the antibody sequences represented by nucleotides of 18 nanobody molecules, and Table 4 showed the results of IMGT, Kabat and Chothia analysis of the CDRs of 18 nanobody molecules. Subsequently, the production and identification of VHH nanobody Fc fusion protein were carried out.

TABLE 2

Specific amino acid sequence information of the heavy chain variable region of the anti-CD22 antibody

| Antibody number | Sequence number | Heavy chain variable region sequence (VH) |
|---|---|---|
| S002-NB 150-42 | SEQ ID NO. 21 | QVQLVESGGGLVQAGDSLKLSCLASGITFSSYYMSWFRQAPGKEREF VAGVGRSGAPSHHADSVKGRFTISRDNAKSÅVYLQMNSLQPEDTAVY FCAAKWMAASTTVADYWGQGTQVTVSS |
| S002-NB 150-5 | SEQ ID NO. 23 | QLQLVESGGGLVQAGGSLRLSCVGSGDRVSIALMGWFRQAPGKERE FVAAISPSGGRITYSQSVKGRFTISRDNAKNTVYLQMNSLKRDDTAVY VCAANFRGYLSSSRGSDYAYWGQGTQVTVSS |
| S002-NB 150-40 | SEQ ID NO. 25 | QVQLVESGGGLVQDGGSLRLSCAASGLTFSFYNMGWFRQAPGKERE FVAAISQSGLSTHYADSMKGRFTISRQNAKNTVYLQMNSLNPVDTAAY YCAAGRRGYLASTTNDYEYWGQGTQVTVSS |
| S002-NB 150-57 | SEQ ID NO. 27 | QVQLVESGGGLVQAGDSLRLSCAVTGRAYSRSDMGWFRQAPGKER EIVAVITFGGGTDYADSVKGRFTISSEDTKNTLYLQMNSLQPEDTAVYY CAAGFRGSRWSTAARRKEDDYAFWGQGTQVTVSS |
| S002-NB 150-2 | SEQ ID NO. 29 | QVQLVESGGGLVQPGGSLRLSCAASGSWFNIAMGWFRQAPGKEREF VAGIRWSDSKTYYADSVKGRATISGDNAKNTTYLQMNSLKPEDTAVYY CAAQRYYRGSYNRQTNYDHWGQGTQVTVSS |
| S002-NB 151-14 | SEQ ID NO. 31 | QVQLVESGGGLVQAGGSLRLSCTTSGGTLSRITMGWFRQAPGKERE FVAAIKWGGSSTPYSDSVKGRFTISRQNAKNTVYLQMDRLVPEDTAVY YCAGGLRGPYSDSVTSSVQYNYWGQGTQVTVSS |
| S002-NB 151-51 | SEQ ID NO. 33 | QVQLVESGGGLVQAGGSLRLSCAASGITSDDYAIGWFRQAPGKEREG VSCMYSSDGSTYYADSVKGRFTISRQNAKNTVYLQMNSLRPEDTAVY HCAAGPWCFVTGVGREEWGQGTQVTVSS |
| S002-NB 151-2 | SEQ ID NO. 35 | QVQLVESGGGLVQAGDSLRLSCAASGRTFSPSTMAWFRQAPGKERE LVARIGWTYGDTYYVDSAKGISMQNVKNTVYLQMNSLKPEDTAV YYCAALFRGGLSYNFSNRGTQVTVSS |
| S002-NB 151-82 | SEQ ID NO. 37 | EVQVVESGGGLVQAGDSLRLSCTT5GRTFYGDYIAWFRQAPGKEREF VAAIAVRGRGTFYGQSVKGRFTISRDNAENTLSLQMNSLKPEDTAVYY CAADAGSYASRGFPVRETGRYDYWGQGTQVTVSS |
| S002-NB 151-23 | SEQ ID NO. 39 | QVQLVESGGGLVQAGGSLTVSCTNSGRTLSTSTIAWFRQKPGKDSEF VAAIRWSGGMGWYADSVKGRFTISRDNAENTVSLQMNTLQPEDTAV YFCAVSTVPYYGSIYTRVGDYPYWGQGTQVTVSS |
| S002-NB 151-66 | SEQ ID NO. 41 | QVQLVESGGGLVQAGGSLRLACAÅSGDTVSIYYMGWFRQAPGKERE FVGALSASGQFTDHADSVKGRFTISRDDAQNTVFLHMNDLKPEDTAV YYCAVQRYGWVYRTDKTMYNYWGQGTQVTVSS |
| S002-NB 151-92 | SEQ ID NO. 43 | QVQLVESGGGLVQSGGSLRLSCAASGFTFSDYTMNWVRQAPGKGLE WWSEISSGGHFKSNADSVKDRFTISRQNAKNTLYLQMNSLKPEDTAVY FCAKCPRPSVYQRDYESTSLYRGQGTQVTVSS |
| S002-NB 151-64 | SEQ ID NO. 45 | QVQLVESGGGLVQPGGSLTLSCAASGFQFSFYTMTWVRQAQGKGLE WWVSTISTGGGGSNYADSVKGRFTISRDNAKKTLYLQMTSLKPEDTAVY YCASHRRGYMFVSSRKNEYDYWGRGTQVTVSS |
| S002-NB 151-30 | SEQ ID NO. 47 | QVQLVESGGGLVQAGGSLRLSCAASGRASGSGAMGWFRQAPGQER RFVAGIEWSSGGPVYADSVKGRFTLSRQNAKNTVHLQMNSLKPEDTA VYYCAAAPWWFSSPDDYMYWGQGTQVTVSS |
| S002-NB 151-36 | SEQ ID NO. 49 | QVQLVESGGGLVQAGGSLRLSCAASGLTFSYYGMGWFRQAPGKERE FVAAINWSGTSTYYADSVKDRFTVSRDNAKNTAYLHMNNLKPEDTAV YYCAARKYSSSQAMGLPNDIDYWGQGTQVTVSS |
| S002-NB 151-13 | SEQ ID NO. 51 | QVQLVESGGGLVQAGDSLRLSCAASTRIFRSYVMGWFRQAPGKERE AVASIRWSNDTGTYADSVKGRFTISRDNAKNTVYLQMNSLKPEDTAVY SCAADSPPWGRTWYTGYDYWGQGTQVTVSS |
| S002-NB 150-152n | SEQ ID NO. 53 | EVQVVESGGGLVQTGGSLRLSCAASGRPFDWLTVGWFRQAPGKER EFVAAISQSGGRIFYSDSVKGRFTISRDNAKNTAFLQMNSLKPEDTAV YSCAAQMRGYSRAAYPDEYDYWGQGTQVTVSS |
| S002-NB 150-159n | SEQ ID NO. 55 | QVQLVESGGGLVQAGDSLRLACEASGRTATISTMGWFRQAPGKERE FVGRIDWSAESTYIVDSVKGRFIISRDNAKNAGYLQMNSLKPVDTAVY YCAAIVVRERSYKYWGQGTQVTVSS |

TABLE 3

Specific nucleotide sequence information of the heavy chain variable region of the anti-CD22 antibody

| Antibody number | Sequence number | Heavy chain variable region sequence (VH) |
|---|---|---|
| S002-NB 150-42 | SEQ ID NO. 22 | CAGGTGCAGCTGGTGGAGAGCGGGGGGGGCCTGGTGCAGGCCG GCGACAGCCTGAAGCTGAGCTGCCTGGCCAGCGGCATCACCTTC AGCAGCTACTACATGAGCTGGTTCAGGCAGGCCCCCGGCAAGGA GAGGGAGTTCGTGGGGGGCGTGGGCAGGAGGGGCGCCCCCAGC CACCACGCCGACAGCGTGAAGGGCAGGTTCACCATCAGCAGGGA CAACGCCAAGAGCGCCGTGTACCTGCAGATGAACAGCCTGCAGC CCGAGGACACCGCCGTGTACTTCTGCGCCGCCAAGTGGATGGCC GCCAGCACCACCGTGGCCGACTACTGGGGCCAGGGCACCCAGG TGACCGTGAGCAGC |
| S002-N8 150-5 | SEQ ID NO. 24 | CAGCTGCAGCTGGTGGAGAGCGGGGGGGGCCTGGTGGAGGCCG GCGGCAGCCTGAGGCTGAGCTGCGTGGGCAGCGGCGACAGGGT GAGCATCGCCCTGATGGGCTGGTTCAGGCAGGCCCCCGGCAAG GAGAGGGAGTTCGTGGCCGCCATCAGCCCCAGCGGCGGCAGGA TCACCTAGAGCGACAGCGTGAAGGGCAGGTTCACCATCAGCAGG GAGAACGCCAAGAACACCGTGTACCTGCAGATGAACAGCCTGAA GAGGGACGACACCGCCGTGTACGTGTGCGCCGCCAACTTCAGGG GCTACCTGAGCAGCAGCAGGGGCAGCGACTACGCCTACTGGGG CCAGGGCACCCAGGTGACCGTGAGCAGC |
| S002-NB 150-40 | SEQ ID NO. 26 | CAGGTGCAGGTGGTGGAGAGGGGCGGCGGCCTGGTGCAGGAOG GCGGCAGCCTGAGGCTGAGCTGCGCCGCCAGCGGCCTGACCTT CAGCTTCTACAACATGGGCTGGTTCAGGCAGGCCCCCGGCAAGG AGAGGGAGTTCGTGGCCGCCATCAGCCAGAGCGGCCTGAGCAC CCACTACGCCGACAGCATGAAGGGCAGGTTCACCATCAGCAGGG ACAACGCCAAGAACACCGTGTACCTGCAGATGAACAGCCTGAACC CCGTGGACACCGCCGCCTACTACTGCGCCGCCGGCAGGAGGGG CTACCTGGCCAGCACCACCAACGACTACGAGTACTGGGGCCAGG GCACCCAGGTGACCGTGAGCAGC |
| S002-NB 150-57 | SEQ ID NO. 28 | CAGGTGCAGCTGGTGGAGAGCGGGGGGGGCCTGGTGCAGGCCG GCGACAGCCTGAGGCTGAGCTGCGCCGTGACCGGCAGGGCCTA CAGCAGGAGCGACATGGGCTGGTTCAGGCAGGCCCCCGGCAAG GAGAGGGAGATCGTGGCCGTGATCACCTTCGGCGGCGGCACCG ACTACGCCGACAGCGTGAAGGGGAGGTTCACCATCAGCAGCGAG GACACCAAGAACACCCTGTACCTGCAGATGAACAGCCTGCAGCC CGAGGACACCGCCGTGTACTACTGCGCCGCCGGCTTCAGGGGCA GCAGGTGGAGCACCGCCGCCAGGAGGAAGGAGGACGACTACGC CTTCTGGGGCCAGGGCACCCAGGTGACCGTGAGCAGC |
| S002-NB 150-2 | SEQ ID NO. 30 | CAGGTGCAGCTGGTGGAGAGCGGCGGCGGCCTGGTGCAGCCCG GCGGCAGCCTGAGGCTGAGCTGCGCCGCCAGCGGCAGCTGGTT CAACATCGCCATGGGCTGGTTCAGGCAGGCCCCCGGCAAGGAGA GGGAGTTCGTGGCCGGCATCAGGTGGAGCGACAGCAAGACCTAC TACGCCGACAGCGTGAAGGGCAGGTTCACCATCAGCGGCGACAA CGCCAAGAACACCACCTACCTGCAGATGAACAGCCTGAAGCCCG AGGACACCGCCGTGTACTACTGCGCCGCCCAGAGGTACTACAGG GGCAGCTACAACAGGCAGACCAACTACGACCACTGGGGCCAGGG CACCCAGGTGACCGTGAGCAGC |
| S002-NB 151-14 | SEQ ID NO. 32 | CAGGTGCAGCTGGTGGAGAGCGGCGGCGGCCTGGTGCAGGCCG GCGGCAGCCTGAGGCTGAGCTGCACCACCAGCGGCGGCACCCT GAGCAGGATCACCATGGGCTGGTTCAGGCAGGCCCCCGGCAAG GAGAGGGAGTTCGTGGCCGCCATCAAGTGGGGCGGCAGCAGCA CCCCCTACAGCGACAGCGTGAAGGGCAGGTTCACCATCAGCAGG GACAACGCCAAGAACACCGTGTACCTGCAGATGGACAGGCTGGT GCCCGAGGACACCGCCGTGTACTACTGCGCCGGCGGCCTGAGG GGCCCCTACAGCGACAGCGTGACCAGCAGCGTGCAGTACAACTA CTGGGGCCAGGGCACCCAGGTGACCGTGAGCAGC |
| S002-NB 151-51 | SEQ ID NO. 34 | CAGGTGCAGCTGGTGGAGAGCGGCGGCGGCCTGGTGCAGGCCG GCGGCAGCCTGAGGCTGAGCTGCGCCGCCAGCGGCATCACCAG CGACGACTACGCCATCGGCTGGTTCAGGCAGGCCCCCGGCAAG GAGAGGGAGGGCGTGAGCTGCATGTACAGCAGCGACGGCAGCA CCTACTACGCCGACAGCGTGAAGGGCAGGTTCACCATCAGCAGG GACAACGCCAAGAACACCGTGTACCTGCAGATGAACAGCCTGAG GCCCGAGGACACCGCCGTGTACCACTGCGCCGCCGGCCCCTGG TGCTTCGTGACCGGCGTGGGCAGGGAGGAGTGGGGCCAGGGCA CCCAGGTGACCGTGAGCAGC |
| S002-NB 151-2 | SEQ ID NO. 36 | CAGGTGCAGCTGGTGGAGAGCGGCGGCGGCCTGGTGCAGGCCG GCGACAGCCTGAGGCTGAGCTGCGCCGCCAGCGGCAGGACCTT CAGCCCCAGCACCATGGCCTGGTTCAGGCAGGCCCCCGGCAAG GAGAGGGAGCTGGTGGCCAGGATCGGCTGGACCTACGGCGACA |

TABLE 3-continued

| Antibody number | Sequence number | Heavy chain variable region sequence (VH) |
|---|---|---|
| Specific nucleotide sequence information of the heavy chain variable region of the anti-CD22 antibody | | |
| | | CCTACTACGTGGACAGCGCCAAGGGCAGGTTCACCATCAGCATG GACAACGTGAAGAACACCGTGTACCTGCAGATGAACAGCCTGAA GCCCGAGGACACCGCCGTGTACTACTGCGCCGCCCTGTTCAGGG GCGGCCTGAGCTACAACTTCAGCAACAGGGGCACCCAGGTGACC GTGAGCAGC |
| S002-NB 151-82 | SEQ ID NO. 38 | GAGGTGCAGGTGGTGGAGAGCGGCGGCGGCCTGGTGCAGGCCG GCGACAGCCTGAGGCTGAGCTGCACCACCAGCGGCAGGACCTTC TACGGCGACTACATCGCCTGGTTCAGGCAGGCCCCCGGCAAGGA GAGGGAGTTCGTGGCCGCCATCGCCGTGAGGGGCAGGGGCACC TTCTACGGCGACAGCGTGAAGGGCAGGTTCACCATCAGCAGGGA CAACGCCGAGAACACCCTGAGCCTGCAGATGAACAGCCTGAAGC CCGAGGACACCGCCGTGTACTACTGCGCCGCCGACGCCGGCAG CTACGCCAGCAGGGGCTTCCCCGTGAGGGAGACCGGCAGGTAC GACTACTGGGGCCAGGGCACCCAGGTGACCGTGAGCAGC |
| S002-NB 151-23 | SEQ ID NO. 40 | CAGGTGCAGCTGGTGGAGAGCGGCGGCGGCCTGGTGCAGGCCG GCGGCAGCCTGACCGTGAGCTGCACCAACAGCGGCAGGACCCT GAGCACCAGCACCATCGCCTGGTTCAGGCAGAAGCCCGGCAAGG ACAGCGAGTTCGTGGCCGCCATCAGGTGGAGCGGCGGCATGGG CTGGTACGCCGACAGCGTGAAGGGCAGGTTCACCATCAGCAGGG ACAACGCCGAGAACACCGTGAGCCTGCAGATGAACACCCTGCAG CCCGAGGACACCGCCGTGTACTTCTGCGCCGTGAGCACCGTGCC CTACTACGGCAGCATCTACACCAGGGTGGGCGACTACCCCTACT GGGGCCAGGGCACCCAGGTGACCGTGAGCAGC |
| S002-NB 151-66 | SEQ ID NO. 42 | CAGGTGCAGCTGGTGGAGAGCGGCGGCGGCCTGGTGCAGGCCG GCGGCAGCCTGAGGCTGGCCTGCGCCGCCAGCGGCGACACCGT GAGCATCTACTACATGGGCTGGTTCAGGCAGGCCCCCGGCAAGG AGAGGGAGTTCGTGGGCGCCCTGAGCGCCAGCGGCCAGTTCAC CGACCACGCCGACAGCGTGAAGGGCAGGTTCACCATCAGCAGGG ACGACGCCCAGAACACCGTGTTCCTGCACATGAACGACCTGAAG CCCGAGGACACCGCCGTGTACTACTGCGCCGTGCAGAGGTACGG CTGGGTGTACAGGACCGACAAGACCATGTACAACTACTGGGGCC AGGGCACCCAGGTGACCGTGAGCAGC |
| S002-NB 151-92 | SEQ ID NO. 44 | CAGGTGCAGCTGGTGGAGAGCGGCGGCGGCCTGGTGCAGAGCG GCGGCAGCCTGAGGCTGAGCTGCGCCGCCAGCGGCTTCACCTTC AGCGACTACACCATGAACTGGGTGAGGCAGGCCCCCGGCAAGG GCCTGGAGTGGGTGAGCGAGATCAGCAGCGGCGGCCACTTCAA GAGCAACGCCGACAGCGTGAAGGACAGGTTCACCATCAGCAGGG ACAACGCCAAGAACACCCTGTACCTGCAGATGAACAGCCTGAAGC CCGAGGACACCGCCGTGTACTTCTGCGCCAAGTGCCCCAGGCCC AGCGTGTACTGCAGGGACTACGAGAGCACCAGCCTGTACAGGGG CCAGGGCACCCAGGTGACCGTGAGCAGC |
| S002-NB 151-64 | SEQ ID NO. 46 | CAGGTGCAGCTGGTGGAGAGCGGCGGCGGCCTGGTGCAGCCCG GCGGCAGCCTGACCCTGAGCTGCGCCGCCAGCGGCTTCGACTTC AGCTTCTACACCATGACCTGGGTGAGGCAGGCCCAGGGCAAGGG CCTGGAGTGGGTGAGCACCATCAGCACCGGCGGCGGCGGCAGC AACTACGCCGACAGCGTGAAGGGCAGGTTCACCATCAGCAGGGA CAACGCCAAGAAGACCCTGTACCTGCAGATGACCAGCCTGAAGC CCGAGGACACCGCCGTGTACTACTGCGCCAGCCACAGGAGGGG CTACATGTTCGTGAGCAGCAGGAAGAACGAGTACGACTACTGGG GCAGGGGCACCCAGGTGACCGTGAGCAGC |
| S002-NB 151-30 | SEQ ID NO. 48 | CAGGTGCAGCTGGTGGAGAGCGGCGGCGGCCTGGTGCAGGCCG GCGGCAGCCTGAGGCTGAGCTGCGCCGCCAGCGGCAGGGCCAG CGGCAGCGGCGCCATGGGCTGGTTCAGGCAGGCCCCCGGCCAG GAGAGGAGGTTCGTGGCCGGCATCGAGTGGAGCAGCGGCGGCC CCGTGTACGCCGACAGCGTGAAGGGCAGGTTCACCCTGAGCAGG GACAACGCCAAGAACACCGTGCACCTGCAGATGAACAGCCTGAA GCCCGAGGACACCGCCGTGTACTACTGCGCCGCCGCCCCCTGG GTGTTCAGCAGCCCCGACGACTACATGTACTGGGGCCAGGGCAC CCAGGTGACCGTGAGCAGC |
| S002-NB 151-36 | SEQ ID NO. 50 | CAGGTGCAGCTGGTGGAGAGCGGCGGCGGCCTGGTGCAGGCCG GCGGCAGCCTGAGGCTGAGCTGCGCCGCCAGCGGCCTGACCTT CAGCTACTACGGCATGGGCTGGTTCAGGCAGGCCCCCGGCAAGG AGAGGGAGTTCGTGGCCGCCATCAACTGGAGCGGCACCAGCACC TACTACGCCGACAGCGTGAAGGACAGGTTCACCGTGAGCAGGGA CAACGCCAAGAACACCGCCTACCTGCACATGAACAACCTGAAGCC |

TABLE 3-continued

Specific nucleotide sequence information of the heavy chain variable region of the anti-CD22 antibody

| Antibody number | Sequence number | Heavy chain variable region sequence (VH) |
|---|---|---|
| | | CGAGGACACCGCCGTGTACTACTGCGCCGCCAGGAAGTACAGCA GCAGCCAGGCCATGGGCCTGCCCAACGACATCGACTACTGGGGC CAGGGCACCCAGGTGACCGTGAGCAGC |
| S002-NB 151-13 | SEQ ID NO. 52 | CAGGTGCAGCTGGTGGAGAGCGGCGGCGGCCTGGTGCAGGCCG GCGACAGCCTGAGGCTGAGCTGCGCCGCCAGCACCAGGATCTTC AGGAGCTACGTGATGGGCTGGTTCAGGCAGGCCCCCGGCAAGG AGAGGGAGGCCGTGGCCAGCATCAGGTGGAGCAACGACACCGG CACCTACGCCGACAGCGTGAAGGGCAGGTTCACCATCAGCAGGG ACAACGCCAAGAACACCGTGTACCTGCAGATGAACAGCCTGAAG CCCGAGGACACCGCCGTGTACAGCTGCGCCGCCGACAGCCCCC CCTGGGGCAGGACCTGGTACACCGGCTACGACTACTGGGGCCAG GGCACCCAGGTGACCGTGAGCAGC |
| S002-NB 150-152n | SEQ ID NO. 54 | GAGGTGCAGGTGGTGGAGAGCGGCGGCGGCCTGGTGCAGACCG GCGGCAGCCTGAGGCTGAGCTGCGCCGCCAGCGGCAGGCCCTT CGACTGGCTGACCGTGGGCTGGTTCAGGCAGGCCCCCGGCAAG GAGAGGGAGTTCGTGGCCGCCATCAGCCAGAGCGGCGGCAGGA TCTTCTACAGCGACAGCGTGAAGGGCAGGTTCACCATCAGCAGG GACAACGCCAAGAACACCGCCTTCCTGCAGATGAACAGCCTGAA GCCCGAGGACACCGCCGTGTACAGCTGCGCCGCCCAGATGAGG GGCTACAGCAGGGCCGCCTACCCCGACGAGTACGACTACTGGGG CCAGGGCACCCAGGTGACCGTGAGCAGC |
| S002-NB 150-159n | SEQ ID NO. 56 | CAGGTGCAGCTGGTGGAGAGCGGCGGCGGCCTGGTGCAGGCCG GCGACAGCCTGAGGCTGGCCTGCGAGGCCAGCGGCAGGACCGC CACCATCAGCACCATGGGCTGGTTCAGGCAGGCCCCCGGCAAGG AGAGGGAGTTCGTGGGCAGGATCGACTGGAGCGCCGAGAGCAC CTACATCGTGGACAGCGTGAAGGGCAGGTTCATCATCAGCAGGG ACAACGCCAAGAACGCCGGCTACCTGCAGATGAACAGCCTGAAG CCCGTGGACACCGCCGTGTACTACTGCGCCGCCATCGTGGTGAG GGAGAGGAGCTACAAGTACTGGGGCCAGGGCACCCAGGTGACC GTGAGCAGC |

TABLE 4

Specific sequence information of CDRs of CD22 nanobody analyzed by IMGT, KABAT and Chothia software IMGT analysis

| Antibody number | Sequence number | CDR1 | Sequence mimber | CDR2 | Sequence number | CDR3 |
|---|---|---|---|---|---|---|
| S002-NB 150-42 | SEQ ID NO. 37 | GITFSSYY | SEQ ID NO. 58 | VGRSGAPS | SEQ ID NO. 59 | AAKWMAAST TVADY |
| S002-NB 150-5 | SEQ ID NO. 66 | GDRVSIAL | SEQ ID NO. 67 | ISPSGGRI | SEQ ID NO. 68 | AANFRGYLSS SRGSDYAY |
| S002-NB 150-40 | SEQ ID NO. 75 | GLIFSFYN | SEQ ID NO. 76 | ISQSGLST | SEQ ID NO. 77 | AAGRRGYLAS TTNDYEY |
| S002-NB 150-57 | SEQ ID NO. 84 | GRAYSRSD | SEQ ID NO. 85 | ITFGGGT | SEQ ID NO. 86 | AAGFRGSRWS TAARRKEDDY AF |
| S002-NB 150-2 | SEQ ID NO. 93 | GSWENIA | SEQ ID NO. 94 | IRWSDSKT | SEQ ID NO. 95 | AAQRYYRGSY NRQTNYDH |
| S002-NB 151-14 | SEQ ID NO. 102 | GGILSRIT | SEQ ID NO. 103 | IKWGGSST | SEQ ID NO. 104 | AGGLRGPYSD SVTSSVWYNY |
| S002-NB 151-51 | SEQ ID NO. 111 | GITSDDYA | SEQ ID NO. 112 | MYSSDGST | SEQ ID NO. 113 | AAGPWCEVYG VGREE |
| S002-NB 151-2 | SEQ ID NO. 120 | GRTFSPST | SEQ ID NO. 121 | IGWTYGDT | SEQ ID NO. 122 | AALFRGGLSY NP |

TABLE 4-continued

Specific sequence information of CDRs of CD22 nanobody analyzed by IMGT, KABAT and Chothia software

| | | | | | | |
|---|---|---|---|---|---|---|
| S002-NB 151-82 | SEQ ID NO. 29 | GRTFYGDY | SEQ ID NO. 130 | IAVRGRGT | SEQ ID NO. 131 | AADAGSYASR GFPVRETGRY DY |
| S002-NB 151-23 | SEQ ID NO. 138 | GRTLSTST | SEQ ID NO. 139 | IRWSGGMG | SEQ ID NO. 140 | AVSTVPYYGSI YTRVGDYPY |
| S002-NB 151-66 | SEQ ID NO. 147 | GDTVSIYY | SEQ ID NO. 148 | LSASGQFT | SEQ ID NO. 149 | AVQRYGWVY RTDKTMYNY |
| S002-NB 151-92 | SEQ ID NO. 156 | GFTESDYT | SEQ ID NO. 157 | ISSGGHFK | SEQ ID NO. 158 | AKCPRPSVYC RDYESTSLY |
| 8002-NB 151-64 | SEQ ID NO. 165 | GFDFSFYT | SEQ ID NO. 166 | ISTGGGGS | SEQ ID NO. 167 | ASHRRGYMFV SSRKNEYDY |
| S002-NB 151-30 | SEQ ID NO. 174 | GRASGSGA | SEQ ID NO. 175 | IEWSSGGP | SEQ ID NO. 176 | AAAPWVFSSP DDYMY |
| S002-NB 151-36 | SEQ ID NO. 183 | GLTFSYYG | SEQ ID NO. 184 | INWSGTST | SEQ ID NO. 185 | AARKYSSSQA MGLPNDIDY |
| SO02-NB 151-13 | SEQ ID NO. 192 | TRIFRSYV | SEQ ID NO. 193 | IRWSNDTG | SEQ ID NO. 194 | AADSPPWGRT WYTGYDY |
| S002-NB 150-152n | SEQ ID NO. 201 | GRPFDWLT | SEQ ID NO. 202 | ISQSGGRI | SEQ ID NO. 203 | AAQMRGYSR AAYPDEYDY |
| S002-NB 150-1590 | SEQ ID NO. 210 | GRTATIST | SEQ ID NO. 211 | IDWSAEST | SEQ ID NO. 212 | AAIVVRERSY KY |

Kabat analysis

| Antibody povober | Sequence number | CDR1 | Sequence number | CDR2 | Sequence number | CDR3 |
|---|---|---|---|---|---|---|
| S002-NB 150-42 | SEQ ID NO. 60 | SYYMS | SEQ ID NO. 61 | GVGRSGAPSHHA DSVKG | SEQ ID NO. 62 | KWMAASTTV ADY |
| S002-NB 150-5 | SEQ ID NO. 69 | IALMG | SEQ ID NO. 70 | AISPSGGRITYSDS VKG | SEQ ID NO. 71 | NFRGYLSSSRG SDYAY |
| S002-NB 150-40 | SEQ ID NO. 78 | FYNMG | SEQ ID NO. 79 | AISQSGLSTHYAD SMKG | SEQ ID NO. 80 | GRRGYLASTI NDYEY |
| S002-NB. 150-57 | SEQ ID NO. 87 | RSDMG | SEQ ID NO. 88 | VITFGGGTDYADS VKG | SEQ ID NO. 89 | GFRGSRWSTA ARRKEDDYAF |
| S002-NB 150-2 | SEQ ID NO. 96 | IAMG | SEQ ID NO. 97 | GIRWSDSKTYYA DSVKG | SEQ ID NO. 98 | QRYYRGSYNR QTNYDH |
| S002-NB 151-14 | SEQ ID NO. 105 | RITMG | SEQ ID NO. 106 | AIKWGGSSTPYS DSVKG | SEQ ID NO. 107 | GLRGPYSDSV TSSVQYNY |
| S002-NB 151-51 | SEQ ID NO. 114 | DYAIG | SEQ ID NO. 115 | CMYSSDGSTYYA DSVKG | SEQ ID NO. 116 | GPWCFVTGVG REE |
| S002-NB 151-2 | SEQ ID NO. 123 | PSTMA | SEQ ID NO. 124 | RIGWTYGDTYYV DSAKG | SEQ ID NO. 125 | LFRGGLSYNF |
| S002-NB 151-82 | SEQ ID NO. 132 | GDYIA | SEQ ID NO. 133 | AIAVRGRGTFYG DSVKG | SEQ ID NO. 134 | DAGSYASRGF PVRETGRYDY |
| S002-NB 151-23 | SEQ ID NO. 141 | TSTIA | SEQ ID NO. 142 | AIRWSGGMGWY ADSVKG | SEQ ID NO. 143 | STVPYYGSIYT RVGDYPY |
| S002-NB 151-66 | SEQ ID NO. 156 | IYYMG | SEQ ID NO. 151 | ALSASGQFTDHA DSVKG | SEQ ID NO. 152 | QRYGWVYRT DKTMYNY |
| S002-NB 151-92 | SEQ ID NO. 159 | DYTMN | SEQ ID NO. 160 | EISSGGHFKSNAD SVKD | SEQ ID NO. 161 | CPRPSVYCRD YESTSLY |
| S002-NB 151.64 | SEQ ID NO. 168 | FYTMT | SEQ ID NO. 169 | TISTGGGGSNYAD SVKG | SEQ ID NO. 170 | HRRGYMFVSS RKNEYDY |

TABLE 4-continued

Specific sequence information of CDRs of CD22 nanobody analyzed by IMGT, KABAT and Chothia software

| | | | | | | |
|---|---|---|---|---|---|---|
| S002-NB 151-30 | SEQ ID NO. 177 | SGAMG | SEQ ID NO. 178 | GIEWSSGGPVYA DSVKG | SEQ ID NO. 179 | APWVFSSPDD YMY |
| S002-NB 151-36 | SEQ ID NO. 186 | YYGMG | SEQ ID NO. 187 | AINWSGTSTYYA DSVKD | SEQ ID NO. 188 | RKYSSSQAMG LPNDIDY |
| S002-NB 151-13 | SEQ ID NO: 195 | SYVMG | SEQ ID NO. 196 | SIRWSNDTGTYA DSVKG | SEQ ID NO. 197 | DSPPWGRTWY TGYDY |
| S002-NB 150-152n | SEQ ID NO. 204 | WLTVG | SEQ ID NO. 205 | AISQSGGRIFYSD SVKG | SEQ ID NO. 206 | QMRGYSRAAY PDEYDY |
| S002-NB 150-159n | SEQ ID NO. 213 | ISTMG | SEQ ID NO. 214 | RIDWSAESTYTVD SVKG | SEQ ID NO. 215 | IVVRERSYKY |

Chothia analysis

| Antibody number | Sequence number | CDR1 | Sequence number | CDR2 | Sequence number | CDR3 |
|---|---|---|---|---|---|---|
| S002-NB 150-42 | SEQ ID NO. 63 | GITFSSY | SEQ ID NO. 64 | GRSGAP | SEQ ID NO. 63 | KWMAASTTV ADY |
| S002-NB 150.5 | SEQ ID NO. 72 | GDRVSIA | SEQ ID NO. 73 | SPSGGR | SEQ ID NO. 74 | NFRGYLSSSRG SDYAY |
| $002-NB 150-40 | SEQ ID NO. 81 | GLTFSFY | SEQ ID NO. 82 | SQSGLS | SEQ ID NO. 83 | GRRGYLASTT NDYEY |
| S002-NB 150-57 | SEQ ID NO. 90 | GRAYSRS | SEQ ID NO. 91 | TFGGG | SEQ ID NO. 92 | GFRGSRWSTA ARRKEDDYAF |
| 6002-NB 150-2 | SEQ ID NO. 99 | GSWFNI | SEQ ID NO. 100 | RWSDSK | SEQ ID NO. 101 | QRYYRGSYNR QTNYDH |
| S002-NB 151-14 | SEQ ID NO. 108 | GGTLSRI | SEQ ID NO. 109 | KWGGSS | SEQ ID NO. 110 | GLRGPYSDSV TSSVQYNY |
| S002-NB 151-51 | SEQ ID NO .117 | GITSDDY | SEQ ID NO. 118 | YSSDGS | SEQ ID NO. 119 | GPWCFVTGVG REE |
| 6002-NB 151-2 | SEQ ID NO. 126 | GRTFSPS | SEQ ID NO. 127 | GWTYGD | SEQ ID NO. 128 | LFRGGLSYNF |
| S002-NB 151-82 | SEQ ID NO. 135 | GRTFYGD | SEQ ID NO. 136 | AVRGRG | SEQ ID NO. 137 | DAGSYASRGP PVRETGRYDY |
| $002-NB 151-23 | SEQ ID NO. 144 | GRTLSTS | SEQ ID NO. 145 | RWSGGM | SEQ ID NO. 146 | STVPYYGSIYT RVGDYPY |
| S002-NB 151-66 | SEQ ID NO. 153 | GDTVSIY | SEQ ID NO. 154 | SASGQP | SEQ ID NO. 155 | QRYGWVYRT DKTMYNY |
| S002-NB 161-92 | SEQ ID NO. 162 | GFTFSDY | SEQ ID NO. 163 | SSGGHF | SEQ ID NO. 164 | CPRPSVYCRD YESTSLY |
| S002-NB 151-64 | SEQ ID NO. 171 | GFDFSFY | SEQ ID NO. 172 | STGGGG | SEQ ID NO. 173 | HRRGYMFVSS RKNEYDY |
| S002-NB 151-30 | SEQ ID NO. 180 | GRASGSG | SEQ ID NO. 181 | EWSSGG | SEQ ID NO. 182 | APWVFSSPDD YMY |
| 6002-NB 161-36 | SEQ ID NO. 189 | GLTFSVY | SEQ ID NO. 190 | NWSGTS | SEQ ID NO. 191 | RKYSSSQAMG LPNDIDY |
| S002-NB 151-13 | SEQ ID NO. 198 | TRIFRSY | SEQ ID NO. 199 | RWSNDT | SEQ ID NO. 200 | DSPPWGRTWY TGYDY |
| S002-NB 150-152n | SEQ ID NO. 207 | GRPFDWL | SEQ ID NO. 208 | SQSGGR | SEQ ID NO. 209 | QMRGYSRAAY PDEYDY |
| S002-NB 150-159n | SEQ ID NO. 216 | GRTATIS | SEQ ID NO. 217 | DWSAES | SEQ ID NO. 218 | IVVRERSYKY |

Example 2 Preparation of VHH Antibody, Control Antibody, Polyclonal Antibody Serum and CD22 Protein 2.1 Expression and Purification of VHH Antibody The VHH variable region sequence was recombined into the expression vector BI3.4-huIgG1 containing a signal peptide and human IgG1 Fc (the human IgG1 Fc sequence was shown in SEQ ID NO: 14, the hinge region sequence was shown in SEQ ID NO: 15) by Taizhou Biointron Biotechnology Co., Ltd, and plasmids were prepared according to the established standard molecular biology methods. For the specific method, see Sambrook, J., Fritsch, E. F., and Maniatis, T. (1989). Molecular Cloning: A Laboratory Manual, Second Edition (Plainview, New York: Cold Spring Harbor Laboratory Press). The expression vector was transiently transfected into HEK293E cells (purchased from Suzhou Yiyan Biotechnology Co., Ltd.) according to the instructions of PEI (purchased from Polysciences, catalog number: 24765-1), and the transfected cells were continuously cultured at 37° C. for 5 days using FreeStyle™ 293 (Thermo Fisher Scientific, catalog number: 12338018), and the cell components were removed by centrifugation to obtain the culture supernatant containing the VHH antibody. The culture supernatant was loaded onto the protein A chromatography column (the protein A filler AT Protein A Diamond and the chromatography column BXK 16/26 were both purchased from Bestchrom (Shanghai) Biosciences Ltd., and the catalog numbers were: AA0273 and B-1620, respectively), the column was washed with PBS phosphate buffer (pH 7.4), then washed with 20 mM PB, 1M NaCl (pH 7.2), and finally eluted with citric acid buffer (pH 3.4). The antibody with Fc label eluted from the protein A chromatography column was collected, neutralized with 1/10 volume of 1M Tris (pH 8.0), and dialyzed with PBS at 4° C. overnight, and the dialyzed protein was aseptically filtered by 0.22 micron filter membrane and then subpackaged for storage at −80° C.

SEQ ID NO: 14 Sequence of human IgG1 Fc:
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

SEQ ID NO: 15 Hinge region sequence:
EPKSADKTHTCPPCP

2.2 Preparation of Control Antibody

The CD22 protein has 7 IgG-like domains outside the cell, in which domain 1 is located at the farthest end from the membrane and domain 7 is located at the nearest end from the membrane. HA22, m971 and hL22 are antibodies that recognize human CD22, wherein the antigen-binding epitopes of HA22 and hL22 are located in domain 2-3, and the antigen-binding epitope of m971 is located in domain 5-7. The heavy chain variable region and light chain variable region sequences of HA22 were obtained according to U.S. Pat. No. 9,580,461 B (which is incorporated herein by reference), the heavy chain variable region and light chain variable region sequences of m971 were obtained according to U.S. Pat. No. 8,591,889 B (which is incorporated herein by reference), and the heavy chain variable region and light chain variable region amino acid sequences of hL22 were obtained according to U.S. Pat. No. 5,789,554 B (which is incorporated herein by reference). The VH and VL of the antibody HA22, m971 and hL22 that recognize human CD22 and the human IgG1 Fc were linked in order from the N-terminal to the C-terminal, wherein the VH and VL were linked by three GGGGS linkers to form scFv-hFc, and the corresponding amino acid sequence information was shown in Table 5 below. The corresponding nucleotide sequences were respectively cloned into the pTT5 vector by GENERAL Biosystems (Anhui) Corporation Limited and expressed in HEK293E cells (purchased from Suzhou Yiyan Biotechnology Co., Ltd.) and purified according to the method of Example 2.1.

TABLE 5

Specific sequence information of VH and VL of anti-human CD22 antibody HA22, m971 and hL22 and human IgG1 Fc and scFv-hFc formed thereby

| Designation of sequence | Sequence number | Amino acid sequence |
|---|---|---|
| HA22 VH | SEQ ID NO: 5 | EVQLVESGGGLVKPGGSLKLSCAASGFAFSIYDMSWVRQTPEKCL EWVAYISSGGGTTYYPDTVKGRFTISRDNAKNTLYLQMSSLKSEDT AMYYCARHSGYGTHWGVLFAYWGQGTLVTVSA |
| HA22 VL | SBO ID NO: 6 | DIQMTQTTSSLSASLGDRVTISCRASQDISNYLNWYQQKPDGVKL LIYYTSILHSGVPSRFSGSGSGTDYSLTISNLEQEDFATYFCQGNTL PWTFGCGTKLEIK |
| HA22 scFv-hFc | SEQ ID NO: 7 | EVQLVESGGGLVKPGGSLKLSCAASGFAPSIYDMSWVRQTPEKCL EWVAYISSGGGTTYYPDTVKGRFTISRDNAKNTLYLQMSSLKSEDT AMYYCARHSGYGTHWGVLFAYWGQGTLVTVSAGGGGSGGGGSG GGGSDIQMTQTTSSLSASLGDRVTISCRASQDISNYLNWYQQKPDG TVKLLIYYTSILHSGVPSRFSGSGSGTDYSLTISNLEQEDFATYFCQQ GNTLPWTFGCGTKLEIKEPKSADKTHTCPPCPAPELLGGPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIEK TISKAKGQPREPQVYTLPPSREEMTKNQVSLTCLVKGFYPSDIAVE WESNGQPENNYKTTPPVLDSDGSFFLYSKLTVDKSRWQQGNVFSC SVMHEALHNHYTQKSLSLSPGK |

TABLE 5-continued

Specific sequence information of VH and VL of anti-human CD22 antibody HA22, m971 and hL22 and human IgG1 Fc and scFv-hFc formed thereby

| Designation of sequence | Sequence number | Amino acid sequence |
|---|---|---|
| m971 VH | SEQ ID NO: 8 | QVQLQQSGPGLVKPSQTLSLTCAISGDSVSSNSAAWNWIRQSPSRG LEWLGRTYYRSKWYNDYAVSVKSRITINPDTSKNQFSLQLNSVTPE DTAVYYCAREVTGDLEDAFDIWGQGTMVTVSS |
| In971 VL | SEQ ID NO: 9 | DIQMTQSPSSLSASVGDRVTITCRASQTIWSYLNWYQQRPGKAPNL LIYAASSLQSGVPSRFSGRGSGTDFTLTISSLQAEDFATYYCQQSYSI PQTPGQGTKLEIK |
| m971 scFv-hFc | SEQ ID NO: 10 | QVQLQQSGPGLVKPSQTLSLTCAISGDSVSSNSAAWNWIRQSPSRG LEWLGRTYYRSKWYNDYAVSVKSRITINPDTSKNQFSLQLNSVTPE DTAVYYCAREVTGDLEDAFDIWGQGTMVTVSSGGGGSGGGGSGG GGSDIQMTQSPSSLSASVGDRVTITCRASQTIWSYLNWYQORPGK APNLLIYAASSLQSGVPSRFSGRGSGTDFTLTISSLQAEDFATYYCQ QSYSIPQTFGQGTKLEIKEPKSADKTHTCPPCPAPELLGGPSVFLFPP KPKDTLMISRTPEVTCVVVDVSHEDPEVKFNWYVDQVEVHNAKT KPREEQYNSTYRVVSVLTVLHQDWLNGKEYKCKVSNKALPAPIEK TISKAKGQPREPQVYTLPPSREEMTKNQVSLTCLVKGFYPSDIAVE WESNGQPENNYKTTPPVLDSDGSFFLYSKLTVDESRWQQGNVFSC SVMHEALHNHYTQKSLSLSPGK |
| hL22 VH | SEQ ID NO: 11 | QVQLQQSGAEVKKPGSSVKVSCKASGYTFTSYWLHWVR QAPGQGLEWIGYINPRNDYTEY NQNFKDKATITADESTNTAYMELSSLRSEDTAFYFCARRDI TTFYWGQGTTVTVSS |
| hL22 VL | SEQ ID NO: 12 | DIQLTQSPSSLSASYGDRVTMSCKSSQSVLYSANHKNYLA WYQQKPGKAPKLLIYWASTR ESGVPSRFSGSGSGTDFTFTISSLQPEDIATYYCHQYLSSW TFGGGTKLEIK |
| HL22 scFv-Fc | SEQ ID NO: 13 | QVQLQOSGAEVKKPGSSVKVSCKASGYTFTSYWLHWVR QAPGQGLEWIGYINPRNDYTEY NQNFKDKATITADESTNTAYMELSSLRSEDTAFYFCARRDI TTFYWGQGTTVTVSSGGGGGGGGSGGGGSDIQLTQSPSS LSASVGDRVTMSCKSSQSVLYSANHKNYLAWYQQKPGK APKLLIYWASTR ESGVPSRESGSGSGTDFTFTISSLQPEDIATYYCHQYLSSW TFGGGTKLEIKEPKSADKTHTCPPCPAPELLGGPSVFLFPPKPKDT LMISKTPEVTCVVVDVSHEDPEVKFNWYVDGVEVHNAKTKPREE QYNSTYRVVSVLTVLHQDWLNGKEYKCKVSNKALPAPIEKTISKA KGQPREPQVYTLPPSREEMTKNQVSLTCLVKGFYPSDIAVEWESNG QPENNYKTTPPVLDSDGSFFLYSKLTVDKSRWQQGNVFSCSVMHE ALHNHYTQKSLSLSPGK |

2.3 Preparation of Human CD22-His Tag Protein

Figure 2:
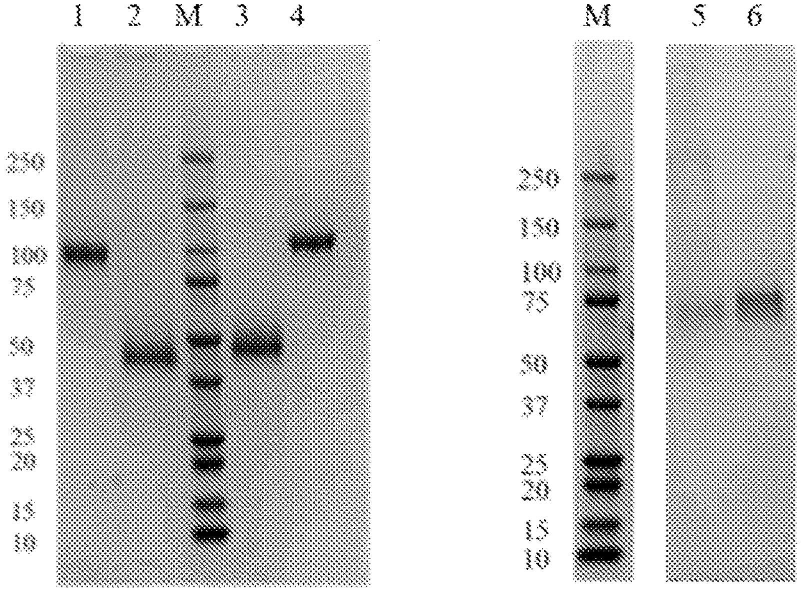
FIG. 2 shows the detection results of SDS-PAGE reducing and non-reducing gels of CD22-ECD-His, CD22 domain1-4-His and CD22 domain5-7-His protein samples. Lane 1 is the protein band of hCD22-ECD-His under non-reducing conditions, Lane 2 is the protein band of hCD22 domain5-7-His under non-reducing conditions, Lane 3 is the protein band of hCD22 domain5-7-His under reducing conditions, Lane 4 is the protein band of hCD22-ECD-His under reducing conditions, Lane 5 is the protein band of hCD22 domain1-4-His under non-reducing conditions, Lane 6 is the protein band of hCD22 domain1-4-His under reducing conditions, and Lane M is the protein maker band.
Figure 3A:
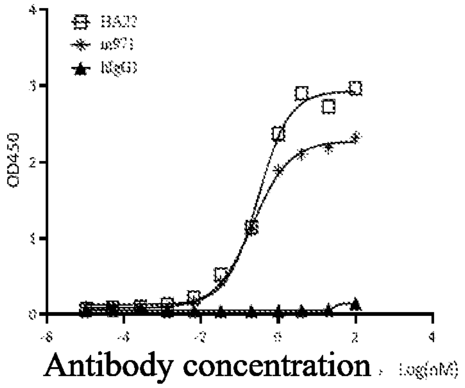
FIG. 3A shows the binding reaction of control antibody with human CD22-ECD-His protein detected by ELISA.
Figure 3B:
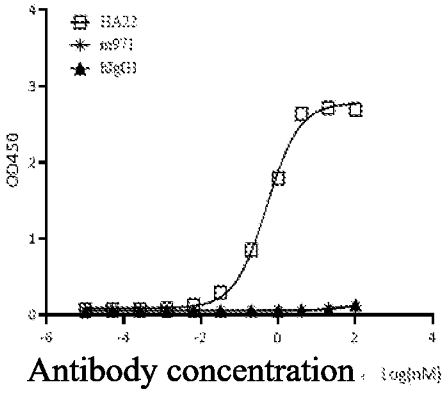
FIG. 3B shows the binding reaction of control antibody with human CD22 domain1-4-His protein detected by ELISA.
Figure 3C:
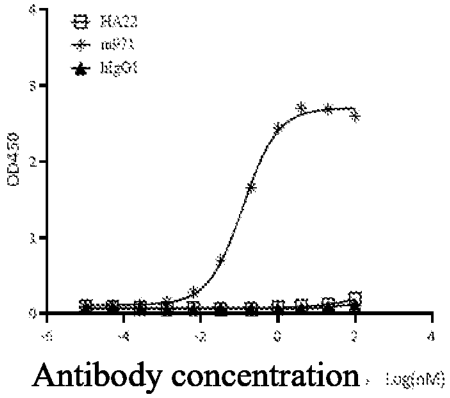
FIG. 3C shows the binding reaction of control antibody with human CD22 domain5-7-His protein detected by ELISA. The anti-CD22 control antibody is: HA22 and m971, the negative control is hIgG1.

The CD22 protein has 7 IgG-like domains outside the cell, in which domain 1 is located at the farthest end from the membrane and domain 7 is located at the nearest end from the membrane, the antigen-binding epitopes of HA22 and hL22 are located in domain 2-3, and the antigen-binding epitope of m971 is located in domain 5-7. The nucleotide sequences encoding the amino acid sequence of human CD22 protein (NCBI: NP_001762.2, SEQ ID NO: 1), the extracellular region (ECD, extra-cellular domain) amino acid sequence Asp 20-Arg 687 (SEQ ID NO: 2), the domain 1-4 Asp 20-Val 425 amino acid sequence (SEQ ID NO: 3) and the domain 5-7 Asp 414-Arg 687 amino acid sequence (SEQ ID NO: 4) were cloned into the pTT5 vector by GENERAL Biosystems (Anhui) Corporation Limited, respectively, and plasmids were prepared according to the established standard molecular biology methods. The corresponding amino acid sequence information was shown in Table 6 below. For the specific method, see Sambrook, J., Fritsch, E. F., and Maniatis, T. (1989). Molecular Cloning: A Laboratory Manual, Second Edition (Plainview, New York: Cold Spring Harbor Laboratory Press). HEK293E cells (purchased from Suzhou Yiyan Biotechnology Co., Ltd.) were transiently transfected (PEI, Polysciences, catalog number: 24765-1) and FreeStyle™293 (Thermofisher scientific, catalog number: 12338018) was used for scale-up culture at 37° C. After 6 days, the cell culture fluid was collected, centrifuged to remove cell components, and the culture supernatant containing the extracellular region of human CD22 protein was obtained. The culture supernatant was loaded onto a nickel ion affinity chromatography column HisTrap™ Excel (GE Healthcare, catalog number: GE17-3712-06), and the change in the ultraviolet absorbance (A280 nm) was monitored with an ultraviolet (UV) detector. After sample loading, the nickel ion affinity chromatography column was washed with 20 mM PB, 0.5M NaCl (pH 7.4) until the ultraviolet absorbance returned to the baseline, and then gradient elutions (2%, 4%, 8%, 16%, 50%, 100%) were performed with Buffer A: mM PB, 0.5M NaCl (pH 7.4) and Buffer B: 20 mM PB, 0.5M NaCl, and 500 mM imidazole. His-tagged human CD22 protein eluted from the nickel ion affinity chromatography column was collected and dialyzed against PBS phosphate buffer (pH 7.4) overnight in a refrigerator at 4° C. The dialyzed protein was aseptically filtered by 0.22 micron filter membrane and then subpackaged for storage at −80° C. to obtain purified human CD22 protein. The bands of interest of samples detected by SDS-PAGE reducing gel and non-reducing gel were shown in FIG. 2. The prepared CD22 protein described above was detected by ELISA using positive control antibodies that recognized different epitopes. The negative control antibody hIgG1 was anti-hel-hIgG1 (purchased from Biointron, catalog number: B117901) against chicken egg lysozyme. The detection results were shown in FIGS. 3A-3C. Both HA22 and m971 can bind to the human CD22-ECD-His protein, HA22 can bind to the human CD22 domain1-4-His protein, and m971 can bind to the human CD22 domain5-7-His protein. The detection results were consistent with the binding epitopes of HA22 and m971 reported in the literature, indicating that the protein with the above binding activity has been prepared and obtained.

TABLE 6

Amino acid sequences of human CD22 protein and extracellular region

| Designation of sequence | Sequence number | Amino acid sequence |
|---|---|---|
| Human CD22 protein | SEQ ID NO: 1 | MHLLGPWLLLLVLEYLAFSDSSKWVFHPETLYAWEGACVWIPCTYRALD GDLESFILFHNPEYNKNTSKFDGTRLYESTKDGKVPDEQRRVQFLGDKNKN CTLSIHPVHLNDSGQLGLRMESKTEKWMERIHLNVSERPFPHIQLPPEIQES QEVTLTCLLNFSCYGYPIQLQWLLEGVPMRQAAVTSTLTIKSVFTRSELKFS PQWSHHGKIVTCQLQDADGKFLSNDTVQLNVKHTPKLEIKVTPSDAIVREG DSVTMTCEVSSSNPEYTTVSWLKDGTSLKKQNTFTLNREVTKDQSGKYC CQVSNDVGPGRSEEVFLQVQYAPEPSTVQILHSPAVEGSQVEFLCMSLANPL PTNYTWYHNGKEMQGRTEEKVHIPKILPWHAGTYSCVAENILGTGQRGPG AELDVQYPPKKVTTVIQNPMPIREGDTVTLSCNYNSSNPSVTRYEWKPHGA WEEPSLGVLKIQNVGWDNTTIACAACNSWCSWASPVALNVQYAPRDVRVR KIKPLSEIHSGNSVSLQCDFSSSHPKEVQFFWEKNGRLLGKESQLNFDSISPE DAGSYSCWVNNSIGQTASKAWTLEVLYAPRRLRVSMSPGDQVMEGKSATL TCESDANPPVSHYTWFDWNNQSLPYHSQKLRLEPVKVQHSGAYWCQGTN SVGKGRSPLSTLTVYYSPETIGRRVAVGLGSCLAILILAICGLKLQRRWKRTQ SQQGLQENSSGQSFFVRNKKVRRAPLSEGPHSLGCYNPMMEDGISYTTLRF PEMNIPRTGDAESSEMQRPPPDCDDTVTYSALHKRQVGDYENVIPDFPEDE GIHYSELIQFGVGERPQAQENVDYVILKH |
| Human CD22 protein extracellular region | SEQ ID NO: 2 | DSSKWVFEHPETLYAWEGACVWIPCTYRALDGDLESFILFHNPEYNKNTSK FDGTRLYESTEDGKYPSEQKRVQFLGDKNKNCTLSIHPVHENDSGQLGLRM ESKTEKWMERIHLNVSERPFPPHIQLFPEIQESQEVTLTCLLNFSCYGYPIQL QWLLEGVPMRQAAVTSTSLTIKSVFTRSELKFSPQWSHHGKIVTCQLQDAD GKFLSNDTVQLNVKHTPKLEIKVTPSDAIVREGDSVTMTCEVSSSNPEYTTV SWLKDGTSLKKQNTFTLNLREVTKDQSGKYCCQVSNDNGPGRSEEVFLQV QYAPEPSTVQILHSPAVEGSQVEFLCMSLANPLPTNYTWYHNGKEMQGRTE EKVHIPKILPWHAGTYSCVAENILGTGQRGPGAELDVQYPPKKVTTVIQNP MPIREGDTVTLSCNYNSSNPSVTRYEWKPHGAWEEPSLGVLKIQNVGWDN TTIAVAACNSWCSWASPVALNVQYAPRDVRVRKIKPLSEHSGNSVSLQCDF SSSHPKEVQFFWEKNGRLLGKESQLNFDSISPEDAGDYCWVNNSIGQTASK AWTLEVLYAPRRLRVSMSPGDQVMEGKSATLTCESDANPPVSHYTWFDWN NQSLPYHSQKLRLEPVKVQHSGAYWCQGTNSVGKGRSPLSTLTVYYSPETI GRR |
| Human CD22 proteins domain1-4 | SEQ ID NO: 3 | DSSKWVFEHPETLYAWEGACVWIPCTYRALDGDLESFILFHNPEYNKNTSK FDGTRLYESTKDGKVPSEQKRVQFLGDKNKKNCTLSIHPVHLNDSGQLGLRM ESKTEKWMERIHLNVSERPFFPHIQLPPEIQESQEVTLTCLLNFSCYGYPIQL QWLLEGVPMRQAAVTSTSLTIKSVFTRSELFFSPQWSHHGKIVTCQLQDAD GKFLSNDTVQLNVKHTPKLEIKVTPSDAIVREGDSVTMTCEVSSSNPEYTTV SWLKDGTSLKKQNTFTLNLREVTKDQSGKYCCQVSNDVGPGRSEEVFLQV QYAPEPSTVQILHSPAVEGSQVEPLCMSLANPLPTNYTWYHNGKEMQGRTE EKVHIPKILPWHAGTYSCVAENILGTGQRGPGAELDVQYPPKKVTTV |
| Human CD22 protein domain5-7 | SEQ ID NO: 4 | DVQYPPKKVTTVIQNPMPIREGDTVTLSCNYNSSNPSVTRYEWKPHGAWEE PSLGLKIQNVGWDNTTIACAACNSWCSWASPVALNVQYAPRDVRVRKIK PLSEIHGNSVSLQCDFSSSHPKEVQFFWEKNGRLLGKESQLNFDSISPEDA GSYSCWVNNSIGQTASKAWTLEVLYAPRRLRVSMSPGDQVMEGKSATLTCE SDANPPVSHYTWFDWNNQSLPYHSQKLRLEPVKVQHSGAYWCQGTNSVG KGRSPLSTLTVYYSPETIGRR |

Figure 4A:
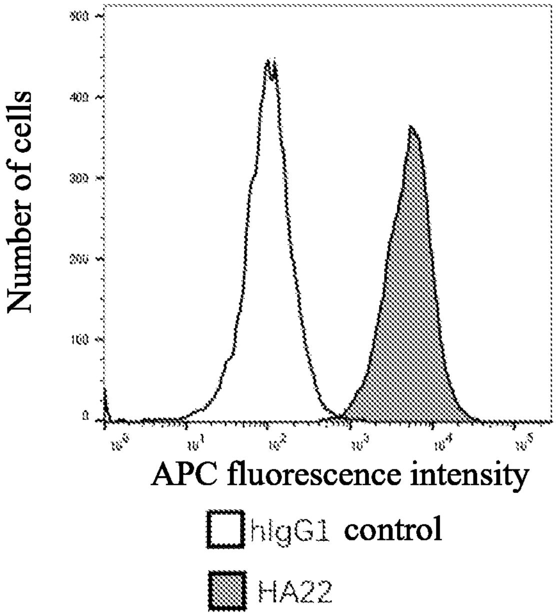
FIG. 4A is the FACS result of detecting CD22 expression quantity in Raji cells by HA22 antibody.
Figure 4B:
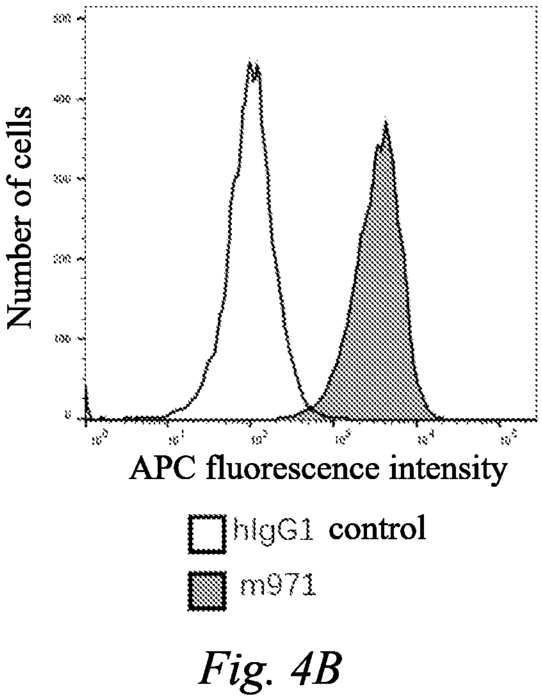
FIG. 4B shows the FACS result of detecting CD22 expression quantity in Raji cells by m971 antibody.

Example 3 Identification of Endogenous Expression Cell Line and Preparation of Overexpression Cell Line 3.1 Identification of Cell Line Expressing CD22 Endogenously Raji cells (purchased from China Center for Type Culture Collection, Wuhan University) were scale-up cultured in T-25 cell culture flasks to the logarithmic growth phase, the supernatant of the medium was discarded by centrifugation, and the cell pellet was washed 2 times with PBS. The HA22 and m971 antibodies were used as primary antibodies, APC-labeled secondary antibody (purchased from Biolegend, catalog number: 409306) was used and FACS (FACS Canto™, purchased from BD company) was used for detection and result analysis. The analysis results were shown in Table 7 and FIGS. 4A-4B, the Raji cells can bind to HA22 and m971.

TABLE 7

FACS detection results of the endogenous cell line Raji cells

| No. | Designation of antibody | Cell mean fluorescence density: IgG subtype control | Cell mean fluorescence density: CD22 antibody |
|---|---|---|---|
| 1 | HA22 | 158 | 6308 |
| 2 | m971 | 158 | 3955 |

3.2 Preparation of CHO-K1 Monoclonal Cell Line Stably Transfected with Human CD22

The nucleotide sequence encoding the full-length amino acid sequence of human CD22 (NCBI: NP_001762.2, SEQ ID NO: 1) was cloned into the pcDNA3.1 vector and a plasmid was prepared by GENERAL Biosystems (Anhui) Corporation Limited. Plasmid transfection (Lipofectamine® 3000Transfection Kit, purchased from Invitrogen, catalog number: L3000-015) was performed on CHO-K1 cell line (purchased from Shanghai Institutes for Biological Sciences, Chinese Academy of Sciences), and then the transfected cells were selectively incubated for 2 weeks in DMEM/F12 medium containing 10 μg/ml of puromycin and 10% (w/w) of fetal bovine serum. The FITC-labeled anti-CD22 antibody (Thermofisher scientific, catalog number: 11-0229-42) was used to sort the positive monoclonal cells into a 96-well plate on flow cytometer FACS Ariall (BD Biosciences) and the plate was placed in a cell incubator at 37° C. and 5% (v/v) $CO_2$ for cell culture. Some wells containing monoclonal cells were selected for amplification after approximately 2 weeks. The amplified clones were screened by flow cytometry. The monoclonal cell line with better growth and higher fluorescence intensity was selected for further scale-up culture and then freezed in liquid nitrogen.

The specific selection results were shown in Table 8 and FIG. 5, and the IgG subtype control was human IgG1 control. Table 8 showed that a series of CHO-K1 monoclonal cell lines positive for CD22 expression was prepared. In FIG. 5, the abscissa was the fluorescence intensity of cells, and the ordinate was the number of cells. The results in FIG. 5 indicated that CHO-K1-human CD22 2C4, CHO-K1-human CD22 1G5 and CHO-K1-human CD22 1D9 were cell lines with high expression of CD22.

TABLE 8

FACS detection results of CHO-K1 cell line stably transfected with human CD22 protein

| No. | Clone number of stably transfected cell line | Cell mean fluorescence intensity: IgG subtype control | Cell mean fluorescence intensity: CD22 antibody |
|---|---|---|---|
| 1 | CHO-K1-human CD22 2C4 | 66 | 4621 |
| 2 | CHO-K1-human CD22 1G5 | 66 | 3154 |
| 3 | CHO-K1-human CD22 1D9 | 66 | 2488 |

Example 4 Identification of VHH Antibody in Alpaca 4.1 Binding of VHH-Fc Antibodies to Human CD22 Protein Detected by Enzyme-Linked Immunosorbent Assay (ELISA)

Figure 6:
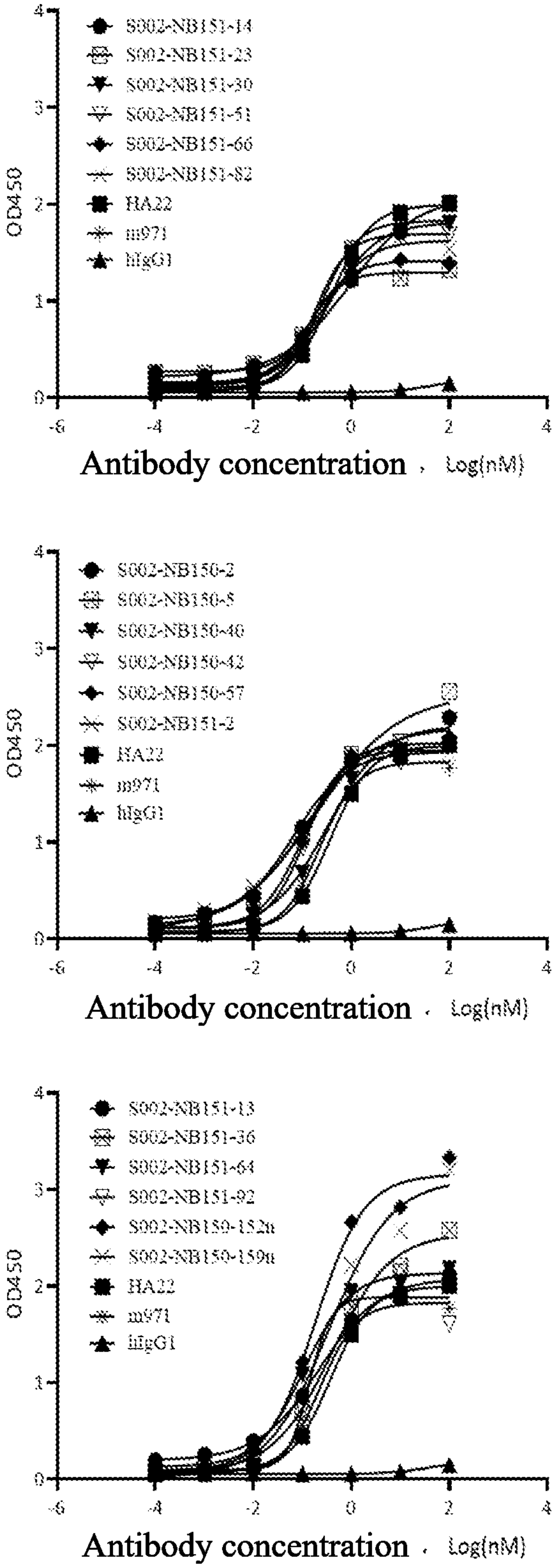
FIG. 6 shows the binding reaction of the VHH-Fc antibodies of the present invention with human CD22-ECD-His protein detected by ELISA. The anti-CD22 positive control antibody is: HA22 and m971, the negative control is hIgG1.

In order to detect the binding activity of VHH-Fc to human CD22 protein, the purified human CD22-ECD-His protein obtained in Example 2 was diluted with PBS to a final concentration of 2 μg/mL, and then added to 96-well ELISA plate at 100 μl/well. The plate was sealed with plastic film and incubated overnight at 4° C., the plate was washed 2 times with PBS the next day, and then a blocking solution [PBS+2% (w/w) BSA] was added for blocking at room temperature for 2 hours. The blocking solution was poured off, and 100 nM of serially diluted VHH-Fc antibody or negative control antibody was added at 50 μl/well. After incubation at 37° C. for 2 hours, the plate was washed 3 times with PBS. HRP (horseradish peroxidase)-labeled secondary antibody (purchased from Sigma, catalog number: A0170) was added, and incubated at 37° C. for 2 hours, and the plate was washed 5 times with PBS. TMB substrate was added at 50 μl/well, and incubated at room temperature for 30 minutes, then a stop solution (1.0 N HCl) was added at 50 μl/well. An ELISA plate reader (Multimode Plate Reader, EnSight, purchased from PerkinElmer) was used to read the OD450 nm value, and the ELISA results of VHH-Fc and human CD22-ECD are shown in FIG. 6 and Table 9. Table 9 shows that the purified antibodies are all can bind to human CD22-ECD at ELISA level. The IgG control is hIgG1, and the data in the table are OD450 nm values.

TABLE 9

Binding reaction of VHH-Fc antibodies with human CD22 protein detected by ELISA

| Designation of antibody | OD450 Antibody concentration (nM): 100 | 10 | 0.10 | 0.01 | 0.001 | 0.0001 | 0.00001 | Blank |
|---|---|---|---|---|---|---|---|---|
| S002-NB151-14 | 2.01 | 1.71 | 1.28 | 0.58 | 0.33 | 0.22 | 0.25 | 0.05 |
| S002-NB151-23 | 1.33 | 1.24 | 1.24 | 0.69 | 0.35 | 0.25 | 0.26 | 0.05 |
| S002-NB151-30 | 1.80 | 1.72 | 1.35 | 0.53 | 0.22 | 0.11 | 0.11 | 0.05 |

TABLE 9-continued

Binding reaction of VHH-Fc antibodies with human CD22 protein detected by ELISA

| Designation of antibody | OD450 Antibody concentration (nM) 100 | 10 | 0.10 | 0.01 | 0.001 | 0.0001 | 0.00001 | Blank |
|---|---|---|---|---|---|---|---|---|
| S002-NB151-51 | 1.68 | 1.69 | 1.54 | 0.60 | 0.18 | 0.10 | 0.07 | 0.05 |
| S002-NB151-66 | 1.38 | 1.43 | 1.29 | 0.64 | 0.26 | 0.15 | 0.14 | 0.05 |
| S002-NB151-82 | 1.54 | 1.68 | 1.30 | 0.59 | 0.23 | 0.13 | 0.13 | 0.05 |
| S002-NB150-2 | 2.29 | 1.89 | 1.83 | 1.15 | 0.44 | 0.26 | 0.17 | 0.06 |
| S002-NB150-5 | 2.56 | 2.04 | 1.91 | 1.10 | 0.46 | 0.24 | 0.15 | 0.06 |
| S002-NB150-40 | 2.26 | 1.95 | 1.65 | 0.68 | 0.25 | 0.15 | 0.11 | 0.06 |
| S002-NB150-42 | 2.02 | 1.82 | 1.87 | 0.93 | 0.28 | 0.12 | 0.09 | 0.05 |
| S002-NB150-57 | 2.08 | 1.90 | 1.90 | 1.00 | 0.30 | 0.13 | 0.08 | 0.05 |
| S002-NB151-2 | 1.93 | 1.86 | 1.82 | 1.17 | 0.54 | 0.30 | 0.17 | 0.05 |
| S002-NB151-13 | 2.12 | 1.87 | 1.65 | 0.86 | 0.39 | 0.25 | 0.20 | 0.06 |
| S002-NB151-36 | 2.58 | 2.21 | 1.78 | 0.69 | 0.24 | 0.11 | 0.85 | 0.05 |
| S002-NB151-64 | 2.18 | 2.03 | 1.95 | 1.08 | 0.35 | 0.17 | 0.11 | 0.05 |
| S002-NB151-92 | 1.61 | 2.15 | 1.86 | 0.71 | 0.17 | 0.08 | 0.06 | 0.05 |
| S002-NB150-152n | 3.33 | 2.82 | 2.66 | 1.21 | 0.29 | 0.13 | 0.10 | 0.07 |
| S002-NB150-159n | 3.20 | 2.58 | 2.22 | 0.90 | 0.20 | 0.09 | 0.07 | 0.06 |
| HA22 | 2.01 | 1.92 | 1.50 | 0.45 | 0.13 | 0.07 | 0.06 | 0.05 |
| m971 | 1.77 | 1.87 | 1.55 | 0.56 | 0.15 | 0.08 | 0.06 | 0.05 |
| hIgG1 | 0.15 | 0.08 | 0.06 | 0.06 | 0.06 | 0.06 | 0.05 | 0.06 |

4.2 The Binding of Antibody to Different CD22 Expressing Cells Detected by Flow Cytometry (FACS)

Figure 7A:
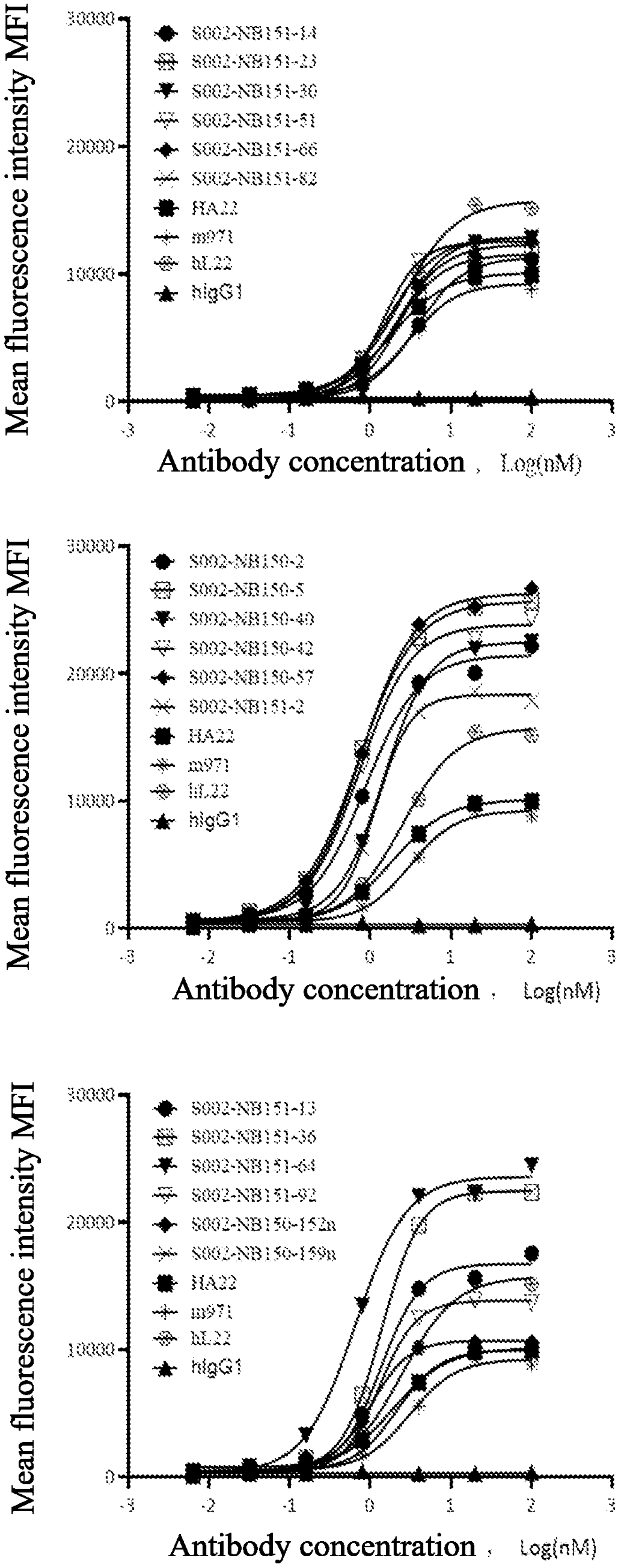
FIG. 7A shows the binding reaction of the VHH-Fc antibodies of the present invention and CHO-K1-human CD22 detected by FACS.
Figure 7B:
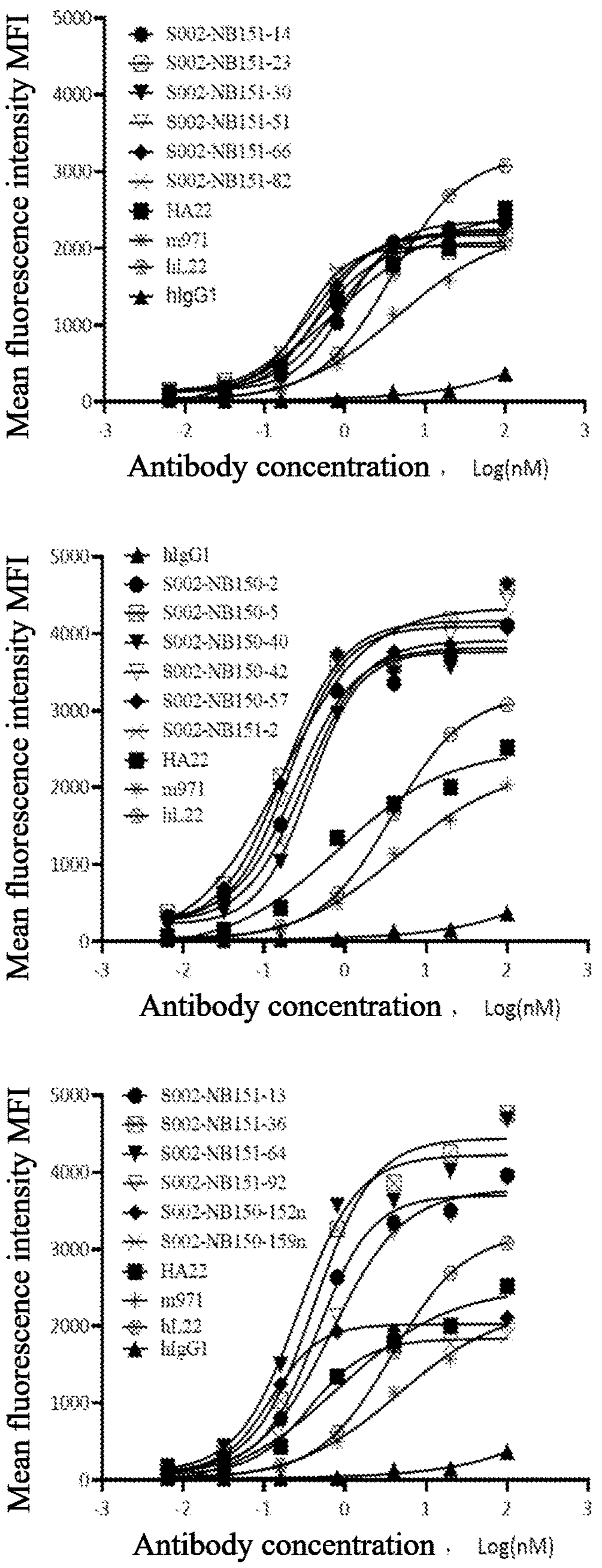
FIG. 7B shows the binding reaction of the VHH-Fc antibodies of the present invention and Raji detected by FACS. The anti-CD22 positive control antibody is: HA22, m971 and hL22, the negative control is hIgG1.
Figure 7C:
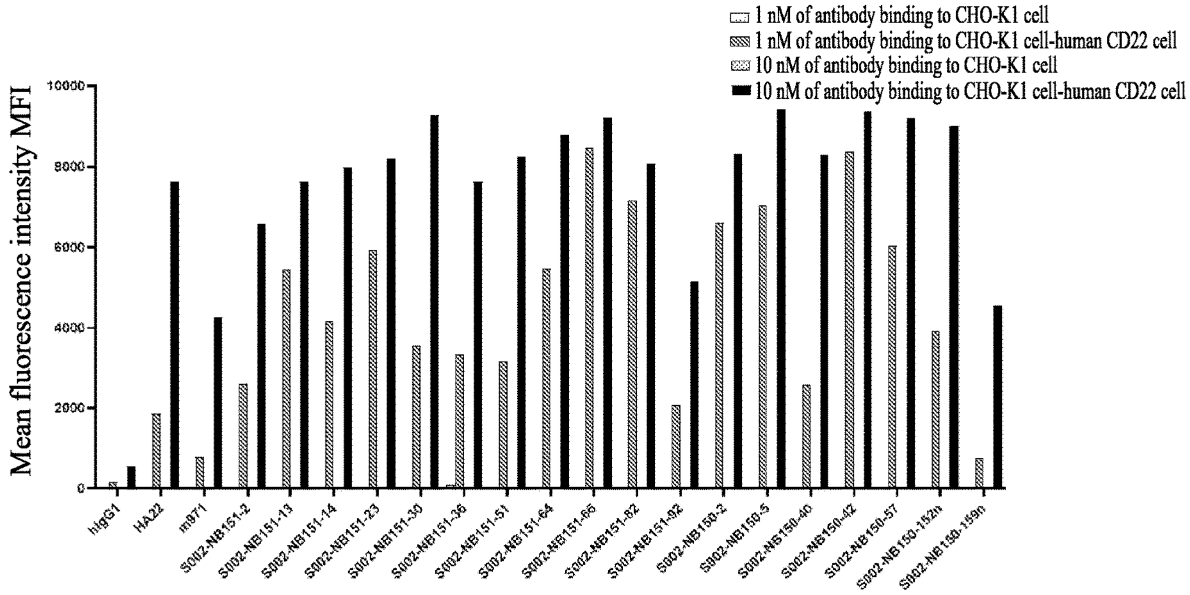
FIG. 7C shows the binding reaction of the VHH-Fc antibodies of the present invention at 1 nM and 10 nM with CHO-K1 cells and CHO-K1-human CD22 2C4 detected by FACS.
Figure 7D:
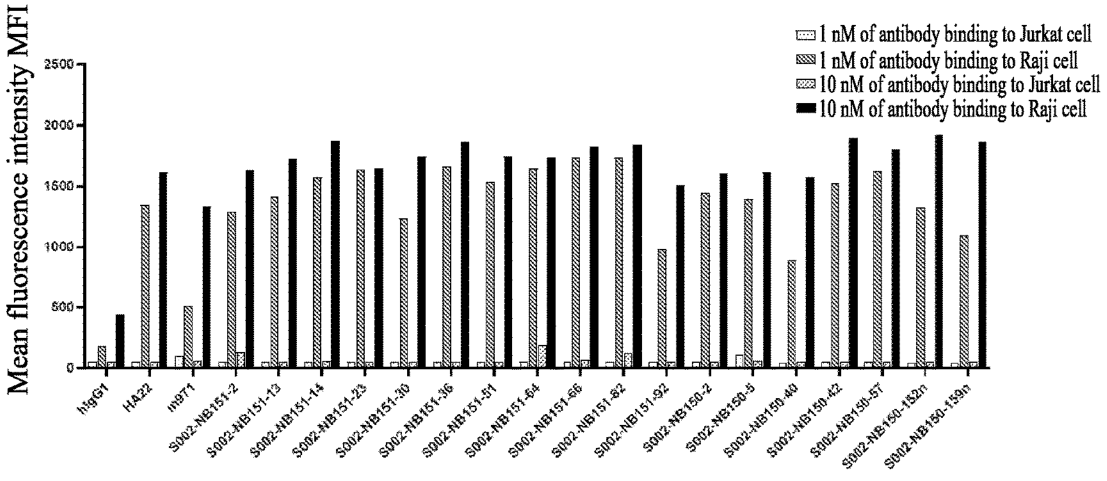
FIG. 7D shows the binding reaction of the VHH-Fc antibodies of the present invention at 1 nM and 10 nM with Raji cells and Jurkat cells detected by FACS.

The required cells were scale-up cultured in a T-75 cell culture flask to the logarithmic growth phase. For the adherent cell CHO-K1, the medium was aspirated, the cells were washed 2 times with PBS buffer, and then digested with trypsin. After the digestion was terminated, the cells were washed 2 times with PBS buffer. For suspension cell Raji, the medium supernatant was directly centrifuged and discarded, and the cell pellet was washed 2 times with PBS. After counting the cells in the previous step, the cell pellet was resuspended with [PBS+2% (w/w) BSA] blocking solution to 2×10 6 cells/ml, and added to a 96-well FACS reaction plate at 50 μl/well, and then the VHH-Fc antibody test sample was added at 50 μl/well, and incubated on ice for 2 hours. The mixture was centrifuged and washed 3 times with PBS buffer, Alexa Flour 488-labeled secondary antibody (purchased from Invitrogen, catalog number: A-11013) was added at 50 μl/well, and incubated on ice for 1 hour. The obtained mixture was centrifuged and washed 5 times with PBS, and FACS (FACS Canto™, purchased from BD Company) was used for detection and result analysis. Data analysis was performed by software (CellQuest) to obtain the mean fluorescence density (MFI) of the cells. And then software (GraphPad Prism8) was used for analysis, data fitting, and EC50 value calculation. The analysis results are shown in Table 10 and FIGS. 7A-7B. The VHH-Fc antibodies all can bind to human CD22 protein on the surface of Raji cells and CHO-K1-human CD22 2C4 cells (FIGS. 7A-7B). The same method was used to detect the binding of the VHH-Fc antibodies to endogenous CD22-negative cell Jurkat cells (purchased from ATCC, TIB-152) and CHO-K1 cells. The results are shown in FIGS. 7C-7D, None of the VHH-Fc antibodies bind to Jurkat cells and CHO-K1 cells, and there is a good specificity.

TABLE 10

Binding reaction of VHH-Fc antibodies with Raji and CHO-K1-human CD22 2C4 cells detected by FACS

| Designation of antibody | Raji Maximum mean fluorescence intensity Max MFI | Raji Ec50 (nM) | CHO-K1-human CD22 2C4 Maximum mean fluorescence intensity Max MFI | CHO-K1-human CD22 2C4 Ec50 (nM) |
|---|---|---|---|---|
| S002-NB151-2 | 4197 | 0.32 | 17895 | 1.17 |
| S002-NB151-13 | 3958 | 0.45 | 17556 | 1.36 |
| S002-NB151-14 | 2370 | 1.03 | 11135 | 3.7 |
| S002-NB151-23 | 2203 | 0.49 | 11799 | 2.02 |
| S002-NB151-30 | 2327 | 0.80 | 12810 | 2.46 |
| S002-NB151-36 | 4761 | 0.41 | 22344 | 1.37 |
| S002-NB151-51 | 2377 | 0.40 | 12810 | 1.45 |
| S002-NB151-64 | 4690 | 0.26 | 24458 | 0.66 |
| S002-NB151-66 | 2313 | 0.48 | 12540 | 2.14 |
| S002-NB151-82 | 2169 | 0.31 | 12967 | 1.67 |
| S002-NB151-92 | 3922 | 0.68 | 13705 | 1.30 |
| S002-NB150-2 | 4106 | 0.25 | 22178 | 0.87 |
| S002-NB150-5 | 4615 | 0.17 | 25743 | 0.71 |
| S002-NB150-40 | 4066 | 0.36 | 22482 | 1.44 |
| S002-NB150-42 | 4465 | 0.20 | 24363 | 0.73 |
| S002-NB150-57 | 4655 | 0.17 | 26675 | 0.76 |

TABLE 10-continued

Binding reaction of VHH-Fc antibodies with Raji and CHO-K1-human CD22 2C4 cells detected by FACS

| Designation of antibody | Raji Maximum mean fluorescence intensity Max MFI | Raji Ec50 (nM) | CHO-K1-human CD22 2C4 Maximum mean fluorescence intensity Max MFI | CHO-K1-human CD22 2C4 Ec50 (nM) |
|---|---|---|---|---|
| S002-NB150-152n | 2113 | 0.12 | 10587 | 1.04 |
| S002-NB150-159n | 1871 | 0.37 | 9655 | 2.14 |
| HA22 | 2521 | 0.83 | 9968 | 1.89 |
| m971 | 2039 | 4.54 | 8839 | 3.07 |
| hL22 | 3080 | 3.80 | 15153 | 2.50 |
| hIgG1 | 374 | Negative | 340 | Negative |

Example 5 Detection of Species Cross-Binding Activity of VHH-Fc Antibodies

5.1 Binding of VHH-Fc Antibodies to Murine CD22 Protein Detected by ELISA

In order to detect the species cross-binding activity of the VHH-Fc antibodies, an ELISA plate was coated with commercial mouse CD22 (ACROBiosystems, catalog number: SI2-M52Ha), and the ELISA detection was performed according to the method in Example 4.1. The ELISA results of VHH-Fc and murine CD22-ECD are shown in FIG. 8 and Table 11. Table 11 shows that only S002-NB151-51 of the purified antibodies binds to murine CD22-ECD at the ELISA level. The IgG control is hIgG1, and 983 is the serum of human CD22-ECD-His immunized mice as a positive control, and the data in the table are OD450 nm values.

TABLE 11

Binding reaction of VHH-Fc antibodies with murine CD22 protein detected by ELISA

| Designation of antibody | OD450 Antibody concentration (nM) 100 | 10 | 0.10 | 0.01 | 0.001 | 0.0001 | 0.00001 | Blank |
|---|---|---|---|---|---|---|---|---|
| S002-NB151-14 | 0.15 | 0.08 | 0.06 | 0.06 | 0.07 | 0.07 | 0.07 | 0.09 |
| S002-NB151-23 | 0.14 | 0.07 | 0.06 | 0.06 | 0.06 | 0.06 | 0.07 | 0.08 |
| S002-NB151-30 | 0.12 | 0.07 | 0.06 | 0.06 | 0.06 | 0.07 | 0.07 | 0.09 |
| S002-NB151-51 | 2.31 | 2.77 | 2.33 | 0.69 | 0.13 | 0.08 | 0.07 | 0.09 |
| S002-NB151-66 | 0.14 | 0.08 | 0.06 | 0.06 | 0.06 | 0.07 | 0.08 | 0.10 |
| S002-NB151-82 | 0.12 | 0.08 | 0.06 | 0.07 | 0.06 | 0.08 | 0.07 | 0.09 |
| S002-NB150-2 | 0.09 | 0.06 | 0.05 | 0.05 | 0.05 | 0.05 | 0.05 | 0.05 |
| S002-NB150-5 | 0.13 | 0.06 | 0.06 | 0.05 | 0.05 | 0.05 | 0.05 | 0.05 |
| S002-NB150-40 | 0.06 | 0.05 | 0.05 | 0.05 | 0.05 | 0.05 | 0.05 | 0.06 |
| S002-NB150-42 | 0.07 | 0.06 | 0.05 | 0.05 | 0.05 | 0.05 | 0.05 | 0.06 |
| S002-NB150-57 | 0.07 | 0.06 | 0.05 | 0.05 | 0.05 | 0.05 | 0.05 | 0.05 |
| S002-NB151-2 | 0.08 | 0.06 | 0.05 | 0.06 | 0.05 | 0.06 | 0.05 | 0.05 |
| S002-NB151-13 | 0.38 | 0.11 | 0.06 | 0.06 | 0.06 | 0.06 | 0.06 | 0.05 |
| S002-NB151-36 | 0.07 | 0.05 | 0.05 | 0.05 | 0.05 | 0.05 | 0.06 | 0.06 |
| S002-NB151-64 | 0.10 | 0.06 | 0.11 | 0.08 | 0.05 | 0.05 | 0.06 | 0.05 |
| S002-NB151-92 | 0.07 | 0.05 | 0.07 | 0.05 | 0.05 | 0.05 | 0.06 | 0.05 |
| S002-NB150-152n | 0.10 | 0.06 | 0.06 | 0.07 | 0.06 | 0.06 | 0.06 | 0.07 |
| S002-NB150-159n | 0.07 | 0.05 | 0.05 | 0.05 | 0.05 | 0.05 | 0.05 | 0.06 |
| 983* | 2.81 | 2.87 | 2.34 | 1.04 | 0.27 | 0.12 | 0.10 | 0.11 |
| hIgG1 | 0.10 | 0.09 | 0.09 | 0.08 | 0.09 | 0.08 | 0.09 | 0.09 |

*983 serum was 5-fold serially diluted from 1:100.

Figure 9:
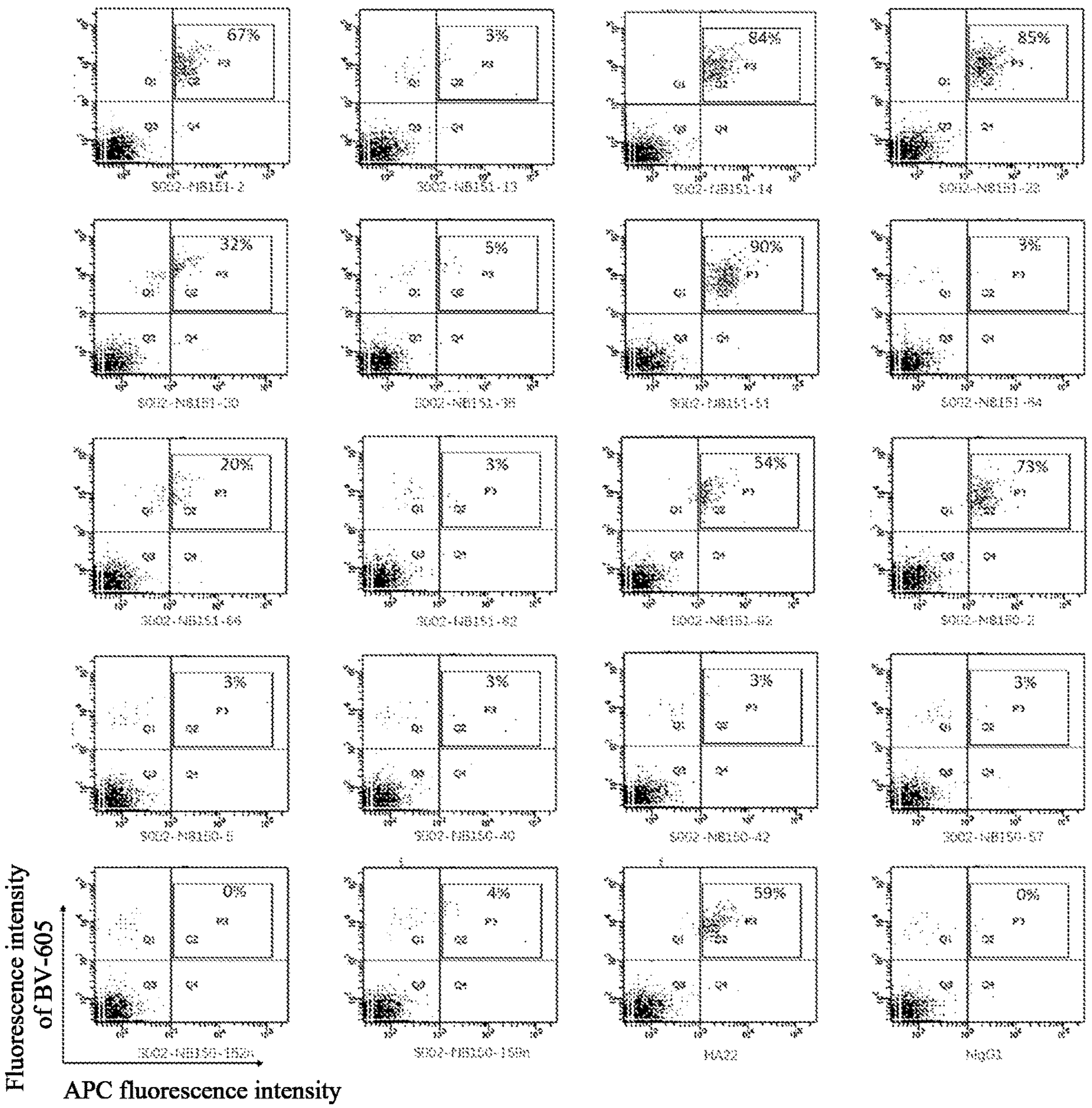
FIG. 9 shows a scatter plot of peripheral blood mononuclear cells of cynomolgus monkeys stained with both CD20 antibody and 1 nM of VHH-Fc antibodies of the present invention detected by FACS, CD20 is a B cell marker, and the ratio shown in the figure is the ratio of VHH-Fc antibodies positive cells of the present invention to CD20 positive cells, and the anti-CD22 positive control antibody is: HA22, the negative control is hIgG1.

5.2 Binding of VHH-Fc Antibodies to Peripheral Blood B Cells of Cynomolgus Monkey (Latin Name: *Macaca fascicularis*) Detected by FACS The monkey peripheral blood mononuclear cells were extracted from fresh cynomolgus monkey peripheral blood (purchased from Shanghai Medicilon Inc.) according to the instructions of Ficoll-Paque Plus (purchased from GE Healthcare, catalog number: 171440-02). After the cell suspension was centrifuged, the cells were resuspended in PBS containing 1% BSA, and then the cells were counted. At the same time, the murine antibody Brilliant Violet 605 anti-human CD20 (catalog number: 302334, purchased from Biolegend) with monkey CD20 cross-binding activity and the VHH-Fc antibodies to be tested (1 nM, 10 nM and 100 nM) were added. The mixture was incubated for 1 hour at room temperature. After washing the cells three times, APC-labeled secondary antibody anti-human IgG Fc (catalog number: 409306, purchased from Biolegend) was added. After incubation at room temperature in the dark for 30 minutes, the cells were washed 5 times, gently resuspended with PBS containing 1% BSA, and detected and analyzed by FACS (FACS Canto™, purchased from BD Company). Wherein CD20 was used as a marker of B cells, and the CD20-positive B cell population was gated, the proportion of VHH-Fc positive cells was analyzed, and the proportion of VHH-Fc positive cell population to B cell population was calculated after treatments with VHH-Fc antibodies at the concentrations of 100 nM, 10 nM and 1 nM, respectively. The results are shown in Table 12. The scatter plot of double-stained cells by Brilliant Violet 605-labeled CD20 and APC secondary antibody indirectly labeled VHH-Fc is shown in FIG. 9 (under the condition of 1 nM of VHH-Fc antibody concentration). It can be seen from the results that 5002-NB151-2, S002-NB151-14, 5002-NB151-23, 5002-NB151-92, 5002-NB151-51, 5002-NB150-2 still bind to B cells of cynomolgus monkeys in a high proportion even under the condition of low concentration of 1 nM, and has equivalent or better binding activity than positive antibody HA22. Other antibodies had no binding or relatively weak binding to cynomolgus monkey CD22.

TABLE 12

Binding reaction of VHH-Fc antibodies with cynomolgus monkey B cells detected by FACS
Proportion of VHH-Fc antibody positive cells to B cells (%)

| Designation of antibody | Antibody concentration 100 nM | 10 nM | 1 nM |
|---|---|---|---|
| S002-NB151-2 | 84 | 86 | 67 |
| S002-NB151-13 | 61 | 23 | 3 |
| S002-NB151-14 | 94 | 90 | 84 |
| S002-NB151-23 | 94 | 88 | 85 |
| S002-NB151-30 | 90 | 70 | 32 |
| S002-NB151-36 | 40 | 10 | 5 |
| S002-NB151-51 | 96 | 93 | 90 |
| S002-NB151-64 | 19 | 4 | 3 |
| S002-NB151-66 | 22 | 5 | 20 |
| S002-NB151-82 | 2 | 2 | 3 |
| S002-NB151-92 | 75 | 69 | 54 |
| S002-NB150-2 | 89 | 80 | 73 |
| S002-NB150-5 | 36 | 3 | 3 |
| S002-NB150-40 | 3 | 0 | 3 |
| S002-NB150-42 | 80 | 36 | 3 |
| S002-NB150-57 | 58 | 16 | 3 |
| S002-NB150-152n | 14 | 6 | 0 |
| S002-NB150-159n | 30 | 18 | 4 |
| HA22 | 96 | 84 | 59 |
| hIgG1 | 3 | 0 | 0 |

Example 6 CD22 Antibody Affinity Assay

6.1 Assay of Affinity of VHH-Fc to Human CD22-ECD-his Protein

Figure 10:
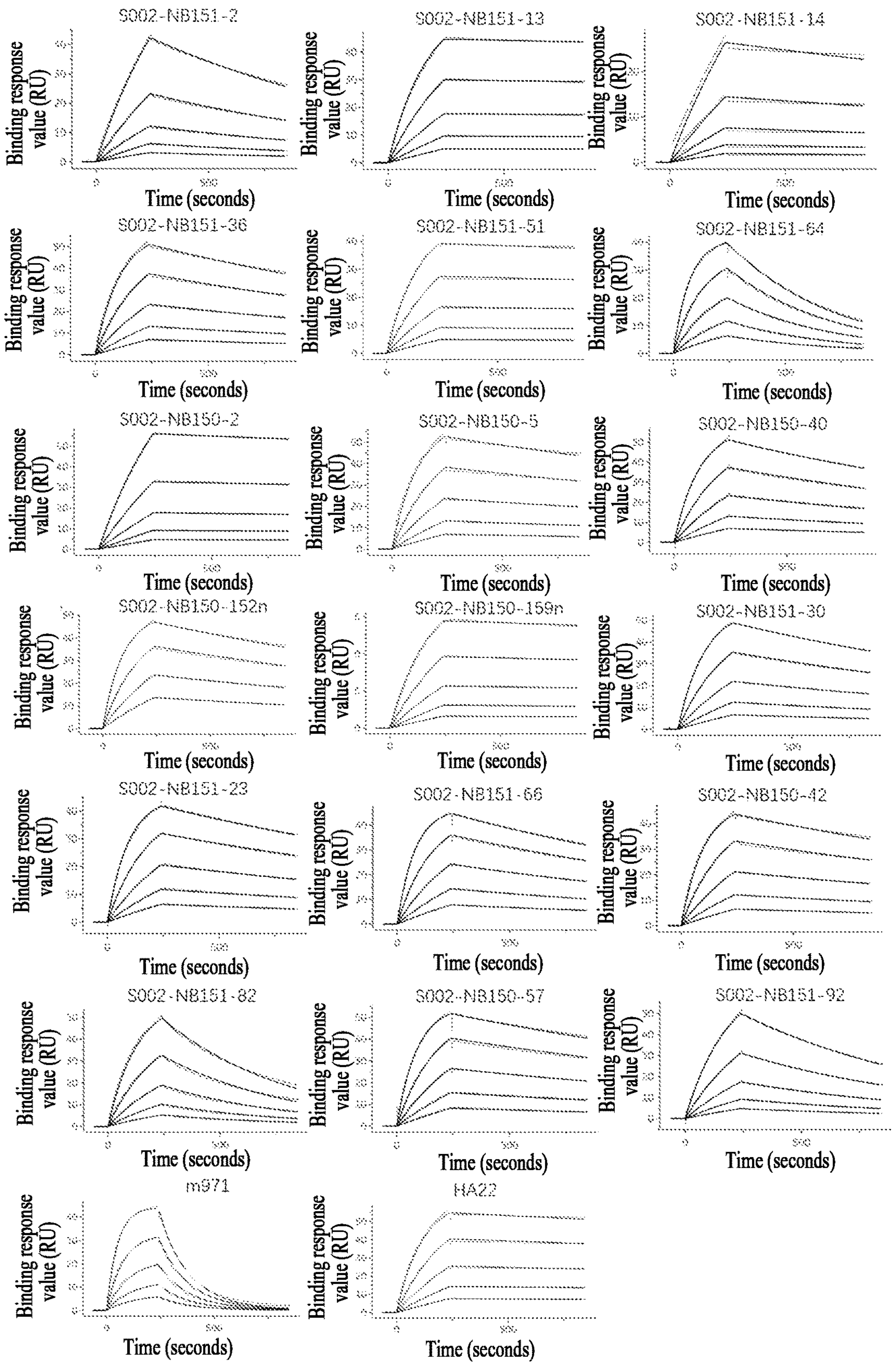
FIG. 10 shows the affinity of the VHH-Fc antibodies of the present invention to human CD22 detected by SPR, and the anti-human CD22 positive control antibody is: HA22 and m971.

Anti-human CD22 VHH-hFc antibody was captured using a Protein A chip (GE Healthcare; 29-127-558). Sample buffer and running buffer were HBS-EP+(10 mM HEPES, 150 mM NaCl, 3 mM EDTA, 0.05% surfactant P20) (GE Healthcare; BR-1006-69). The flow-through cell was set to 25° C. The sample block was set to 16° C. Both were pretreated with the running buffer. In each cycle, the antibody to be tested was first captured with a Protein A chip, then a single concentration of CD22 antigen protein was injected. The binding and dissociation process of the antibody and the antigen protein was recorded, and finally Glycine pH 1.5 (GE Healthcare; BR-1003-54) was used to complete chip regeneration. Binding was measured by injecting different concentrations of recombinant human CD22-ECD His in solution for 240 s with a flow rate of 30 μL/min. The concentration started from 200 nM (see the detailed results for the actual concentration in the test) and was diluted at 1:1, making a total of 5 concentrations. The dissociation phase was monitored for up to 600 s and was triggered by switching from sample solution to running buffer. The surface was regenerated by washing with a 10 mM of glycine solution (pH 1.5) for 30 s at a flow rate of 30 μL/min. Bulk refractive index difference was corrected by subtracting the response obtained from the goat anti-human Fc surface. Blank injection was also subtracted (=double reference). For calculation of apparent KD and other kinetic parameters, Langmuir 1:1 model was used. The binding rate (Ka), dissociation rate (Kd) and binding affinity (KD) of the VHH-Fc antibodies to human CD22-His protein are shown in Table 13, and the antibody HA22 was used as a control. As shown in FIG. 10 and Table 13, the affinity of VHH-Fc antibodies to human CD22 is all better than 4.89E-8M

TABLE 13

Affinity of VHH-Fc antibodies to human CD22 detected by SPR (biacore)

| Designation of antibody | ka (1/Ms) | kd (1/s) | KD (M) |
|---|---|---|---|
| S002-NB151-2 | 1.69E+04 | 8.27E−04 | 4.89E−08 |
| S002-NB151-13 | 5.98E+04 | 3.58E−05 | 5.98E−10 |
| S002-NB151-14 | 1.60E+04 | 2.54E−04 | 1.59E−08 |
| S002-NB151-23 | 2.04E+05 | 4.76E−04 | 2.33E−09 |
| S002-NB151-30 | 8.43E+04 | 5.14E−04 | 6.09E−09 |
| S002-NB151-36 | 8.73E+04 | 5.20E−04 | 5.97E−09 |
| S002-NB151-51 | 1.42E+05 | 7.39E−05 | 5.20E−10 |
| S002-NB151-64 | 2.39E+05 | 2.07E−03 | 8.68E−09 |
| S002-NB151-66 | 2.49E+05 | 5.62E−04 | 2.25E−09 |
| S002-NB151-82 | 6.00E+04 | 1.74E−03 | 2.90E−08 |
| S002-NB151-92 | 4.40E+04 | 1.11E−03 | 2.52E−08 |
| S002-NB150-2 | 3.17E+04 | 7.61E−05 | 2.40E−09 |
| S002-NB150-5 | 8.32E+04 | 3.09E−04 | 3.71E−09 |
| S002-NB150-40 | 8.63E+04 | 5.41E−04 | 6.27E−09 |
| S002-NB150-42 | 1.96E+05 | 4.23E−04 | 2.16E−09 |
| S002-NB150-57 | 1.10E+05 | 4.07E−04 | 3.70E−09 |
| S002-NB150-152n | 2.12E+05 | 4.42E−04 | 2.08E−09 |
| S002-NB150-159n | 2.89E+04 | 6.95E−05 | 2.40E−09 |
| HA22 | 8.15E+04 | 1.12E−04 | 1.37E−09 |
| m971 | 2.51E+05 | 7.36E−03 | 2.93E−08 |

6.2 Assay of Affinity of VHH-Fc to Cynomolgus Monkey CD22-ECD-his Protein

Figure 11:
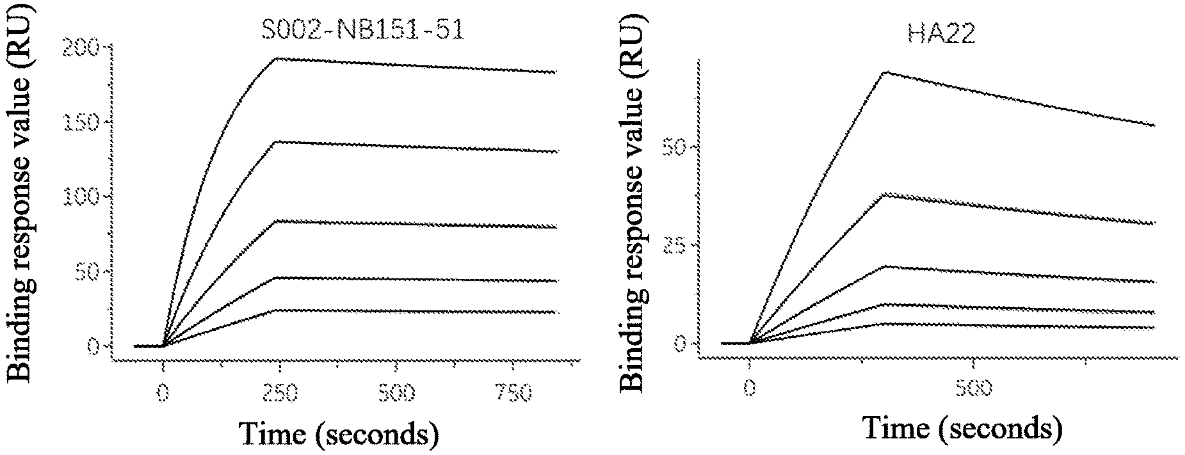
FIG. 11 shows the affinity of the VHH-Fc antibodies of the present invention to cynomolgus monkey CD22 detected by SPR, and the anti-human CD22 positive control antibody is: HA22.

According to the method of Example 6.1, the affinity of VHH-Fc antibodies to cynomolgus monkey CD22-ECD-His (purchased from R&D, catalog number: 9864-SL-050) protein was determined, and the results are shown in FIG. 11 and Table 14. The antibody S002-NB151-51, which still binds to B cells of cynomolgus monkeys in a high proportion at low concentration, has a high affinity to CD22 of cynomolgus monkeys, which is 5.07E-10M.

TABLE 14

Affinity of VHH-Fc antibodies to cynoCD22 detected by SPR (biacore)

| Designation of antibody | ka (1/Ms) | kd (1/s) | KD (M) |
|---|---|---|---|
| S002-NB151-2 | There is binding/the fit is poor | | |
| S002-NB151-23 | There is binding/the fit is poor | | |
| S002-NB151-14 | There is binding/the fit is poor | | |
| S002-NB151-51 | 1.64E+05 | 8.31E−05 | 5.07E−10 |
| S002-NB151-92 | There is binding/the fit is poor | | |
| S002-NB150-2 | There is binding/the fit is poor | | |
| HA22 | 1.27E+04 | 3.76E−04 | 2.97E−07 |

Example 7 Antibody Antigen-Binding Epitope Analysis

7.1 Identification of Antigen-Binding Region of Antibody

Figure 12A:
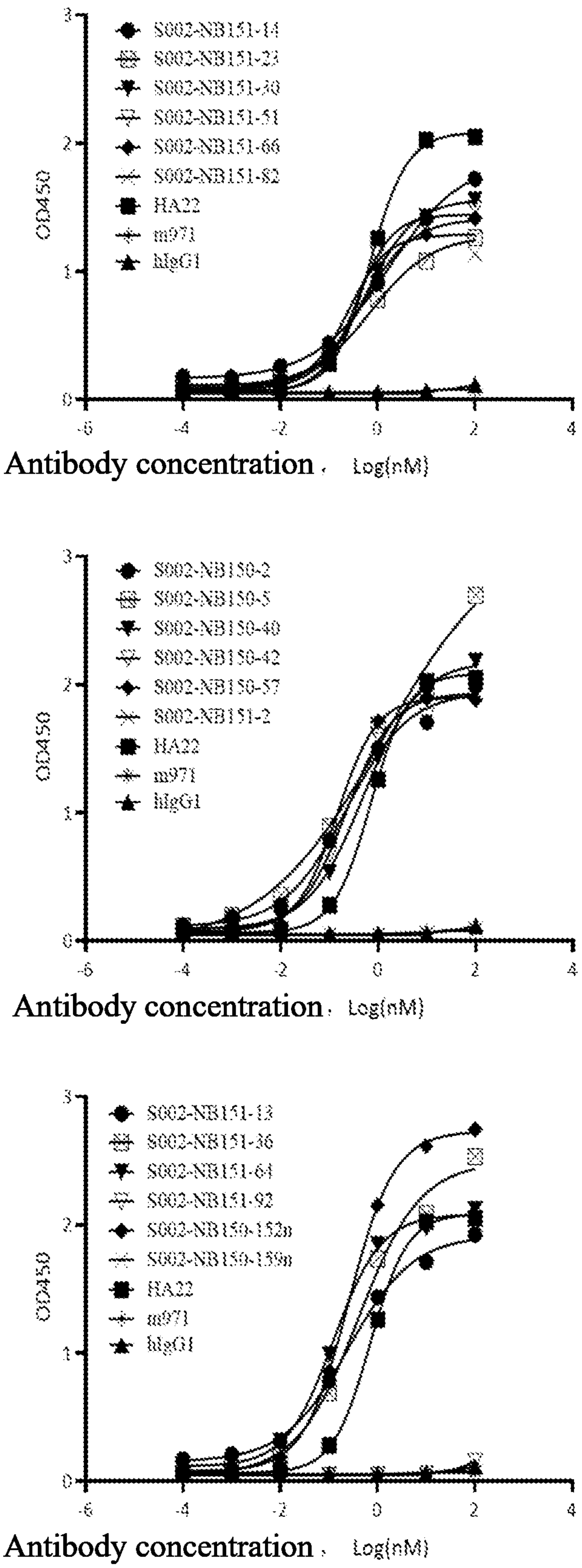
FIG. 12A shows the binding reaction of the VHH-Fc of the present invention with human CD22 domain1-4-His protein detected by ELISA.
Figure 12B:
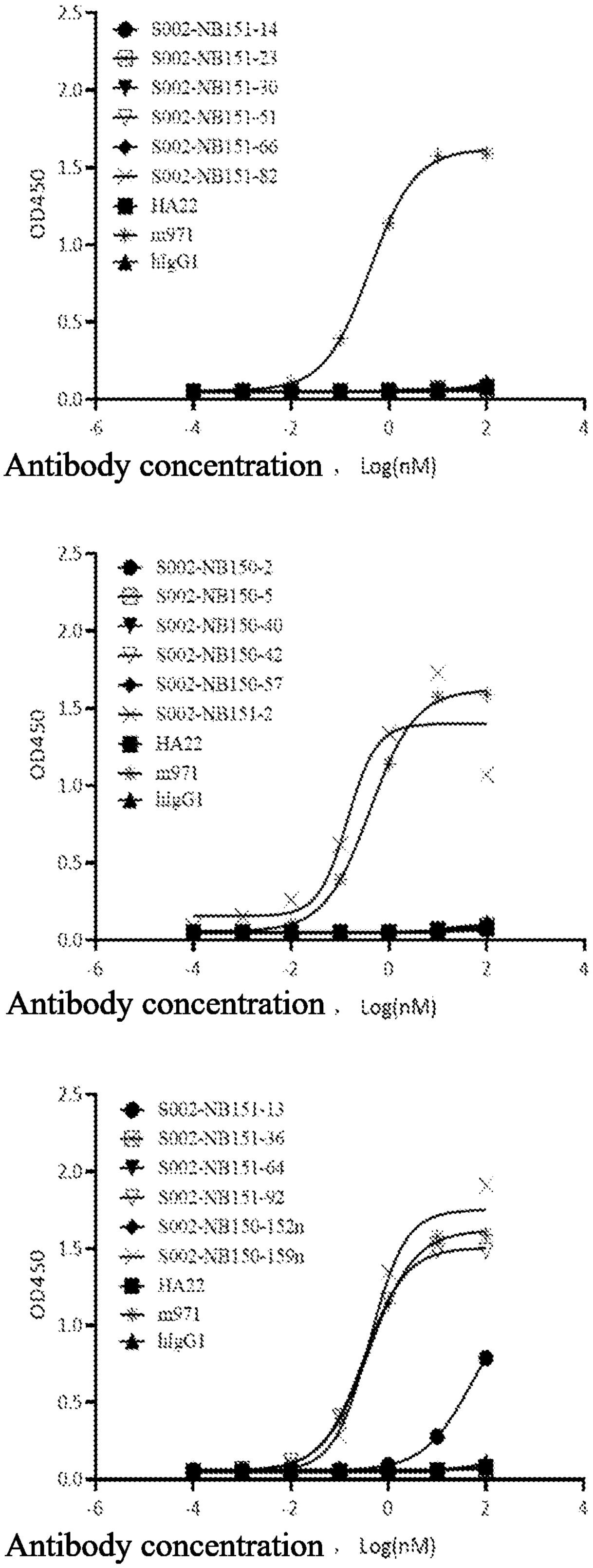
FIG. 12B shows the binding reaction of the VHH-Fc of the present invention with human CD22 domain5-7-His protein detected by ELISA. The anti-CD22 positive control antibody is: HA22 and m971, the negative control is hIgG1.

The CD22 protein has 7 IgG-like domains outside the cell, in which domain 1 is located at the farthest end from the membrane and domain 7 is located at the nearest end from the membrane, the antigen-binding epitopes of HA22 and hL22 are located in domain 2-3, and the antigen-binding epitope of m971 is located in domain5-7. In order to identify the antigen-binding epitope distribution of the VHH antibodies, according to the ELISA method in Example 4.1, human CD22-domain1-4-His (distal end of membrane) and human CD22 domain5-7-His (proximal end of membrane) were used for coating, respectively. The VHH antibodies were classified into the type of distal end of membrane and the type of proximal end of membrane, as shown in FIGS. 12A-12B and Table 15, the VHH antibodies can be divided into two categories:

TABLE 15

Epitopes at the distal end of membrane and epitopes at the proximal end of membrane of the VHH antibodies classified by ELISA method

| Designation of antibody | Binding region domain 1-4 | Binding region domain 5-7 |
|---|---|---|
| S002-NB151-13 | + | − |
| S002-NB151-14 | + | − |
| S002-NB151-23 | + | − |
| S002-NB151-30 | + | − |
| S002-NB151-36 | + | − |
| S002-NB151-51 | + | − |
| S002-NB151-64 | + | − |
| S002-NB151-66 | + | − |
| S002-NB151-82 | + | − |
| S002-NB150-2 | + | − |
| S002-NB150-5 | + | − |
| S002-NB150-40 | + | − |
| S002-NB150-42 | + | − |
| S002-NB150-57 | + | − |
| S002-NB150-152n | + | − |
| S002-NB151-2 | − | + |
| S002-NB151-92 | − | + |
| S002-NB150-159n | − | + |

7.2 Antibody Antigen-Binding Epitope Competition Experiment (Epitope Binning)

Figure 14:
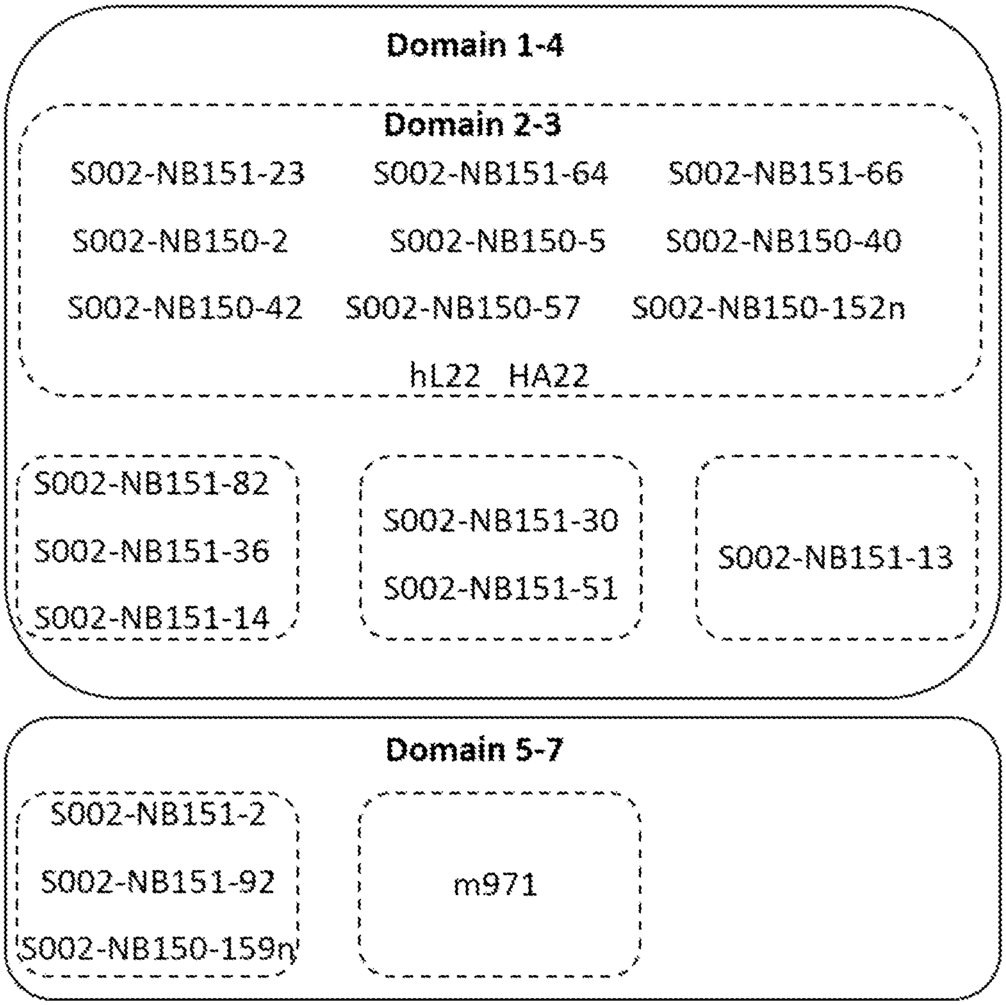
FIG. 14 shows the antigen epitope classification of the VHH antibodies of the present invention.

Competitive ELISA was used to classify the epitopes of VHH antibodies and control antibody with known epitopes. According to the method in Example 4.2, the ELISA plate was coated with 2 μg/mL of the antibody, and the human CD22-ECD-his protein was serially diluted starting from 30 μg/mL, and the EC80 value was calculated (Table 16). The ELISA plate was coated with 2 μg/mL of the antibody, 25 μg/mL of the antibody to be detected was added, and then human CD22-ECD-his protein corresponding to each antibody to be detected was added at the EC80 concentration, incubated for 2 hours, and washed 5 times with PBS, and then HRP-labeled anti-His antibody was added for detection. If there is no competitive relationship between the antibody coated on the plate and the antibody to be detected in the solution, the antibody coated on the plate can bind to the complex of the antibody to be detected and the human CD22-ECD-his antigen in solution, and the absorption at OD450 nm was detected, and the inhibition rate between each pair of antibodies was calculated according to the absorbance at OD450 nm (FIG. 13). According to the inhibition rate, each antibody epitope was classified as shown in FIG. 14, and 5002-NB151-23, 5002-NB151-64, S002-NB151-66, 5002-NB150-2, 5002-NB150-5, 5002-NB150-40, 5002-NB150-42, 5002-NB150-57, 5002-NB150-152n competed with hL22 and HA22 and could be classified into one category; there was a competitive relationship among 5002-NB151-82, 5002-NB151-36, and 5002-NB151-14; there was a competitive relationship between 5002-NB151-30 and S002-NB151-51; S002-NB151-13 did not compete with any antibody; all of the antibodies described above could bind to domain 1-4 but not bind to domain 5-7, and could be classified into one large category. There was competition among 5002-NB151-2, 5002-NB151-92, and 5002-NB150-159n; m971 did not compete with any antibody, all of the antibodies could bind to domain 5-7 but not bind to domain 1-4, and could be classified into one large category.

TABLE 16

EC80 value of human CD22-ECD-his protein corresponding to VHH antibody

| Designation of antibody | EC80 (nM) |
|---|---|
| domain 1-4 | |
| S002-NB151-23 | 3.20 |
| HA22 | 0.80 |
| S002-NB151-64 | 17.60 |
| S002-NB151-66 | 2.80 |
| S002-NB150-2 | 1.73 |
| S002-NB150-5 | 3.73 |
| S002-NB150-40 | 2.40 |
| S002-NB150-42 | 2.27 |
| S002-NB150-57 | 1.60 |
| S002-NB150-152n | 4.00 |
| hL22 | 0.93 |
| S002-NB151-82 | 4.00 |
| S002-NB151-36 | 11.07 |
| S002-NB151-14 | 32.27 |
| S002-NB151-30 | 8.13 |
| S002-NB151-51 | 1.60 |
| S002-NB151-13 | 80.13 |
| domain 5-7 | |
| S002-NB151-2 | 20.80 |
| S002-NB151-92 | 15.60 |
| S002-NB150-15911 | 5.73 |
| 111971 | 2.13 |

The invention claimed is:

1. A nanobody or an antigen-binding fragment that specifically binds to CD22, wherein the nanobody or the antigen-binding fragment comprises a combination of CDRs, the combination of CDRs comprising: CDR1, CDR2, and CDR3; the CDR1, CDR2 and CDR3 having any sequence combination selected from the following:

| | SEQ ID NO. | | |
|---|---|---|---|
| No. | CDR1 | CDR2 | CDR3 |
| VH1 | SEQ ID NO. 57 | SEQ ID NO. 58 | SEQ ID NO. 59 |
| VH2 | SEQ ID NO. 60 | SEQ ID NO. 61 | SEQ ID NO. 62 |
| VH3 | SEQ ID NO. 63 | SEQ ID NO. 64 | SEQ ID NO. 65 |
| VH4 | SEQ ID NO. 66 | SEQ ID NO. 67 | SEQ ID NO. 68 |
| VH5 | SEQ ID NO. 69 | SEQ ID NO. 70 | SEQ ID NO. 71 |
| VH6 | SEQ ID NO. 72 | SEQ ID NO. 73 | SEQ ID NO. 74 |
| VH7 | SEQ ID NO. 75 | SEQ ID NO. 76 | SEQ ID NO. 77 |
| VH8 | SEQ ID NO. 78 | SEQ ID NO. 79 | SEQ ID NO. 80 |
| VH9 | SEQ ID NO. 81 | SEQ ID NO. 82 | SEQ ID NO. 83 |
| VH10 | SEQ ID NO. 84 | SEQ ID NO. 85 | SEQ ID NO. 86 |
| VH11 | SEQ ID NO. 87 | SEQ ID NO. 88 | SEQ ID NO. 89 |
| VH12 | SEQ ID NO. 90 | SEQ ID NO. 91 | SEQ ID NO. 92 |
| VH13 | SEQ ID NO. 93 | SEQ ID NO. 94 | SEQ ID NO. 95 |
| VH14 | SEQ ID NO. 96 | SEQ ID NO. 97 | SEQ ID NO. 98 |
| VH15 | SEQ ID NO. 99 | SEQ ID NO. 100 | SEQ ID NO. 101 |
| VH16 | SEQ ID NO. 102 | SEQ ID NO. 103 | SEQ ID NO. 104 |
| VH17 | SEQ ID NO. 105 | SEQ ID NO. 106 | SEQ ID NO. 107 |
| VH18 | SEQ ID NO. 108 | SEQ ID NO. 109 | SEQ ID NO. 110 |
| VH19 | SEQ ID NO. 111 | SEQ ID NO. 112 | SEQ ID NO. 113 |
| VH20 | SEQ ID NO. 114 | SEQ ID NO. 115 | SEQ ID NO. 116 |
| VH21 | SEQ ID NO. 117 | SEQ ID NO. 118 | SEQ ID NO. 119 |
| VH22 | SEQ ID NO. 120 | SEQ ID NO. 121 | SEQ ID NO. 122 |
| VH23 | SEQ ID NO. 123 | SEQ ID NO. 124 | SEQ ID NO. 125 |
| VH24 | SEQ ID NO. 126 | SEQ ID NO. 127 | SEQ ID NO. 128 |
| VH25 | SEQ ID NO. 129 | SEQ ID NO. 130 | SEQ ID NO. 131 |
| VH26 | SEQ ID NO. 132 | SEQ ID NO. 133 | SEQ ID NO. 134 |
| VH27 | SEQ ID NO. 135 | SEQ ID NO. 136 | SEQ ID NO. 137 |
| VH28 | SEQ ID NO. 138 | SEQ ID NO. 139 | SEQ ID NO. 140 |
| VH29 | SEQ ID NO. 141 | SEQ ID NO. 142 | SEQ ID NO. 143 |
| VH30 | SEQ ID NO. 144 | SEQ ID NO. 145 | SEQ ID NO. 146 |
| VH31 | SEQ ID NO. 147 | SEQ ID NO. 148 | SEQ ID NO. 149 |
| VH32 | SEQ ID NO. 150 | SEQ ID NO. 151 | SEQ ID NO. 152 |
| VH33 | SEQ ID NO. 153 | SEQ ID NO. 154 | SEQ ID NO. 155 |
| VH34 | SEQ ID NO. 156 | SEQ ID NO. 157 | SEQ ID NO. 158 |
| VH35 | SEQ ID NO. 159 | SEQ ID NO. 160 | SEQ ID NO. 161 |
| VH36 | SEQ ID NO. 162 | SEQ ID NO. 163 | SEQ ID NO. 164 |
| VH37 | SEQ ID NO. 165 | SEQ ID NO. 166 | SEQ ID NO. 167 |
| VH38 | SEQ ID NO. 168 | SEQ ID NO. 169 | SEQ ID NO. 170 |
| VH39 | SEQ ID NO. 171 | SEQ ID NO. 172 | SEQ ID NO. 173 |
| VH40 | SEQ ID NO. 174 | SEQ ID NO. 175 | SEQ ID NO. 176 |
| VH41 | SEQ ID NO. 177 | SEQ ID NO. 178 | SEQ ID NO. 179 |
| VH42 | SEQ ID NO. 180 | SEQ ID NO. 181 | SEQ ID NO. 182 |
| VH43 | SEQ ID NO. 183 | SEQ ID NO. 184 | SEQ ID NO. 185 |
| VH44 | SEQ ID NO. 186 | SEQ ID NO. 187 | SEQ ID NO. 188 |
| VH45 | SEQ ID NO. 189 | SEQ ID NO. 190 | SEQ ID NO. 191 |
| VH46 | SEQ ID NO. 192 | SEQ ID NO. 193 | SEQ ID NO. 194 |
| VH47 | SEQ ID NO. 195 | SEQ ID NO. 196 | SEQ ID NO. 197 |
| VH48 | SEQ ID NO. 198 | SEQ ID NO. 199 | SEQ ID NO. 200 |
| VH49 | SEQ ID NO. 201 | SEQ ID NO. 202 | SEQ ID NO. 203 |
| VH50 | SEQ ID NO. 204 | SEQ ID NO. 205 | SEQ ID NO. 206 |
| VH51 | SEQ ID NO. 207 | SEQ ID NO. 208 | SEQ ID NO. 209 |
| VH52 | SEQ ID NO. 210 | SEQ ID NO. 211 | SEQ ID NO. 212 |
| VH53 | SEQ ID NO. 213 | SEQ ID NO. 214 | SEQ ID NO. 215 |
| VH54 | SEQ ID NO. 216 | SEQ ID NO. 217 | SEQ ID NO. 218 |

wherein each CDR1, CDR2 and CDR3 is coded according to the prevailing analysis methods of KABAT, Chothia or IMGT.

2. The nanobody or the antigen-binding fragment of claim 1, wherein (1) the CDR1, CDR2 and CDR3 have sequences as shown in SEQ ID NO. 57, 58 and 59, respectively;

(2) the CDR1, CDR2 and CDR3 have sequences as shown in SEQ ID NO. 60, 61 and 62, respectively;

(3) the CDR1, CDR2 and CDR3 have sequences as shown in SEQ ID NO. 63, 64 and 65, respectively;

(4) the CDR1, CDR2 and CDR3 have sequences as shown in SEQ ID NO. 66, 67 and 68, respectively;

(5) the CDR1, CDR2 and CDR3 have sequences as shown in SEQ ID NO. 69, 70 and 71, respectively;

(6) the CDR1, CDR2 and CDR3 have sequences as shown in SEQ ID NO. 72, 73 and 74, respectively;

(7) the CDR1, CDR2 and CDR3 have sequences as shown in SEQ ID NO. 75, 76 and 77, respectively;

(8) the CDR1, CDR2 and CDR3 have sequences as shown in SEQ ID NO. 78, 79 and 80, respectively;

(9) the CDR1, CDR2 and CDR3 have sequences as shown in SEQ ID NO. 81, 82 and 83, respectively;

(10) the CDR1, CDR2 and CDR3 have sequences as shown in SEQ ID NO. 84, 85 and 86, respectively;

(11) the CDR1, CDR2 and CDR3 have sequences as shown in SEQ ID NO. 87, 88 and 89, respectively;

(12) the CDR1, CDR2 and CDR3 have sequences as shown in SEQ ID NO. 90, 91 and 92, respectively;

(13) the CDR1, CDR2 and CDR3 have sequences as shown in SEQ ID NO. 93, 94 and 95, respectively;
(14) the CDR1, CDR2 and CDR3 have sequences as shown in SEQ ID NO. 96, 97 and 98, respectively;
(15) the CDR1, CDR2 and CDR3 have sequences as shown in SEQ ID NO. 99, 100 and 101, respectively;
(16) the CDR1, CDR2 and CDR3 have sequences as shown in SEQ ID NO. 102, 103 and 104, respectively;
(17) the CDR1, CDR2 and CDR3 have sequences as shown in SEQ ID NO. 105, 106 and 107, respectively;
(18) the CDR1, CDR2 and CDR3 have sequences as shown in SEQ ID NO. 108, 109 and 110, respectively;
(19) the CDR1, CDR2 and CDR3 have sequences as shown in SEQ ID NO. 111, 112 and 113, respectively;
(20) the CDR1, CDR2 and CDR3 have sequences as shown in SEQ ID NO. 114, 115 and 116, respectively;
(21) the CDR1, CDR2 and CDR3 have sequences as shown in SEQ ID NO. 117, 118 and 119, respectively;
(22) the CDR1, CDR2 and CDR3 have sequences as shown in SEQ ID NO. 120, 121 and 122, respectively;
(23) the CDR1, CDR2 and CDR3 have sequences as shown in SEQ ID NO. 123, 124 and 125, respectively;
(24) the CDR1, CDR2 and CDR3 have sequences as shown in SEQ ID NO. 126, 127 and 128, respectively;
(25) the CDR1, CDR2 and CDR3 have sequences as shown in SEQ ID NO. 129, 130 and 131, respectively;
(26) the CDR1, CDR2 and CDR3 have sequences as shown in SEQ ID NO. 132, 133 and 134, respectively;
(27) the CDR1, CDR2 and CDR3 have sequences as shown in SEQ ID NO. 135, 136 and 137, respectively;
(28) the CDR1, CDR2 and CDR3 have sequences as shown in SEQ ID NO. 138, 139 and 140, respectively;
(29) the CDR1, CDR2 and CDR3 have sequences as shown in SEQ ID NO. 141, 142 and 143, respectively;
(30) the CDR1, CDR2 and CDR3 have sequences as shown in SEQ ID NO. 144, 145 and 146, respectively;
(31) the CDR1, CDR2 and CDR3 have sequences as shown in SEQ ID NO. 147, 148 and 149, respectively;
(32) the CDR1, CDR2 and CDR3 have sequences as shown in SEQ ID NO. 150, 151 and 152, respectively;
(33) the CDR1, CDR2 and CDR3 have sequences as shown in SEQ ID NO. 153, 154 and 155, respectively;
(34) the CDR1, CDR2 and CDR3 have sequences as shown in SEQ ID NO. 156, 157 and 158, respectively;
(35) the CDR1, CDR2 and CDR3 have sequences as shown in SEQ ID NO. 159, 160 and 161, respectively;
(36) the CDR1, CDR2 and CDR3 have sequences as shown in SEQ ID NO. 162, 163 and 164, respectively;
(37) the CDR1, CDR2 and CDR3 have sequences as shown in SEQ ID NO. 165, 166 and 167, respectively;
(38) the CDR1, CDR2 and CDR3 have sequences as shown in SEQ ID NO. 168, 169 and 170, respectively;
(39) the CDR1, CDR2 and CDR3 have sequences as shown in SEQ ID NO. 171, 172 and 173, respectively;
(40) the CDR1, CDR2 and CDR3 have sequences as shown in SEQ ID NO. 174, 175 and 176, respectively;
(41) the CDR1, CDR2 and CDR3 have sequences as shown in SEQ ID NO. 177, 178 and 179, respectively;
(42) the CDR1, CDR2 and CDR3 have sequences as shown in SEQ ID NO. 180, 181 and 182, respectively;
(43) the CDR1, CDR2 and CDR3 have sequences as shown in SEQ ID NO. 183, 184 and 185, respectively;
(44) the CDR1, CDR2 and CDR3 have sequences as shown in SEQ ID NO. 186, 187 and 188, respectively;
(45) the CDR1, CDR2 and CDR3 have sequences as shown in SEQ ID NO. 189, 190 and 191, respectively;
(46) the CDR1, CDR2 and CDR3 have sequences as shown in SEQ ID NO. 192, 193 and 194, respectively;
(47) the CDR1, CDR2 and CDR3 have sequences as shown in SEQ ID NO. 195, 196 and 197, respectively;
(48) the CDR1, CDR2 and CDR3 have sequences as shown in SEQ ID NO. 198, 199 and 200, respectively;
(49) the CDR1, CDR2 and CDR3 have sequences as shown in SEQ ID NO. 201, 202 and 203, respectively;
(50) the CDR1, CDR2 and CDR3 have sequences as shown in SEQ ID NO. 204, 205 and 206, respectively;
(51) the CDR1, CDR2 and CDR3 have sequences as shown in SEQ ID NO. 207, 208 and 209, respectively;
(52) the CDR1, CDR2 and CDR3 have sequences as shown in SEQ ID NO. 210, 211 and 212, respectively;
(53) the CDR1, CDR2 and CDR3 have sequences as shown in SEQ ID NO. 213, 214 and 215, respectively; or
(54) the CDR1, CDR2 and CDR3 have sequences as shown in SEQ ID NO. 216, 217 and 218, respectively.

3. The nanobody or the antigen-binding fragment of claim 1, wherein the nanobody or the antigen-binding fragment comprises:
(1) a variable region having a sequence as shown in SEQ ID NO: 21, or a sequence with 80% or greater identity with SEQ ID NO: 21;
(2) a variable region having a sequence as shown in SEQ ID NO: 23, or a sequence with 80% or greater identity with SEQ ID NO: 23;
(3) a variable region having a sequence as shown in SEQ ID NO: 25, or a sequence with 80% or greater identity with SEQ ID NO: 25;
(4) a variable region having a sequence as shown in SEQ ID NO: 27, or a sequence with 80% or greater identity with SEQ ID NO: 27;
(5) a variable region having a sequence as shown in SEQ ID NO: 29, or a sequence with 80% or greater identity with SEQ ID NO: 29;
(6) a variable region having a sequence as shown in SEQ ID NO: 31, or a sequence with 80% or greater identity with SEQ ID NO: 31;
(7) a variable region having a sequence as shown in SEQ ID NO: 33, or a sequence with 80% or greater identity with SEQ ID NO: 33;
(8) a variable region having a sequence as shown in SEQ ID NO: 35, or a sequence with 80% or greater identity with SEQ ID NO: 35;
(9) a variable region having a sequence as shown in SEQ ID NO: 37, or a sequence with 80% or greater identity with SEQ ID NO: 37;
(10) a variable region having a sequence as shown in SEQ ID NO: 39, or a sequence with 80% or greater identity with SEQ ID NO: 39;
(11) a variable region having a sequence as shown in SEQ ID NO: 41, or a sequence with 80% or greater identity with SEQ ID NO: 41;
(12) a variable region having a sequence as shown in SEQ ID NO: 43, or a sequence with 80% or greater identity with SEQ ID NO: 43;
(13) a variable region having a sequence as shown in SEQ ID NO: 45, or a sequence with 80% or greater identity with SEQ ID NO: 45;
(14) a variable region having a sequence as shown in SEQ ID NO: 47, or a sequence with 80% or greater identity with SEQ ID NO: 47;
(15) a variable region having a sequence as shown in SEQ ID NO: 49, or a sequence with 80% or greater identity with SEQ ID NO: 49;

(16) a variable region having a sequence as shown in SEQ ID NO: 51, or a sequence with 80% or greater identity with SEQ ID NO: 51;

(17) a variable region having a sequence as shown in SEQ ID NO: 53, or a sequence with 80% or greater identity with SEQ ID NO: 53; or,

(18) a variable region having a sequence as shown in SEQ ID NO: 55, or a sequence with 80% or greater identity with SEQ ID NO: 55.

4. The nanobody or the antigen-binding fragment of claim 1, wherein the nanobody or the antigen-binding fragment binds to human CD22 with a dissociation constant (KD) of no more than 50 nM.

5. The nanobody or the antigen-binding fragment of claim 1, wherein the nanobody or the antigen-binding fragment comprises a sequence of the constant region of any one of human or murine antibody IgG1, IgG2, IgG3, IgG4, IgA, IgM, IgE or IgD.

6. The nanobody or the antigen-binding fragment of claim 1, wherein the nanobody or the antigen-binding fragment further comprises a heavy chain constant region sequence without a CH1 fragment.

7. The nanobody or the antigen-binding fragment of claim 1, wherein the nanobody or the antigen-binding fragment further comprises a heavy chain constant region sequence with CH2 and CH3 fragments.

8. The nanobody or the antigen-binding fragment of claim 1, wherein the nanobody or the antigen-binding fragment is further coupled with (i) a therapeutic agent selected from the group consisting of a radioisotope, a chemotherapeutic agent and an immunomodulator or (ii) a tracer selected from the group consisting of a radiological contrast agent, a paramagnetic ion, a metal, a fluorescent label, a chemiluminescence label, a ultrasound contrast agent and a photosensitizer.

9. A multispecific antigen-binding molecule, wherein the multispecific antigen-binding molecule comprises a first antigen-binding module and a second antigen-binding module, wherein the first antigen-binding module comprises the nanobody or the antigen-binding fragment of claim 1, wherein the second antigen-binding module specifically binds to an antigen other than CD22 or binds to a CD22 epitope different from the first antigen-binding module;

wherein the antigen other than CD22 is selected from the group consisting of CD3, CD16, CD16A, CD4, CD5, CD8, CD14, CD15, CD19, CD20, CD21, CD23, CD25, CD33, CD37, CD38, CD40, CD40L, CD46, CD52, CD54, CD66 (a-d), CD74, CD80, CD126, CD138, B7, MUC, Ia, HLA-DR, tenascin, VEGF, P1GF, ED-B fibronectin, oncogene products, IL-2, IL-6, TRAIL-R1 and TRAIL-R2;

wherein the multispecific antigen-binding molecule is a bispecific antibody, a trispecific antibody or a tetraspecific antibody.

10. A chimeric antigen receptor (CAR), wherein the chimeric antigen receptor comprises an extracellular antigen-binding domain, a transmembrane domain and an intracellular signaling domain, wherein the extracellular antigen-binding domain comprises the nanobody or the antigen-binding fragment of claim 1.

11. An immune effector cell, wherein the immune effector cell comprises the chimeric antigen receptor of claim 10 or comprises a nucleic acid fragment encoding the chimeric antigen receptor of claim 10;

wherein the immune effector cell is selected from a NK cell (a natural killer cell), a NKT cell (a natural killer T cell), a monocyte, a macrophage, a dendritic cell, a mast cell, an inflammatory T cell, a cytotoxic T cell, a regulatory T cell (Treg), or a helper T cell;

wherein the immune effector cell is an allogeneic immune effector cell or an autologous immune cell.

12. A method for preparing an immune effector cell comprising:

introducing a nucleic acid fragment encoding the chimeric antigen receptor of claim 10 into the immune effector cell, and enabling the immune effector cell to express the chimeric antigen receptor of claim 10.

13. An isolated nucleic acid molecule, wherein the nucleic acid molecule encodes the nanobody or the antigen-binding fragment of claim 1.

14. An expression vector comprising the isolated nucleic acid molecule of claim 13.

15. An isolated host cell comprising the isolated nucleic acid molecule of claim 13; wherein the host cell is a eukaryotic cell, a prokaryotic cell, a mammalian cell, a yeast cell, an insect cell, an *Escherichia coli* cell, a *Bacillus subtilis* cell, a HEK293E cell, or a CHO cell.

16. A method for preparing the nanobody or the antigen-binding fragment of claim 1 comprising:

culturing a host cell under appropriate conditions, wherein the host cell is an isolated host cell comprising an isolated nucleic acid molecule, and the nucleic acid molecule encodes the nanobody or the antigen-binding fragment, and isolating the nanobody or the antigen-binding fragment from the host cell.

17. A pharmaceutical composition comprising the nanobody or the antigen-binding fragment of claim 1.

18. A method for preventing and/or treating a B-cell disease, wherein the method comprises administering an effective amount of the nanobody or the antigen-binding fragment of claim 1 to a patient in need thereof; wherein the B cell disease is a tumor or an autoimmune disease.

19. The method of claim 18, wherein the B cell disease is a tumor selected from lymphoma, leukemia, B-cell lymphoma, non-Hodgkin's lymphoma, mantle cell lymphoma, follicular lymphoma, marginal zone lymphoma, primary mediastinal B-cell lymphoma, diffuse large B-cell lymphoma, precursor B-cell acute lymphocytic leukemia (pre-B ALL), acute lymphocytic leukemia (ALL), chronic lymphocytic leukemia, and multiple myeloma.

20. The method of claim 18, wherein the B cell disease is an autoimmune disease selected from systemic lupus erythematosus (SLE), antiphospholipid antibody syndrome, multiple sclerosis, ulcerative colitis, Crohn's disease, rheumatoid arthritis, Sjogren's syndrome, Guillain-Barre syndrome, myasthenia gravis, large vessel vasculitis, medium vessel vasculitis, polyarteritis nodosa, pemphigus, scleroderma, pulmonary hemorrhage-nephritic syndrome, glomerular nephritis, primary biliary cirrhosis, Graves' disease, membranous nephropathy, autoimmune hepatitis, sprue, Addison's disease, polymyositis/dermatomyositis, monoclonal gamma globulin disease, factor VIII deficiency, cryoglobulinemia, peripheral neuropathy, IgM polyneuropathy, chronic neuropathy, and chronic lymphocytic thyroiditis.

21. A kit comprising the nanobody or the antigen-binding fragment of claim 1 and instructions for use.

22. The nanobody or the antigen-binding fragment of claim 1, wherein the nanobody or the antigen-binding fragment comprises:

(1) a variable region having a sequence as shown in SEQ ID NO: 21, or a sequence with 95% or greater identity with SEQ ID NO: 21;

(2) a variable region having a sequence as shown in SEQ ID NO: 23, or a sequence with 95% or greater identity with SEQ ID NO: 23;
(3) a variable region having a sequence as shown in SEQ ID NO: 25, or a sequence with 95% or greater identity with SEQ ID NO: 25;
(4) a variable region having a sequence as shown in SEQ ID NO: 27, or a sequence with 95% or greater identity with SEQ ID NO: 27;
(5) a variable region having a sequence as shown in SEQ ID NO: 29, or a sequence with 95% or greater identity with SEQ ID NO: 29;
(6) a variable region having a sequence as shown in SEQ ID NO: 31, or a sequence with 95% or greater identity with SEQ ID NO: 31;
(7) a variable region having a sequence as shown in SEQ ID NO: 33, or a sequence with 95% or greater identity with SEQ ID NO: 33;
(8) a variable region having a sequence as shown in SEQ ID NO: 35, or a sequence with 95% or greater identity with SEQ ID NO: 35;
(9) a variable region having a sequence as shown in SEQ ID NO: 37, or a sequence with 95% or greater identity with SEQ ID NO: 37;
(10) a variable region having a sequence as shown in SEQ ID NO: 39, or a sequence with 95% or greater identity with SEQ ID NO: 39;
(11) a variable region having a sequence as shown in SEQ ID NO: 41, or a sequence with 95% or greater identity with SEQ ID NO: 41;
(12) a variable region having a sequence as shown in SEQ ID NO: 43, or a sequence with 95% or greater identity with SEQ ID NO: 43;
(13) a variable region having a sequence as shown in SEQ ID NO: 45, or a sequence with 95% or greater identity with SEQ ID NO: 45;
(14) a variable region having a sequence as shown in SEQ ID NO: 47, or a sequence with 95% or greater identity with SEQ ID NO: 47;
(15) a variable region having a sequence as shown in SEQ ID NO: 49, or a sequence with 95% or greater identity with SEQ ID NO: 49;
(16) a variable region having a sequence as shown in SEQ ID NO: 51, or a sequence with 95% or greater identity with SEQ ID NO: 51;
(17) a variable region having a sequence as shown in SEQ ID NO: 53, or a sequence with 95% or greater identity with SEQ ID NO: 53; or,
(18) a variable region having a sequence as shown in SEQ ID NO: 55, or a sequence with 95% or greater identity with SEQ ID NO: 55.

* * * * *

SEQUENCE LISTING

<160> NUMBER OF SEQ ID NOS: 218

<210> SEQ ID NO 1
<211> LENGTH: 847
<212> TYPE: PRT
<213> ORGANISM: Artificial sequence
<220> FEATURE:
<223> OTHER INFORMATION: Synthetic

<400> SEQUENCE: 1

Met His Leu Leu Gly Pro Trp Leu Leu Leu Leu Val Leu Glu Tyr Leu

-continued

```
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430
```

```
Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845
```

<210> SEQ ID NO 2
<211> LENGTH: 668
<212> TYPE: PRT
<213> ORGANISM: Artificial sequence
<220> FEATURE:
<223> OTHER INFORMATION: Synthetic

<400> SEQUENCE: 2

```
Asp Ser Ser Lys Trp Val Phe Glu His Pro Glu Thr Leu Tyr Ala Trp
1               5                   10                  15

Glu Gly Ala Cys Val Trp Ile Pro Cys Thr Tyr Arg Ala Leu Asp Gly
            20                  25                  30

Asp Leu Glu Ser Phe Ile Leu Phe His Asn Pro Glu Tyr Asn Lys Asn
        35                  40                  45

Thr Ser Lys Phe Asp Gly Thr Arg Leu Tyr Glu Ser Thr Lys Asp Gly
    50                  55                  60

Lys Val Pro Ser Glu Gln Lys Arg Val Gln Phe Leu Gly Asp Lys Asn
65                  70                  75                  80

Lys Asn Cys Thr Leu Ser Ile His Pro Val His Leu Asn Asp Ser Gly
                85                  90                  95

Gln Leu Gly Leu Arg Met Glu Ser Lys Thr Glu Lys Trp Met Glu Arg
            100                 105                 110

Ile His Leu Asn Val Ser Glu Arg Pro Phe Pro Pro His Ile Gln Leu
        115                 120                 125

Pro Pro Glu Ile Gln Glu Ser Gln Glu Val Thr Leu Thr Cys Leu Leu
    130                 135                 140

Asn Phe Ser Cys Tyr Gly Tyr Pro Ile Gln Leu Gln Trp Leu Leu Glu
145                 150                 155                 160

Gly Val Pro Met Arg Gln Ala Ala Val Thr Ser Thr Ser Leu Thr Ile
                165                 170                 175

Lys Ser Val Phe Thr Arg Ser Glu Leu Lys Phe Ser Pro Gln Trp Ser
            180                 185                 190

His His Gly Lys Ile Val Thr Cys Gln Leu Gln Asp Ala Asp Gly Lys
        195                 200                 205

Phe Leu Ser Asn Asp Thr Val Gln Leu Asn Val Lys His Thr Pro Lys
    210                 215                 220

Leu Glu Ile Lys Val Thr Pro Ser Asp Ala Ile Val Arg Glu Gly Asp
225                 230                 235                 240

Ser Val Thr Met Thr Cys Glu Val Ser Ser Ser Asn Pro Glu Tyr Thr
                245                 250                 255

Thr Val Ser Trp Leu Lys Asp Gly Thr Ser Leu Lys Lys Gln Asn Thr
            260                 265                 270

Phe Thr Leu Asn Leu Arg Glu Val Thr Lys Asp Gln Ser Gly Lys Tyr
        275                 280                 285

Cys Cys Gln Val Ser Asn Asp Val Gly Pro Gly Arg Ser Glu Glu Val
    290                 295                 300

Phe Leu Gln Val Gln Tyr Ala Pro Glu Pro Ser Thr Val Gln Ile Leu
305                 310                 315                 320

His Ser Pro Ala Val Glu Gly Ser Gln Val Glu Phe Leu Cys Met Ser
                325                 330                 335

Leu Ala Asn Pro Leu Pro Thr Asn Tyr Thr Trp Tyr His Asn Gly Lys
            340                 345                 350

Glu Met Gln Gly Arg Thr Glu Glu Lys Val His Ile Pro Lys Ile Leu
        355                 360                 365
```

```
Pro Trp His Ala Gly Thr Tyr Ser Cys Val Ala Glu Asn Ile Leu Gly
    370                 375                 380

Thr Gly Gln Arg Gly Pro Gly Ala Glu Leu Asp Val Gln Tyr Pro Pro
385                 390                 395                 400

Lys Lys Val Thr Thr Val Ile Gln Asn Pro Met Pro Ile Arg Glu Gly
                405                 410                 415

Asp Thr Val Thr Leu Ser Cys Asn Tyr Asn Ser Ser Asn Pro Ser Val
            420                 425                 430

Thr Arg Tyr Glu Trp Lys Pro His Gly Ala Trp Glu Glu Pro Ser Leu
        435                 440                 445

Gly Val Leu Lys Ile Gln Asn Val Gly Trp Asp Asn Thr Thr Ile Ala
    450                 455                 460

Cys Ala Ala Cys Asn Ser Trp Cys Ser Trp Ala Ser Pro Val Ala Leu
465                 470                 475                 480

Asn Val Gln Tyr Ala Pro Arg Asp Val Arg Val Arg Lys Ile Lys Pro
                485                 490                 495

Leu Ser Glu Ile His Ser Gly Asn Ser Val Ser Leu Gln Cys Asp Phe
            500                 505                 510

Ser Ser Ser His Pro Lys Glu Val Gln Phe Phe Trp Glu Lys Asn Gly
        515                 520                 525

Arg Leu Leu Gly Lys Glu Ser Gln Leu Asn Phe Asp Ser Ile Ser Pro
    530                 535                 540

Glu Asp Ala Gly Ser Tyr Ser Cys Trp Val Asn Asn Ser Ile Gly Gln
545                 550                 555                 560

Thr Ala Ser Lys Ala Trp Thr Leu Glu Val Leu Tyr Ala Pro Arg Arg
                565                 570                 575

Leu Arg Val Ser Met Ser Pro Gly Asp Gln Val Met Glu Gly Lys Ser
            580                 585                 590

Ala Thr Leu Thr Cys Glu Ser Asp Ala Asn Pro Pro Val Ser His Tyr
        595                 600                 605

Thr Trp Phe Asp Trp Asn Asn Gln Ser Leu Pro Tyr His Ser Gln Lys
    610                 615                 620

Leu Arg Leu Glu Pro Val Lys Val Gln His Ser Gly Ala Tyr Trp Cys
625                 630                 635                 640

Gln Gly Thr Asn Ser Val Gly Lys Gly Arg Ser Pro Leu Ser Thr Leu
                645                 650                 655

Thr Val Tyr Tyr Ser Pro Glu Thr Ile Gly Arg Arg
            660                 665


<210> SEQ ID NO 3
<211> LENGTH: 406
<212> TYPE: PRT
<213> ORGANISM: Artificial sequence
<220> FEATURE:
<223> OTHER INFORMATION: Synthetic

<400> SEQUENCE: 3

Asp Ser Ser Lys Trp Val Phe Glu His Pro Glu Thr Leu Tyr Ala Trp
1               5                   10                  15

Glu Gly Ala Cys Val Trp Ile Pro Cys Thr Tyr Arg Ala Leu Asp Gly
            20                  25                  30

Asp Leu Glu Ser Phe Ile Leu Phe His Asn Pro Glu Tyr Asn Lys Asn
        35                  40                  45

Thr Ser Lys Phe Asp Gly Thr Arg Leu Tyr Glu Ser Thr Lys Asp Gly
    50                  55                  60
```

Lys Val Pro Ser Glu Gln Lys Arg Val Gln Phe Leu Gly Asp Lys Asn
65 70 75 80

Lys Asn Cys Thr Leu Ser Ile His Pro Val His Leu Asn Asp Ser Gly
85 90 95

Gln Leu Gly Leu Arg Met Glu Ser Lys Thr Glu Lys Trp Met Glu Arg
100 105 110

Ile His Leu Asn Val Ser Glu Arg Pro Phe Pro Pro His Ile Gln Leu
115 120 125

Pro Pro Glu Ile Gln Glu Ser Gln Glu Val Thr Leu Thr Cys Leu Leu
130 135 140

Asn Phe Ser Cys Tyr Gly Tyr Pro Ile Gln Leu Gln Trp Leu Leu Glu
145 150 155 160

Gly Val Pro Met Arg Gln Ala Ala Val Thr Ser Thr Ser Leu Thr Ile
165 170 175

Lys Ser Val Phe Thr Arg Ser Glu Leu Lys Phe Ser Pro Gln Trp Ser
180 185 190

His His Gly Lys Ile Val Thr Cys Gln Leu Gln Asp Ala Asp Gly Lys
195 200 205

Phe Leu Ser Asn Asp Thr Val Gln Leu Asn Val Lys His Thr Pro Lys
210 215 220

Leu Glu Ile Lys Val Thr Pro Ser Asp Ala Ile Val Arg Glu Gly Asp
225 230 235 240

Ser Val Thr Met Thr Cys Glu Val Ser Ser Ser Asn Pro Glu Tyr Thr
245 250 255

Thr Val Ser Trp Leu Lys Asp Gly Thr Ser Leu Lys Lys Gln Asn Thr
260 265 270

Phe Thr Leu Asn Leu Arg Glu Val Thr Lys Asp Gln Ser Gly Lys Tyr
275 280 285

Cys Cys Gln Val Ser Asn Asp Val Gly Pro Gly Arg Ser Glu Glu Val
290 295 300

Phe Leu Gln Val Gln Tyr Ala Pro Glu Pro Ser Thr Val Gln Ile Leu
305 310 315 320

His Ser Pro Ala Val Glu Gly Ser Gln Val Glu Phe Leu Cys Met Ser
325 330 335

Leu Ala Asn Pro Leu Pro Thr Asn Tyr Thr Trp Tyr His Asn Gly Lys
340 345 350

Glu Met Gln Gly Arg Thr Glu Glu Lys Val His Ile Pro Lys Ile Leu
355 360 365

Pro Trp His Ala Gly Thr Tyr Ser Cys Val Ala Glu Asn Ile Leu Gly
370 375 380

Thr Gly Gln Arg Gly Pro Gly Ala Glu Leu Asp Val Gln Tyr Pro Pro
385 390 395 400

Lys Lys Val Thr Thr Val
405

<210> SEQ ID NO 4
<211> LENGTH: 274
<212> TYPE: PRT
<213> ORGANISM: Artificial sequence
<220> FEATURE:
<223> OTHER INFORMATION: Synthetic

<400> SEQUENCE: 4

Asp Val Gln Tyr Pro Pro Lys Lys Val Thr Thr Val Ile Gln Asn Pro
1 5 10 15

```
Met Pro Ile Arg Glu Gly Asp Thr Val Thr Leu Ser Cys Asn Tyr Asn
            20                  25                  30

Ser Ser Asn Pro Ser Val Thr Arg Tyr Glu Trp Lys Pro His Gly Ala
        35                  40                  45

Trp Glu Glu Pro Ser Leu Gly Val Leu Lys Ile Gln Asn Val Gly Trp
    50                  55                  60

Asp Asn Thr Thr Ile Ala Cys Ala Ala Cys Asn Ser Trp Cys Ser Trp
65                  70                  75                  80

Ala Ser Pro Val Ala Leu Asn Val Gln Tyr Ala Pro Arg Asp Val Arg
                85                  90                  95

Val Arg Lys Ile Lys Pro Leu Ser Glu Ile His Ser Gly Asn Ser Val
            100                 105                 110

Ser Leu Gln Cys Asp Phe Ser Ser Ser His Pro Lys Glu Val Gln Phe
        115                 120                 125

Phe Trp Glu Lys Asn Gly Arg Leu Leu Gly Lys Glu Ser Gln Leu Asn
    130                 135                 140

Phe Asp Ser Ile Ser Pro Glu Asp Ala Gly Ser Tyr Ser Cys Trp Val
145                 150                 155                 160

Asn Asn Ser Ile Gly Gln Thr Ala Ser Lys Ala Trp Thr Leu Glu Val
                165                 170                 175

Leu Tyr Ala Pro Arg Arg Leu Arg Val Ser Met Ser Pro Gly Asp Gln
            180                 185                 190

Val Met Glu Gly Lys Ser Ala Thr Leu Thr Cys Glu Ser Asp Ala Asn
        195                 200                 205

Pro Pro Val Ser His Tyr Thr Trp Phe Asp Trp Asn Asn Gln Ser Leu
    210                 215                 220

Pro Tyr His Ser Gln Lys Leu Arg Leu Glu Pro Val Lys Val Gln His
225                 230                 235                 240

Ser Gly Ala Tyr Trp Cys Gln Gly Thr Asn Ser Val Gly Lys Gly Arg
                245                 250                 255

Ser Pro Leu Ser Thr Leu Thr Val Tyr Tyr Ser Pro Glu Thr Ile Gly
            260                 265                 270

Arg Arg
```

<210> SEQ ID NO 5
<211> LENGTH: 123
<212> TYPE: PRT
<213> ORGANISM: Artificial sequence
<220> FEATURE:
<223> OTHER INFORMATION: Synthetic

<400> SEQUENCE: 5

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Cys Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Thr His Trp Gly Val Leu Phe Ala Tyr
```

```
            100                 105                 110

Trp Gly Gln Gly Thr Leu Val Thr Val Ser Ala
        115                 120


<210> SEQ ID NO 6
<211> LENGTH: 107
<212> TYPE: PRT
<213> ORGANISM: Artificial sequence
<220> FEATURE:
<223> OTHER INFORMATION: Synthetic

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Cys Gly Thr Lys Leu Glu Ile Lys
            100                 105


<210> SEQ ID NO 7
<211> LENGTH: 477
<212> TYPE: PRT
<213> ORGANISM: Artificial sequence
<220> FEATURE:
<223> OTHER INFORMATION: Synthetic

<400> SEQUENCE: 7

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Cys Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Thr His Trp Gly Val Leu Phe Ala Tyr
            100                 105                 110

Trp Gly Gln Gly Thr Leu Val Thr Val Ser Ala Gly Gly Gly Gly Ser
        115                 120                 125

Gly Gly Gly Gly Ser Gly Gly Gly Gly Ser Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Asn Tyr Leu Asn Trp Tyr Gln Gln
                165                 170                 175
```

```
Lys Pro Asp Gly Thr Val Lys Leu Leu Ile Tyr Tyr Thr Ser Ile Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Phe Ala Thr Tyr
    210                 215                 220

Phe Cys Gln Gln Gly Asn Thr Leu Pro Trp Thr Phe Gly Cys Gly Thr
225                 230                 235                 240

Lys Leu Glu Ile Lys Glu Pro Lys Ser Ala Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475
```

<210> SEQ ID NO 8
<211> LENGTH: 124
<212> TYPE: PRT
<213> ORGANISM: Artificial sequence
<220> FEATURE:
<223> OTHER INFORMATION: Synthetic

<400> SEQUENCE: 8

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60
```

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Val Thr Gly Asp Leu Glu Asp Ala Phe Asp
100 105 110

Ile Trp Gly Gln Gly Thr Met Val Thr Val Ser Ser
115 120

<210> SEQ ID NO 9
<211> LENGTH: 107
<212> TYPE: PRT
<213> ORGANISM: Artificial sequence
<220> FEATURE:
<223> OTHER INFORMATION: Synthetic

<400> SEQUENCE: 9

Asp Ile Gln Met Thr Gln Ser Pro Ser Ser Leu Ser Ala Ser Val Gly
1 5 10 15

Asp Arg Val Thr Ile Thr Cys Arg Ala Ser Gln Thr Ile Trp Ser Tyr
20 25 30

Leu Asn Trp Tyr Gln Gln Arg Pro Gly Lys Ala Pro Asn Leu Leu Ile
35 40 45

Tyr Ala Ala Ser Ser Leu Gln Ser Gly Val Pro Ser Arg Phe Ser Gly
50 55 60

Arg Gly Ser Gly Thr Asp Phe Thr Leu Thr Ile Ser Ser Leu Gln Ala
65 70 75 80

Glu Asp Phe Ala Thr Tyr Tyr Cys Gln Gln Ser Tyr Ser Ile Pro Gln
85 90 95

Thr Phe Gly Gln Gly Thr Lys Leu Glu Ile Lys
100 105

<210> SEQ ID NO 10
<211> LENGTH: 478
<212> TYPE: PRT
<213> ORGANISM: Artificial sequence
<220> FEATURE:
<223> OTHER INFORMATION: Synthetic

<400> SEQUENCE: 10

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Val Thr Gly Asp Leu Glu Asp Ala Phe Asp
100 105 110

Ile Trp Gly Gln Gly Thr Met Val Thr Val Ser Ser Gly Gly Gly Gly
115 120 125

Ser Gly Gly Gly Gly Ser Gly Gly Gly Gly Ser Asp Ile Gln Met Thr
130 135 140

Gln Ser Pro Ser Ser Leu Ser Ala Ser Val Gly Asp Arg Val Thr Ile
145 150 155 160

Thr Cys Arg Ala Ser Gln Thr Ile Trp Ser Tyr Leu Asn Trp Tyr Gln
165 170 175

Gln Arg Pro Gly Lys Ala Pro Asn Leu Leu Ile Tyr Ala Ala Ser Ser
180 185 190

Leu Gln Ser Gly Val Pro Ser Arg Phe Ser Gly Arg Gly Ser Gly Thr
195 200 205

Asp Phe Thr Leu Thr Ile Ser Ser Leu Gln Ala Glu Asp Phe Ala Thr
210 215 220

Tyr Tyr Cys Gln Gln Ser Tyr Ser Ile Pro Gln Thr Phe Gly Gln Gly
225 230 235 240

Thr Lys Leu Glu Ile Lys Glu Pro Lys Ser Ala Asp Lys Thr His Thr
245 250 255

Cys Pro Pro Cys Pro Ala Pro Glu Leu Leu Gly Gly Pro Ser Val Phe
260 265 270

Leu Phe Pro Pro Lys Pro Lys Asp Thr Leu Met Ile Ser Arg Thr Pro
275 280 285

Glu Val Thr Cys Val Val Val Asp Val Ser His Glu Asp Pro Glu Val
290 295 300

Lys Phe Asn Trp Tyr Val Asp Gly Val Glu Val His Asn Ala Lys Thr
305 310 315 320

Lys Pro Arg Glu Glu Gln Tyr Asn Ser Thr Tyr Arg Val Val Ser Val
325 330 335

Leu Thr Val Leu His Gln Asp Trp Leu Asn Gly Lys Glu Tyr Lys Cys
340 345 350

Lys Val Ser Asn Lys Ala Leu Pro Ala Pro Ile Glu Lys Thr Ile Ser
355 360 365

Lys Ala Lys Gly Gln Pro Arg Glu Pro Gln Val Tyr Thr Leu Pro Pro
370 375 380

Ser Arg Glu Glu Met Thr Lys Asn Gln Val Ser Leu Thr Cys Leu Val
385 390 395 400

Lys Gly Phe Tyr Pro Ser Asp Ile Ala Val Glu Trp Glu Ser Asn Gly
405 410 415

Gln Pro Glu Asn Asn Tyr Lys Thr Thr Pro Pro Val Leu Asp Ser Asp
420 425 430

Gly Ser Phe Phe Leu Tyr Ser Lys Leu Thr Val Asp Lys Ser Arg Trp
435 440 445

Gln Gln Gly Asn Val Phe Ser Cys Ser Val Met His Glu Ala Leu His
450 455 460

Asn His Tyr Thr Gln Lys Ser Leu Ser Leu Ser Pro Gly Lys
465 470 475

<210> SEQ ID NO 11
<211> LENGTH: 116
<212> TYPE: PRT
<213> ORGANISM: Artificial sequence
<220> FEATURE:
<223> OTHER INFORMATION: Synthetic

<400> SEQUENCE: 11

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

```
Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115


<210> SEQ ID NO 12
<211> LENGTH: 112
<212> TYPE: PRT
<213> ORGANISM: Artificial sequence
<220> FEATURE:
<223> OTHER INFORMATION: Synthetic

<400> SEQUENCE: 12

Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110


<210> SEQ ID NO 13
<211> LENGTH: 475
<212> TYPE: PRT
<213> ORGANISM: Artificial sequence
<220> FEATURE:
<223> OTHER INFORMATION: Synthetic

<400> SEQUENCE: 13

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
```

```
            100                 105                 110

Thr Val Ser Ser Gly Gly Gly Gly Ser Gly Gly Gly Gly Ser Gly Gly
        115                 120                 125

Gly Gly Ser Asp Ile Gln Leu Thr Gln Ser Pro Ser Ser Leu Ser Ala
    130                 135                 140

Ser Val Gly Asp Arg Val Thr Met Ser Cys Lys Ser Ser Gln Ser Val
145                 150                 155                 160

Leu Tyr Ser Ala Asn His Lys Asn Tyr Leu Ala Trp Tyr Gln Gln Lys
                165                 170                 175

Pro Gly Lys Ala Pro Lys Leu Leu Ile Tyr Trp Ala Ser Thr Arg Glu
            180                 185                 190

Ser Gly Val Pro Ser Arg Phe Ser Gly Ser Gly Ser Gly Thr Asp Phe
        195                 200                 205

Thr Phe Thr Ile Ser Ser Leu Gln Pro Glu Asp Ile Ala Thr Tyr Tyr
    210                 215                 220

Cys His Gln Tyr Leu Ser Ser Trp Thr Phe Gly Gly Gly Thr Lys Leu
225                 230                 235                 240

Glu Ile Lys Glu Pro Lys Ser Ala Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 14
<211> LENGTH: 217
<212> TYPE: PRT
<213> ORGANISM: Artificial sequence
<220> FEATURE:
<223> OTHER INFORMATION: Synthetic

<400> SEQUENCE: 14

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 15
<211> LENGTH: 15
<212> TYPE: PRT
<213> ORGANISM: Artificial sequence
<220> FEATURE:
<223> OTHER INFORMATION: Synthetic

<400> SEQUENCE: 15

Glu Pro Lys Ser Ala Asp Lys Thr His Thr Cys Pro Pro Cys Pro
1 5 10 15

<210> SEQ ID NO 16
<211> LENGTH: 18
<212> TYPE: DNA
<213> ORGANISM: Artificial sequence
<220> FEATURE:
<223> OTHER INFORMATION: Synthetic

<400> SEQUENCE: 16
cttggtggtc ctggctgc 18

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
ggtacgtgct gttgaactgt tcc 23

<210> SEQ ID NO 18
<211> LENGTH: 47
<212> TYPE: DNA
<213> ORGANISM: Artificial sequence
<220> FEATURE:
<223> OTHER INFORMATION: Synthetic

<400> SEQUENCE: 18
catgccatga ctgtggccca ggcggcccag ktgcagctcg tggagtc 47

<210> SEQ ID NO 19
<211> LENGTH: 51
<212> TYPE: DNA
<213> ORGANISM: Artificial sequence
<220> FEATURE:
<223> OTHER INFORMATION: Synthetic

<400> SEQUENCE: 19
catgccatga ctcgcggccg gcctggccat gggggtcttc gctgtggtgc g 51

<210> SEQ ID NO 20
<211> LENGTH: 52
<212> TYPE: DNA
<213> ORGANISM: Artificial sequence
<220> FEATURE:
<223> OTHER INFORMATION: Synthetic

<400> SEQUENCE: 20
catgccatga ctcgcggccg gcctggccgt cttgtggttt tggtgtcttg gg 52

<210> SEQ ID NO 21
<211> LENGTH: 121
<212> TYPE: PRT
<213> ORGANISM: Artificial sequence
<220> FEATURE:
<223> OTHER INFORMATION: Synthetic

<400> SEQUENCE: 21

```
Gln Val Gln Leu Val Glu Ser Gly Gly Gly Leu Val Gln Ala Gly Asp
1               5                   10                  15

Ser Leu Lys Leu Ser Cys Leu Ala Ser Gly Ile Thr Phe Ser Ser Tyr
            20                  25                  30

Tyr Met Ser Trp Phe Arg Gln Ala Pro Gly Lys Glu Arg Glu Phe Val
        35                  40                  45

Ala Gly Val Gly Arg Ser Gly Ala Pro Ser His His Ala Asp Ser Val
    50                  55                  60

Lys Gly Arg Phe Thr Ile Ser Arg Asp Asn Ala Lys Ser Ala Val Tyr
65                  70                  75                  80

Leu Gln Met Asn Ser Leu Gln Pro Glu Asp Thr Ala Val Tyr Phe Cys
                85                  90                  95

Ala Ala Lys Trp Met Ala Ala Ser Thr Thr Val Ala Asp Tyr Trp Gly
            100                 105                 110

Gln Gly Thr Gln Val Thr Val Ser Ser
        115                 120
```

<210> SEQ ID NO 22
<211> LENGTH: 363
<212> TYPE: DNA
<213> ORGANISM: Artificial sequence
<220> FEATURE:
<223> OTHER INFORMATION: Synthetic

<400> SEQUENCE: 22
caggtgcagc tggtggagag cggcggcggc ctggtgcagg ccggcgacag cctgaagctg 60
agctgcctgg ccagcggcat caccttcagc agctactaca tgagctggtt caggcaggcc 120
cccggcaagg agagggagtt cgtggccggc gtgggcagga gcggcgcccc cagccaccac 180
gccgacagcg tgaagggcag gttcaccatc agcagggaca acgccaagag cgccgtgtac 240
ctgcagatga acagcctgca gcccgaggac accgccgtgt acttctgcgc cgccaagtgg 300
atggccgcca gcaccaccgt ggccgactac tggggccagg gcacccaggt gaccgtgagc 360
agc 363

<210> SEQ ID NO 23
<211> LENGTH: 125
<212> TYPE: PRT
<213> ORGANISM: Artificial sequence
<220> FEATURE:
<223> OTHER INFORMATION: Synthetic

<400> SEQUENCE: 23

Gln Leu Gln Leu Val Glu Ser Gly Gly Gly Leu Val Gln Ala Gly Gly
1 5 10 15

Ser Leu Arg Leu Ser Cys Val Gly Ser Gly Asp Arg Val Ser Ile Ala
20 25 30

Leu Met Gly Trp Phe Arg Gln Ala Pro Gly Lys Glu Arg Glu Phe Val
35 40 45

Ala Ala Ile Ser Pro Ser Gly Gly Arg Ile Thr Tyr Ser Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Arg Asp Asp Thr Ala Val Tyr Val Cys
85 90 95

Ala Ala Asn Phe Arg Gly Tyr Leu Ser Ser Ser Arg Gly Ser Asp Tyr
100 105 110

Ala Tyr Trp Gly Gln Gly Thr Gln Val Thr Val Ser Ser
115 120 125

<210> SEQ ID NO 24
<211> LENGTH: 375
<212> TYPE: DNA
<213> ORGANISM: Artificial sequence
<220> FEATURE:
<223> OTHER INFORMATION: Synthetic

<400> SEQUENCE: 24
cagctgcagc tggtggagag cggcggcggc ctggtgcagg ccggcggcag cctgaggctg 60
agctgcgtgg gcagcggcga cagggtgagc atcgccctga tgggctggtt caggcaggcc 120
cccggcaagg agagggagtt cgtggccgcc atcagcccca gcggcggcag gatcacctac 180
agcgacagcg tgaagggcag gttcaccatc agcagggaca acgccaagaa caccgtgtac 240
ctgcagatga acagcctgaa gagggacgac accgccgtgt acgtgtgcgc cgccaacttc 300
aggggctacc tgagcagcag caggggcagc gactacgcct actggggcca gggcacccag 360
gtgaccgtga gcagc 375

<210> SEQ ID NO 25
<211> LENGTH: 124
<212> TYPE: PRT

<213> ORGANISM: Artificial sequence
<220> FEATURE:
<223> OTHER INFORMATION: Synthetic

<400> SEQUENCE: 25

Gln Val Gln Leu Val Glu Ser Gly Gly Gly Leu Val Gln Asp Gly Gly
1 5 10 15

Ser Leu Arg Leu Ser Cys Ala Ala Ser Gly Leu Thr Phe Ser Phe Tyr
20 25 30

Asn Met Gly Trp Phe Arg Gln Ala Pro Gly Lys Glu Arg Glu Phe Val
35 40 45

Ala Ala Ile Ser Gln Ser Gly Leu Ser Thr His Tyr Ala Asp Ser Met
50 55 60

Lys Gly Arg Phe Thr Ile Ser Arg Asp Asn Ala Lys Asn Thr Val Tyr
65 70 75 80

Leu Gln Met Asn Ser Leu Asn Pro Val Asp Thr Ala Ala Tyr Tyr Cys
85 90 95

Ala Ala Gly Arg Arg Gly Tyr Leu Ala Ser Thr Thr Asn Asp Tyr Glu
100 105 110

Tyr Trp Gly Gln Gly Thr Gln Val Thr Val Ser Ser
115 120

<210> SEQ ID NO 26
<211> LENGTH: 372
<212> TYPE: DNA
<213> ORGANISM: Artificial sequence
<220> FEATURE:
<223> OTHER INFORMATION: Synthetic

<400> SEQUENCE: 26
caggtgcagc tggtggagag cggcggcggc ctggtgcagg acggcggcag cctgaggctg 60
agctgcgccg ccagcggcct gaccttcagc ttctacaaca tgggctggtt caggcaggcc 120
cccggcaagg agagggagtt cgtggccgcc atcagccaga gcggcctgag cacccactac 180
gccgacagca tgaagggcag gttcaccatc agcagggaca acgccaagaa caccgtgtac 240
ctgcagatga acagcctgaa ccccgtggac accgccgcct actactgcgc cgccggcagg 300
aggggctacc tggccagcac caccaacgac tacgagtact ggggccaggg cacccaggtg 360
accgtgagca gc 372

<210> SEQ ID NO 27
<211> LENGTH: 128
<212> TYPE: PRT
<213> ORGANISM: Artificial sequence
<220> FEATURE:
<223> OTHER INFORMATION: Synthetic

<400> SEQUENCE: 27

Gln Val Gln Leu Val Glu Ser Gly Gly Gly Leu Val Gln Ala Gly Asp
1 5 10 15

Ser Leu Arg Leu Ser Cys Ala Val Thr Gly Arg Ala Tyr Ser Arg Ser
20 25 30

Asp Met Gly Trp Phe Arg Gln Ala Pro Gly Lys Glu Arg Glu Ile Val
35 40 45

Ala Val Ile Thr Phe Gly Gly Gly Thr Asp Tyr Ala Asp Ser Val Lys
50 55 60

Gly Arg Phe Thr Ile Ser Ser Glu Asp Thr Lys Asn Thr Leu Tyr Leu
65 70 75 80

```
Gln Met Asn Ser Leu Gln Pro Glu Asp Thr Ala Val Tyr Tyr Cys Ala
                85                  90                  95

Ala Gly Phe Arg Gly Ser Arg Trp Ser Thr Ala Ala Arg Arg Lys Glu
            100                 105                 110

Asp Asp Tyr Ala Phe Trp Gly Gln Gly Thr Gln Val Thr Val Ser Ser
        115                 120                 125


<210> SEQ ID NO 28
<211> LENGTH: 384
<212> TYPE: PRT
<213> ORGANISM: Artificial sequence
<220> FEATURE:
<223> OTHER INFORMATION: Synthetic

<400> SEQUENCE: 28

Cys Ala Gly Gly Thr Gly Cys Ala Gly Cys Thr Gly Gly Thr Gly Gly
1               5                   10                  15

Ala Gly Ala Gly Cys Gly Gly Cys Gly Gly Cys Gly Gly Cys Cys Thr
            20                  25                  30

Gly Gly Thr Gly Cys Ala Gly Gly Cys Cys Gly Gly Cys Gly Ala Cys
        35                  40                  45

Ala Gly Cys Cys Thr Gly Ala Gly Gly Cys Thr Gly Ala Gly Cys Thr
    50                  55                  60

Gly Cys Gly Cys Cys Gly Thr Gly Ala Cys Cys Gly Gly Cys Ala Gly
65                  70                  75                  80

Gly Gly Cys Cys Thr Ala Cys Ala Gly Cys Ala Gly Gly Ala Gly Cys
                85                  90                  95

Gly Ala Cys Ala Thr Gly Gly Gly Cys Thr Gly Gly Thr Thr Cys Ala
            100                 105                 110

Gly Gly Cys Ala Gly Gly Cys Cys Cys Cys Cys Gly Gly Cys Ala Ala
        115                 120                 125

Gly Gly Ala Gly Ala Gly Gly Gly Ala Gly Ala Thr Cys Gly Thr Gly
    130                 135                 140

Gly Cys Cys Gly Thr Gly Ala Thr Cys Ala Cys Cys Thr Thr Cys Gly
145                 150                 155                 160

Gly Cys Gly Gly Cys Gly Gly Cys Ala Cys Cys Gly Ala Cys Thr Ala
                165                 170                 175

Cys Gly Cys Cys Gly Ala Cys Ala Gly Cys Gly Thr Gly Ala Ala Gly
            180                 185                 190

Gly Gly Cys Ala Gly Gly Thr Thr Cys Ala Cys Cys Ala Thr Cys Ala
        195                 200                 205

Gly Cys Ala Gly Cys Gly Ala Gly Gly Ala Cys Ala Cys Cys Ala Ala
    210                 215                 220

Gly Ala Ala Cys Ala Cys Cys Cys Thr Gly Thr Ala Cys Cys Thr Gly
225                 230                 235                 240

Cys Ala Gly Ala Thr Gly Ala Ala Cys Ala Gly Cys Cys Thr Gly Cys
                245                 250                 255

Ala Gly Cys Cys Cys Gly Ala Gly Gly Ala Cys Ala Cys Cys Gly Cys
            260                 265                 270

Cys Gly Thr Gly Thr Ala Cys Thr Ala Cys Thr Gly Cys Gly Cys Cys
        275                 280                 285

Gly Cys Cys Gly Gly Cys Thr Thr Cys Ala Gly Gly Gly Gly Cys Ala
    290                 295                 300

Gly Cys Ala Gly Gly Thr Gly Gly Ala Gly Cys Ala Cys Cys Gly Cys
305                 310                 315                 320
```

```
Cys Gly Cys Cys Ala Gly Gly Ala Gly Gly Ala Ala Gly Gly Ala Gly
                325                 330                 335

Gly Ala Cys Gly Ala Cys Thr Ala Cys Gly Cys Cys Thr Thr Cys Thr
            340                 345                 350

Gly Gly Gly Gly Cys Cys Ala Gly Gly Gly Cys Ala Cys Cys Cys Ala
        355                 360                 365

Gly Gly Thr Gly Ala Cys Cys Gly Thr Gly Ala Gly Cys Ala Gly Cys
    370                 375                 380
```

<210> SEQ ID NO 29
<211> LENGTH: 124
<212> TYPE: PRT
<213> ORGANISM: Artificial sequence
<220> FEATURE:
<223> OTHER INFORMATION: Synthetic

<400> SEQUENCE: 29

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Trp Phe Asn Ile Ala
            20                  25                  30

Met Gly Trp Phe Arg Gln Ala Pro Gly Lys Glu Arg Glu Phe Val Ala
        35                  40                  45

Gly Ile Arg Trp Ser Asp Ser Lys Thr Tyr Tyr Ala Asp Ser Val Lys
    50                  55                  60

Gly Arg Phe Thr Ile Ser Gly Asp Asn Ala Lys Asn Thr Thr Tyr Leu
65                  70                  75                  80

Gln Met Asn Ser Leu Lys Pro Glu Asp Thr Ala Val Tyr Tyr Cys Ala
                85                  90                  95

Ala Gln Arg Tyr Tyr Arg Gly Ser Tyr Asn Arg Gln Thr Asn Tyr Asp
            100                 105                 110

His Trp Gly Gln Gly Thr Gln Val Thr Val Ser Ser
        115                 120
```

<210> SEQ ID NO 30
<211> LENGTH: 372
<212> TYPE: DNA
<213> ORGANISM: Artificial sequence
<220> FEATURE:
<223> OTHER INFORMATION: Synthetic

<400> SEQUENCE: 30

```
caggtgcagc tggtggagag cggcggcggc ctggtgcagc ccggcggcag cctgaggctg      60

agctgcgccg ccagcggcag ctggttcaac atcgccatgg gctggttcag gcaggccccc     120

ggcaaggaga gggagttcgt ggccggcatc aggtggagcg acagcaagac ctactacgcc     180

gacagcgtga agggcaggtt caccatcagc ggcgacaacg ccaagaacac cacctacctg     240

cagatgaaca gcctgaagcc cgaggacacc gccgtgtact actgcgccgc ccagaggtac     300

tacaggggca gctacaacag gcagaccaac tacgaccact ggggccaggg cacccaggtg     360

accgtgagca gc                                                         372
```

<210> SEQ ID NO 31
<211> LENGTH: 127
<212> TYPE: PRT
<213> ORGANISM: Artificial sequence
<220> FEATURE:
<223> OTHER INFORMATION: Synthetic

<400> SEQUENCE: 31

Gln Val Gln Leu Val Glu Ser Gly Gly Gly Leu Val Gln Ala Gly Gly
1               5                   10                  15

Ser Leu Arg Leu Ser Cys Thr Thr Ser Gly Gly Thr Leu Ser Arg Ile
            20                  25                  30

Thr Met Gly Trp Phe Arg Gln Ala Pro Gly Lys Glu Arg Glu Phe Val
        35                  40                  45

Ala Ala Ile Lys Trp Gly Gly Ser Ser Thr Pro Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Arg Leu Val Pro Glu Asp Thr Ala Val Tyr Tyr Cys
                85                  90                  95

Ala Gly Gly Leu Arg Gly Pro Tyr Ser Asp Ser Val Thr Ser Ser Val
            100                 105                 110

Gln Tyr Asn Tyr Trp Gly Gln Gly Thr Gln Val Thr Val Ser Ser
        115                 120                 125

<210> SEQ ID NO 32
<211> LENGTH: 381
<212> TYPE: DNA
<213> ORGANISM: Artificial sequence
<220> FEATURE:
<223> OTHER INFORMATION: Synthetic

<400> SEQUENCE: 32
caggtgcagc tggtggagag cggcggcggc ctggtgcagg ccggcggcag cctgaggctg 60
agctgcacca ccagcggcgg caccctgagc aggatcacca tgggctggtt caggcaggcc 120
cccggcaagg agagggagtt cgtggccgcc atcaagtggg gcggcagcag cacccccctac 180 agcgacagcg tgaagggcag gttcaccatc agcagggaca acgccaagaa caccgtgtac 240
ctgcagatgg acaggctggt gcccgaggac accgccgtgt actactgcgc cggcggcctg 300
aggggcccct acagcgacag cgtgaccagc agcgtgcagt acaactactg gggccagggc 360
acccaggtga ccgtgagcag c 381

<210> SEQ ID NO 33
<211> LENGTH: 122
<212> TYPE: PRT
<213> ORGANISM: Artificial sequence
<220> FEATURE:
<223> OTHER INFORMATION: Synthetic

<400> SEQUENCE: 33

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Ser Asp Asp Tyr
            20                  25                  30

Ala Ile Gly Trp Phe Arg Gln Ala Pro Gly Lys Glu Arg Glu Gly Val
        35                  40                  45

Ser Cys Met Tyr Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr His Cys
                85                  90                  95

Ala Ala Gly Pro Trp Cys Phe Val Thr Gly Val Gly Arg Glu Glu Trp
            100                 105                 110

Gly Gln Gly Thr Gln Val Thr Val Ser Ser
        115                 120

<210> SEQ ID NO 34
<211> LENGTH: 366
<212> TYPE: DNA
<213> ORGANISM: Artificial sequence
<220> FEATURE:
<223> OTHER INFORMATION: Synthetic

<400> SEQUENCE: 34
caggtgcagc tggtggagag cggcggcggc ctggtgcagg ccggcggcag cctgaggctg 60
agctgcgccg ccagcggcat caccagcgac gactacgcca tcggctggtt caggcaggcc 120
cccggcaagg agagggaggg cgtgagctgc atgtacagca gcgacggcag cacctactac 180
gccgacagcg tgaagggcag gttcaccatc agcagggaca acgccaagaa caccgtgtac 240
ctgcagatga acagcctgag gcccgaggac accgccgtgt accactgcgc cgccggcccc 300
tggtgcttcg tgaccggcgt gggcagggag gagtggggcc agggcaccca ggtgaccgtg 360
agcagc 366

<210> SEQ ID NO 35
<211> LENGTH: 119
<212> TYPE: PRT
<213> ORGANISM: Artificial sequence
<220> FEATURE:
<223> OTHER INFORMATION: Synthetic

<400> SEQUENCE: 35

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Pro Ser
            20                  25                  30

Thr Met Ala Trp Phe Arg Gln Ala Pro Gly Lys Glu Arg Glu Leu Val
        35                  40                  45

Ala Arg Ile Gly Trp Thr Tyr Gly Asp Thr Tyr Tyr Val Asp Ser Ala
    50                  55                  60

Lys Gly Arg Phe Thr Ile Ser Met Asp Asn Val Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Leu Phe Arg Gly Gly Leu Ser Tyr Asn Phe Ser Asn Arg Gly
            100                 105                 110

Thr Gln Val Thr Val Ser Ser
        115

<210> SEQ ID NO 36
<211> LENGTH: 357
<212> TYPE: DNA
<213> ORGANISM: Artificial sequence
<220> FEATURE:
<223> OTHER INFORMATION: Synthetic

<400> SEQUENCE: 36
caggtgcagc tggtggagag cggcggcggc ctggtgcagg ccggcgacag cctgaggctg 60
agctgcgccg ccagcggcag gaccttcagc cccagcacca tggcctggtt caggcaggcc 120
cccggcaagg agagggagct ggtggccagg atcggctgga cctacggcga cacctactac 180
gtggacagcg ccaagggcag gttcaccatc agcatggaca acgtgaagaa caccgtgtac 240
ctgcagatga acagcctgaa gcccgaggac accgccgtgt actactgcgc cgccctgttc 300
aggggcggcc tgagctacaa cttcagcaac aggggcaccc aggtgaccgt gagcagc 357

<210> SEQ ID NO 37
<211> LENGTH: 129
<212> TYPE: PRT
<213> ORGANISM: Artificial sequence
<220> FEATURE:
<223> OTHER INFORMATION: Synthetic

<400> SEQUENCE: 37

Glu Val Gln Val Val Glu Ser Gly Gly Gly Leu Val Gln Ala Gly Asp
1 5 10 15

Ser Leu Arg Leu Ser Cys Thr Thr Ser Gly Arg Thr Phe Tyr Gly Asp
20 25 30

Tyr Ile Ala Trp Phe Arg Gln Ala Pro Gly Lys Glu Arg Glu Phe Val
35 40 45

Ala Ala Ile Ala Val Arg Gly Arg Gly Thr Phe Tyr Gly Asp Ser Val
50 55 60

Lys Gly Arg Phe Thr Ile Ser Arg Asp Asn Ala Glu Asn Thr Leu Ser
65 70 75 80

Leu Gln Met Asn Ser Leu Lys Pro Glu Asp Thr Ala Val Tyr Tyr Cys
85 90 95

Ala Ala Asp Ala Gly Ser Tyr Ala Ser Arg Gly Phe Pro Val Arg Glu
100 105 110

Thr Gly Arg Tyr Asp Tyr Trp Gly Gln Gly Thr Gln Val Thr Val Ser
115 120 125

Ser

<210> SEQ ID NO 38
<211> LENGTH: 387
<212> TYPE: DNA
<213> ORGANISM: Artificial sequence
<220> FEATURE:
<223> OTHER INFORMATION: Synthetic

<400> SEQUENCE: 38
gaggtgcagg tggtggagag cggcggcggc ctggtgcagg ccggcgacag cctgaggctg 60
agctgcacca ccagcggcag gaccttctac ggcgactaca tcgcctggtt caggcaggcc 120
cccggcaagg agagggagtt cgtggccgcc atcgccgtga ggggcagggg caccttctac 180
ggcgacagcg tgaagggcag gttcaccatc agcagggaca acgccgagaa caccctgagc 240
ctgcagatga acagcctgaa gcccgaggac accgccgtgt actactgcgc cgccgacgcc 300
ggcagctacg ccagcagggg cttccccgtg agggagaccg gcaggtacga ctactggggc 360
cagggcaccc aggtgaccgt gagcagc 387

<210> SEQ ID NO 39
<211> LENGTH: 127
<212> TYPE: PRT
<213> ORGANISM: Artificial sequence
<220> FEATURE:
<223> OTHER INFORMATION: Synthetic

<400> SEQUENCE: 39

Gln Val Gln Leu Val Glu Ser Gly Gly Gly Leu Val Gln Ala Gly Gly
1 5 10 15

Ser Leu Thr Val Ser Cys Thr Asn Ser Gly Arg Thr Leu Ser Thr Ser

```
            20                  25                  30

Thr Ile Ala Trp Phe Arg Gln Lys Pro Gly Lys Asp Ser Glu Phe Val
        35                  40                  45

Ala Ala Ile Arg Trp Ser Gly Gly Met Gly Trp Tyr Ala Asp Ser Val
    50                  55                  60

Lys Gly Arg Phe Thr Ile Ser Arg Asp Asn Ala Glu Asn Thr Val Ser
65                  70                  75                  80

Leu Gln Met Asn Thr Leu Gln Pro Glu Asp Thr Ala Val Tyr Phe Cys
                85                  90                  95

Ala Val Ser Thr Val Pro Tyr Tyr Gly Ser Ile Tyr Thr Arg Val Gly
            100                 105                 110

Asp Tyr Pro Tyr Trp Gly Gln Gly Thr Gln Val Thr Val Ser Ser
        115                 120                 125


<210> SEQ ID NO 40
<211> LENGTH: 381
<212> TYPE: DNA
<213> ORGANISM: Artificial sequence
<220> FEATURE:
<223> OTHER INFORMATION: Synthetic

<400> SEQUENCE: 40

caggtgcagc tggtggagag cggcggcggc ctggtgcagg ccggcggcag cctgaccgtg     60

agctgcacca acagcggcag gaccctgagc accagcacca tcgcctggtt caggcagaag    120

cccggcaagg acagcgagtt cgtggccgcc atcaggtgga gcggcggcat gggctggtac    180

gccgacagcg tgaagggcag gttcaccatc agcagggaca acgccgagaa caccgtgagc    240

ctgcagatga acaccctgca gcccgaggac accgccgtgt acttctgcgc cgtgagcacc    300

gtgccctact acggcagcat ctacaccagg gtgggcgact acccctactg gggccagggc    360

acccaggtga ccgtgagcag c                                              381


<210> SEQ ID NO 41
<211> LENGTH: 125
<212> TYPE: PRT
<213> ORGANISM: Artificial sequence
<220> FEATURE:
<223> OTHER INFORMATION: Synthetic

<400> SEQUENCE: 41

Gln Val Gln Leu Val Glu Ser Gly Gly Gly Leu Val Gln Ala Gly Gly
1               5                   10                  15

Ser Leu Arg Leu Ala Cys Ala Ala Ser Gly Asp Thr Val Ser Ile Tyr
            20                  25                  30

Tyr Met Gly Trp Phe Arg Gln Ala Pro Gly Lys Glu Arg Glu Phe Val
        35                  40                  45

Gly Ala Leu Ser Ala Ser Gly Gln Phe Thr Asp His Ala Asp Ser Val
    50                  55                  60

Lys Gly Arg Phe Thr Ile Ser Arg Asp Asp Ala Gln Asn Thr Val Phe
65                  70                  75                  80

Leu His Met Asn Asp Leu Lys Pro Glu Asp Thr Ala Val Tyr Tyr Cys
                85                  90                  95

Ala Val Gln Arg Tyr Gly Trp Val Tyr Arg Thr Asp Lys Thr Met Tyr
            100                 105                 110

Asn Tyr Trp Gly Gln Gly Thr Gln Val Thr Val Ser Ser
        115                 120                 125
```

<210> SEQ ID NO 42
<211> LENGTH: 375
<212> TYPE: DNA
<213> ORGANISM: Artificial sequence
<220> FEATURE:
<223> OTHER INFORMATION: Synthetic

<400> SEQUENCE: 42
caggtgcagc tggtggagag cggcggcggc ctggtgcagg ccggcggcag cctgaggctg 60
gcctgcgccg ccagcggcga caccgtgagc atctactaca tgggctggtt caggcaggcc 120
cccggcaagg agagggagtt cgtgggcgcc ctgagcgcca gcggccagtt caccgaccac 180
gccgacagcg tgaagggcag gttcaccatc agcagggacg acgcccagaa caccgtgttc 240
ctgcacatga acgacctgaa gcccgaggac accgccgtgt actactgcgc cgtgcagagg 300
tacggctggg tgtacaggac cgacaagacc atgtacaact actggggcca gggcacccag 360
gtgaccgtga gcagc 375

<210> SEQ ID NO 43
<211> LENGTH: 126
<212> TYPE: PRT
<213> ORGANISM: Artificial sequence
<220> FEATURE:
<223> OTHER INFORMATION: Synthetic

<400> SEQUENCE: 43

Gln Val Gln Leu Val Glu Ser Gly Gly Gly Leu Val Gln Ser Gly Gly
1 5 10 15

Ser Leu Arg Leu Ser Cys Ala Ala Ser Gly Phe Thr Phe Ser Asp Tyr
20 25 30

Thr Met Asn Trp Val Arg Gln Ala Pro Gly Lys Gly Leu Glu Trp Val
35 40 45

Ser Glu Ile Ser Ser Gly Gly His Phe Lys Ser Asn Ala Asp Ser Val
50 55 60

Lys Asp Arg Phe Thr Ile Ser Arg Asp Asn Ala Lys Asn Thr Leu Tyr
65 70 75 80

Leu Gln Met Asn Ser Leu Lys Pro Glu Asp Thr Ala Val Tyr Phe Cys
85 90 95

Ala Lys Cys Pro Arg Pro Ser Val Tyr Cys Arg Asp Tyr Glu Ser Thr
100 105 110

Ser Leu Tyr Arg Gly Gln Gly Thr Gln Val Thr Val Ser Ser
115 120 125

<210> SEQ ID NO 44
<211> LENGTH: 378
<212> TYPE: DNA
<213> ORGANISM: Artificial sequence
<220> FEATURE:
<223> OTHER INFORMATION: Synthetic

<400> SEQUENCE: 44
caggtgcagc tggtggagag cggcggcggc ctggtgcaga gcggcggcag cctgaggctg 60
agctgcgccg ccagcggctt caccttcagc gactacacca tgaactgggt gaggcaggcc 120
cccggcaagg gcctggagtg ggtgagcgag atcagcagcg gcggccactt caagagcaac 180
gccgacagcg tgaaggacag gttcaccatc agcagggaca acgccaagaa caccctgtac 240
ctgcagatga acagcctgaa gcccgaggac accgccgtgt acttctgcgc caagtgcccc 300
aggcccagcg tgtactgcag ggactacgag agcaccagcc tgtacagggg ccagggcacc 360
caggtgaccg tgagcagc 378

<210> SEQ ID NO 45
<211> LENGTH: 126
<212> TYPE: PRT
<213> ORGANISM: Artificial sequence
<220> FEATURE:
<223> OTHER INFORMATION: Synthetic

<400> SEQUENCE: 45

Gln Val Gln Leu Val Glu Ser Gly Gly Gly Leu Val Gln Pro Gly Gly
1 5 10 15

Ser Leu Thr Leu Ser Cys Ala Ala Ser Gly Phe Asp Phe Ser Phe Tyr
20 25 30

Thr Met Thr Trp Val Arg Gln Ala Gln Gly Lys Gly Leu Glu Trp Val
35 40 45

Ser Thr Ile Ser Thr Gly Gly Gly Gly Ser Asn Tyr Ala Asp Ser Val
50 55 60

Lys Gly Arg Phe Thr Ile Ser Arg Asp Asn Ala Lys Lys Thr Leu Tyr
65 70 75 80

Leu Gln Met Thr Ser Leu Lys Pro Glu Asp Thr Ala Val Tyr Tyr Cys
85 90 95

Ala Ser His Arg Arg Gly Tyr Met Phe Val Ser Ser Arg Lys Asn Glu
100 105 110

Tyr Asp Tyr Trp Gly Arg Gly Thr Gln Val Thr Val Ser Ser
115 120 125

<210> SEQ ID NO 46
<211> LENGTH: 378
<212> TYPE: DNA
<213> ORGANISM: Artificial sequence
<220> FEATURE:
<223> OTHER INFORMATION: Synthetic

<400> SEQUENCE: 46
caggtgcagc tggtggagag cggcggcggc ctggtgcagc ccggcggcag cctgaccctg 60
agctgcgccg ccagcggctt cgacttcagc ttctacacca tgacctgggt gaggcaggcc 120
cagggcaagg gcctggagtg ggtgagcacc atcagcaccg gcggcggcgg cagcaactac 180
gccgacagcg tgaagggcag gttcaccatc agcagggaca acgccaagaa gaccctgtac 240
ctgcagatga ccagcctgaa gcccgaggac accgccgtgt actactgcgc cagccacagg 300
aggggctaca tgttcgtgag cagcaggaag aacgagtacg actactgggg caggggcacc 360
caggtgaccg tgagcagc 378

<210> SEQ ID NO 47
<211> LENGTH: 122
<212> TYPE: PRT
<213> ORGANISM: Artificial sequence
<220> FEATURE:
<223> OTHER INFORMATION: Synthetic

<400> SEQUENCE: 47

Gln Val Gln Leu Val Glu Ser Gly Gly Gly Leu Val Gln Ala Gly Gly
1 5 10 15

Ser Leu Arg Leu Ser Cys Ala Ala Ser Gly Arg Ala Ser Gly Ser Gly
20 25 30

Ala Met Gly Trp Phe Arg Gln Ala Pro Gly Gln Glu Arg Arg Phe Val
35 40 45

```
Ala Gly Ile Glu Trp Ser Ser Gly Gly Pro Val Tyr Ala Asp Ser Val
    50                  55                  60

Lys Gly Arg Phe Thr Leu Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Ala Pro Trp Val Phe Ser Ser Pro Asp Asp Tyr Met Tyr Trp
            100                 105                 110

Gly Gln Gly Thr Gln Val Thr Val Ser Ser
        115                 120


<210> SEQ ID NO 48
<211> LENGTH: 366
<212> TYPE: DNA
<213> ORGANISM: Artificial sequence
<220> FEATURE:
<223> OTHER INFORMATION: Synthetic

<400> SEQUENCE: 48

caggtgcagc tggtggagag cggcggcggc ctggtgcagg ccggcggcag cctgaggctg      60

agctgcgccg ccagcggcag ggccagcggc agcggcgcca tgggctggtt caggcaggcc     120

cccggccagg agaggaggtt cgtggccggc atcgagtgga gcagcggcgg ccccgtgtac     180

gccgacagcg tgaagggcag gttcaccctg agcagggaca acgccaagaa caccgtgcac     240

ctgcagatga acagcctgaa gcccgaggac accgccgtgt actactgcgc cgccgccccc     300

tgggtgttca gcagccccga cgactacatg tactggggcc agggcaccca ggtgaccgtg     360

agcagc                                                                366


<210> SEQ ID NO 49
<211> LENGTH: 126
<212> TYPE: PRT
<213> ORGANISM: Artificial sequence
<220> FEATURE:
<223> OTHER INFORMATION: Synthetic

<400> SEQUENCE: 49

Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Tyr Tyr
            20                  25                  30

Gly Met Gly Trp Phe Arg Gln Ala Pro Gly Lys Glu Arg Glu Phe Val
        35                  40                  45

Ala Ala Ile Asn Trp Ser Gly Thr Ser Thr Tyr Tyr Ala Asp Ser Val
    50                  55                  60

Lys Asp Arg Phe Thr Val Ser Arg Asp Asn Ala Lys Asn Thr Ala Tyr
65                  70                  75                  80

Leu His Met Asn Asn Leu Lys Pro Glu Asp Thr Ala Val Tyr Tyr Cys
                85                  90                  95

Ala Ala Arg Lys Tyr Ser Ser Ser Gln Ala Met Gly Leu Pro Asn Asp
            100                 105                 110

Ile Asp Tyr Trp Gly Gln Gly Thr Gln Val Thr Val Ser Ser
        115                 120                 125


<210> SEQ ID NO 50
<211> LENGTH: 378
<212> TYPE: DNA
<213> ORGANISM: Artificial sequence
<220> FEATURE:
```

<223> OTHER INFORMATION: Synthetic

<400> SEQUENCE: 50
caggtgcagc tggtggagag cggcggcggc ctggtgcagg ccggcggcag cctgaggctg 60
agctgcgccg ccagcggcct gaccttcagc tactacggca tgggctggtt caggcaggcc 120
cccggcaagg agagggagtt cgtggccgcc atcaactgga gcggcaccag cacctactac 180
gccgacagcg tgaaggacag gttcaccgtg agcagggaca acgccaagaa caccgcctac 240
ctgcacatga acaacctgaa gcccgaggac accgccgtgt actactgcgc cgccaggaag 300
tacagcagca gccaggccat gggcctgccc aacgacatcg actactgggg ccagggcacc 360
caggtgaccg tgagcagc 378

<210> SEQ ID NO 51
<211> LENGTH: 124
<212> TYPE: PRT
<213> ORGANISM: Artificial sequence
<220> FEATURE:
<223> OTHER INFORMATION: Synthetic

<400> SEQUENCE: 51

Gln Val Gln Leu Val Glu Ser Gly Gly Gly Leu Val Gln Ala Gly Asp
1 5 10 15

Ser Leu Arg Leu Ser Cys Ala Ala Ser Thr Arg Ile Phe Arg Ser Tyr
20 25 30

Val Met Gly Trp Phe Arg Gln Ala Pro Gly Lys Glu Arg Glu Ala Val
35 40 45

Ala Ser Ile Arg Trp Ser Asn Asp Thr Gly Thr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Ser Cys
85 90 95

Ala Ala Asp Ser Pro Pro Trp Gly Arg Thr Trp Tyr Thr Gly Tyr Asp
100 105 110

Tyr Trp Gly Gln Gly Thr Gln Val Thr Val Ser Ser
115 120

<210> SEQ ID NO 52
<211> LENGTH: 372
<212> TYPE: DNA
<213> ORGANISM: Artificial sequence
<220> FEATURE:
<223> OTHER INFORMATION: Synthetic

<400> SEQUENCE: 52
caggtgcagc tggtggagag cggcggcggc ctggtgcagg ccggcgacag cctgaggctg 60
agctgcgccg ccagcaccag gatcttcagg agctacgtga tgggctggtt caggcaggcc 120
cccggcaagg agagggaggc cgtggccagc atcaggtgga gcaacgacac cggcacctac 180
gccgacagcg tgaagggcag gttcaccatc agcagggaca acgccaagaa caccgtgtac 240
ctgcagatga acagcctgaa gcccgaggac accgccgtgt acagctgcgc cgccgacagc 300 ccccccctggg gcaggacctg gtacaccggc tacgactact ggggccaggg cacccaggtg 360
accgtgagca gc 372

<210> SEQ ID NO 53
<211> LENGTH: 125

<212> TYPE: PRT
<213> ORGANISM: Artificial sequence
<220> FEATURE:
<223> OTHER INFORMATION: Synthetic

<400> SEQUENCE: 53

Glu Val Gln Val Val Glu Ser Gly Gly Gly Leu Val Gln Thr Gly Gly
1 5 10 15

Ser Leu Arg Leu Ser Cys Ala Ala Ser Gly Arg Pro Phe Asp Trp Leu
20 25 30

Thr Val Gly Trp Phe Arg Gln Ala Pro Gly Lys Glu Arg Glu Phe Val
35 40 45

Ala Ala Ile Ser Gln Ser Gly Gly Arg Ile Phe Tyr Ser Asp Ser Val
50 55 60

Lys Gly Arg Phe Thr Ile Ser Arg Asp Asn Ala Lys Asn Thr Ala Phe
65 70 75 80

Leu Gln Met Asn Ser Leu Lys Pro Glu Asp Thr Ala Val Tyr Ser Cys
85 90 95

Ala Ala Gln Met Arg Gly Tyr Ser Arg Ala Ala Tyr Pro Asp Glu Tyr
100 105 110

Asp Tyr Trp Gly Gln Gly Thr Gln Val Thr Val Ser Ser
115 120 125

<210> SEQ ID NO 54
<211> LENGTH: 375
<212> TYPE: DNA
<213> ORGANISM: Artificial sequence
<220> FEATURE:
<223> OTHER INFORMATION: Synthetic

<400> SEQUENCE: 54
gaggtgcagg tggtggagag cggcggcggc ctggtgcaga ccggcggcag cctgaggctg 60
agctgcgccg ccagcggcag gcccttcgac tggctgaccg tgggctggtt caggcaggcc 120
cccggcaagg agagggagtt cgtggccgcc atcagccaga gcggcggcag gatcttctac 180
agcgacagcg tgaagggcag gttcaccatc agcagggaca acgccaagaa caccgccttc 240
ctgcagatga acagcctgaa gcccgaggac accgccgtgt acagctgcgc cgcccagatg 300
aggggctaca gcagggccgc ctaccccgac gagtacgact actggggcca gggcacccag 360
gtgaccgtga gcagc 375

<210> SEQ ID NO 55
<211> LENGTH: 119
<212> TYPE: PRT
<213> ORGANISM: Artificial sequence
<220> FEATURE:
<223> OTHER INFORMATION: Synthetic

<400> SEQUENCE: 55

Gln Val Gln Leu Val Glu Ser Gly Gly Gly Leu Val Gln Ala Gly Asp
1 5 10 15

Ser Leu Arg Leu Ala Cys Glu Ala Ser Gly Arg Thr Ala Thr Ile Ser
20 25 30

Thr Met Gly Trp Phe Arg Gln Ala Pro Gly Lys Glu Arg Glu Phe Val
35 40 45

Gly Arg Ile Asp Trp Ser Ala Glu Ser Thr Tyr Ile Val Asp Ser Val
50 55 60

Lys Gly Arg Phe Ile Ile Ser Arg Asp Asn Ala Lys Asn Ala Gly Tyr
65 70 75 80

Leu Gln Met Asn Ser Leu Lys Pro Val Asp Thr Ala Val Tyr Tyr Cys
85 90 95

Ala Ala Ile Val Val Arg Glu Arg Ser Tyr Lys Tyr Trp Gly Gln Gly
100 105 110

Thr Gln Val Thr Val Ser Ser
115

<210> SEQ ID NO 56
<211> LENGTH: 357
<212> TYPE: DNA
<213> ORGANISM: Artificial sequence
<220> FEATURE:
<223> OTHER INFORMATION: Synthetic

<400> SEQUENCE: 56
caggtgcagc tggtggagag cggcggcggc ctggtgcagg ccggcgacag cctgaggctg 60
gcctgcgagg ccagcggcag gaccgccacc atcagcacca tgggctggtt caggcaggcc 120
cccggcaagg agagggagtt cgtgggcagg atcgactgga gcgccgagag cacctacatc 180
gtggacagcg tgaagggcag gttcatcatc agcagggaca acgccaagaa cgccggctac 240
ctgcagatga acagcctgaa gcccgtggac accgccgtgt actactgcgc cgccatcgtg 300
gtgagggaga ggagctacaa gtactggggc cagggcaccc aggtgaccgt gagcagc 357

<210> SEQ ID NO 57
<211> LENGTH: 8
<212> TYPE: PRT
<213> ORGANISM: Artificial sequence
<220> FEATURE:
<223> OTHER INFORMATION: CDR

<400> SEQUENCE: 57

Gly Ile Thr Phe Ser Ser Tyr Tyr
1 5

<210> SEQ ID NO 58
<211> LENGTH: 8
<212> TYPE: PRT
<213> ORGANISM: Artificial sequence
<220> FEATURE:
<223> OTHER INFORMATION: CDR

<400> SEQUENCE: 58

Val Gly Arg Ser Gly Ala Pro Ser
1 5

<210> SEQ ID NO 59
<211> LENGTH: 14
<212> TYPE: PRT
<213> ORGANISM: Artificial sequence
<220> FEATURE:
<223> OTHER INFORMATION: CDR

<400> SEQUENCE: 59

Ala Ala Lys Trp Met Ala Ala Ser Thr Thr Val Ala Asp Tyr
1 5 10

<210> SEQ ID NO 60
<211> LENGTH: 5
<212> TYPE: PRT
<213> ORGANISM: Artificial sequence
<220> FEATURE:
<223> OTHER INFORMATION: CDR

<400> SEQUENCE: 60

Ser Tyr Tyr Met Ser
1 5

<210> SEQ ID NO 61
<211> LENGTH: 17
<212> TYPE: PRT
<213> ORGANISM: Artificial sequence
<220> FEATURE:
<223> OTHER INFORMATION: CDR

<400> SEQUENCE: 61

Gly Val Gly Arg Ser Gly Ala Pro Ser His His Ala Asp Ser Val Lys
1 5 10 15

Gly

<210> SEQ ID NO 62
<211> LENGTH: 12
<212> TYPE: PRT
<213> ORGANISM: Artificial sequence
<220> FEATURE:
<223> OTHER INFORMATION: CDR

<400> SEQUENCE: 62

Lys Trp Met Ala Ala Ser Thr Thr Val Ala Asp Tyr
1 5 10

<210> SEQ ID NO 63
<211> LENGTH: 7
<212> TYPE: PRT
<213> ORGANISM: Artificial sequence
<220> FEATURE:
<223> OTHER INFORMATION: CDR

<400> SEQUENCE: 63

Gly Ile Thr Phe Ser Ser Tyr
1 5

<210> SEQ ID NO 64
<211> LENGTH: 6
<212> TYPE: PRT
<213> ORGANISM: Artificial sequence
<220> FEATURE:
<223> OTHER INFORMATION: CDR

<400> SEQUENCE: 64

Gly Arg Ser Gly Ala Pro
1 5

<210> SEQ ID NO 65
<211> LENGTH: 12
<212> TYPE: PRT
<213> ORGANISM: Artificial sequence
<220> FEATURE:
<223> OTHER INFORMATION: CDR

<400> SEQUENCE: 65

Lys Trp Met Ala Ala Ser Thr Thr Val Ala Asp Tyr
1 5 10

<210> SEQ ID NO 66
<211> LENGTH: 8
<212> TYPE: PRT
<213> ORGANISM: Artificial sequence
<220> FEATURE:
<223> OTHER INFORMATION: CDR

<400> SEQUENCE: 66

Gly Asp Arg Val Ser Ile Ala Leu
1 5

<210> SEQ ID NO 67
<211> LENGTH: 8
<212> TYPE: PRT
<213> ORGANISM: Artificial sequence
<220> FEATURE:
<223> OTHER INFORMATION: CDR

<400> SEQUENCE: 67

Ile Ser Pro Ser Gly Gly Arg Ile
1 5

<210> SEQ ID NO 68
<211> LENGTH: 18
<212> TYPE: PRT
<213> ORGANISM: Artificial sequence
<220> FEATURE:
<223> OTHER INFORMATION: CDR

<400> SEQUENCE: 68

Ala Ala Asn Phe Arg Gly Tyr Leu Ser Ser Ser Arg Gly Ser Asp Tyr
1 5 10 15

Ala Tyr

<210> SEQ ID NO 69
<211> LENGTH: 5
<212> TYPE: PRT
<213> ORGANISM: Artificial sequence
<220> FEATURE:
<223> OTHER INFORMATION: CDR

<400> SEQUENCE: 69

Ile Ala Leu Met Gly
1 5

<210> SEQ ID NO 70
<211> LENGTH: 17
<212> TYPE: PRT
<213> ORGANISM: Artificial sequence
<220> FEATURE:
<223> OTHER INFORMATION: CDR

<400> SEQUENCE: 70

Ala Ile Ser Pro Ser Gly Gly Arg Ile Thr Tyr Ser Asp Ser Val Lys
1 5 10 15

Gly

<210> SEQ ID NO 71
<211> LENGTH: 16
<212> TYPE: PRT
<213> ORGANISM: Artificial sequence
<220> FEATURE:
<223> OTHER INFORMATION: CDR

<400> SEQUENCE: 71

Asn Phe Arg Gly Tyr Leu Ser Ser Ser Arg Gly Ser Asp Tyr Ala Tyr
1 5 10 15

<210> SEQ ID NO 72
<211> LENGTH: 7
<212> TYPE: PRT

<213> ORGANISM: Artificial sequence
<220> FEATURE:
<223> OTHER INFORMATION: CDR

<400> SEQUENCE: 72

Gly Asp Arg Val Ser Ile Ala
1               5

<210> SEQ ID NO 73
<211> LENGTH: 6
<212> TYPE: PRT
<213> ORGANISM: Artificial sequence
<220> FEATURE:
<223> OTHER INFORMATION: CDR

<400> SEQUENCE: 73

Ser Pro Ser Gly Gly Arg
1               5

<210> SEQ ID NO 74
<211> LENGTH: 16
<212> TYPE: PRT
<213> ORGANISM: Artificial sequence
<220> FEATURE:
<223> OTHER INFORMATION: CDR

<400> SEQUENCE: 74

Asn Phe Arg Gly Tyr Leu Ser Ser Ser Arg Gly Ser Asp Tyr Ala Tyr
1               5                   10                  15

<210> SEQ ID NO 75
<211> LENGTH: 8
<212> TYPE: PRT
<213> ORGANISM: Artificial sequence
<220> FEATURE:
<223> OTHER INFORMATION: CDR

<400> SEQUENCE: 75

Gly Leu Thr Phe Ser Phe Tyr Asn
1               5

<210> SEQ ID NO 76
<211> LENGTH: 8
<212> TYPE: PRT
<213> ORGANISM: Artificial sequence
<220> FEATURE:
<223> OTHER INFORMATION: CDR

<400> SEQUENCE: 76

Ile Ser Gln Ser Gly Leu Ser Thr
1               5

<210> SEQ ID NO 77
<211> LENGTH: 17
<212> TYPE: PRT
<213> ORGANISM: Artificial sequence
<220> FEATURE:
<223> OTHER INFORMATION: CDR

<400> SEQUENCE: 77

Ala Ala Gly Arg Arg Gly Tyr Leu Ala Ser Thr Thr Asn Asp Tyr Glu
1               5                   10                  15

Tyr

<210> SEQ ID NO 78
<211> LENGTH: 5

<212> TYPE: PRT
<213> ORGANISM: Artificial sequence
<220> FEATURE:
<223> OTHER INFORMATION: CDR

<400> SEQUENCE: 78

Phe Tyr Asn Met Gly
1 5

<210> SEQ ID NO 79
<211> LENGTH: 17
<212> TYPE: PRT
<213> ORGANISM: Artificial sequence
<220> FEATURE:
<223> OTHER INFORMATION: CDR

<400> SEQUENCE: 79

Ala Ile Ser Gln Ser Gly Leu Ser Thr His Tyr Ala Asp Ser Met Lys
1 5 10 15

Gly

<210> SEQ ID NO 80
<211> LENGTH: 15
<212> TYPE: PRT
<213> ORGANISM: Artificial sequence
<220> FEATURE:
<223> OTHER INFORMATION: CDR

<400> SEQUENCE: 80

Gly Arg Arg Gly Tyr Leu Ala Ser Thr Thr Asn Asp Tyr Glu Tyr
1 5 10 15

<210> SEQ ID NO 81
<211> LENGTH: 7
<212> TYPE: PRT
<213> ORGANISM: Artificial sequence
<220> FEATURE:
<223> OTHER INFORMATION: CDR

<400> SEQUENCE: 81

Gly Leu Thr Phe Ser Phe Tyr
1 5

<210> SEQ ID NO 82
<211> LENGTH: 6
<212> TYPE: PRT
<213> ORGANISM: Artificial sequence
<220> FEATURE:
<223> OTHER INFORMATION: CDR

<400> SEQUENCE: 82

Ser Gln Ser Gly Leu Ser
1 5

<210> SEQ ID NO 83
<211> LENGTH: 15
<212> TYPE: PRT
<213> ORGANISM: Artificial sequence
<220> FEATURE:
<223> OTHER INFORMATION: CDR

<400> SEQUENCE: 83

Gly Arg Arg Gly Tyr Leu Ala Ser Thr Thr Asn Asp Tyr Glu Tyr
1 5 10 15

<210> SEQ ID NO 84

<211> LENGTH: 8
<212> TYPE: PRT
<213> ORGANISM: Artificial sequence
<220> FEATURE:
<223> OTHER INFORMATION: CDR

<400> SEQUENCE: 84

Gly Arg Ala Tyr Ser Arg Ser Asp
1               5

<210> SEQ ID NO 85
<211> LENGTH: 7
<212> TYPE: PRT
<213> ORGANISM: Artificial sequence
<220> FEATURE:
<223> OTHER INFORMATION: CDR

<400> SEQUENCE: 85

Ile Thr Phe Gly Gly Gly Thr
1               5

<210> SEQ ID NO 86
<211> LENGTH: 22
<212> TYPE: PRT
<213> ORGANISM: Artificial sequence
<220> FEATURE:
<223> OTHER INFORMATION: CDR

<400> SEQUENCE: 86

Ala Ala Gly Phe Arg Gly Ser Arg Trp Ser Thr Ala Ala Arg Arg Lys
1               5                   10                  15

Glu Asp Asp Tyr Ala Phe
            20

<210> SEQ ID NO 87
<211> LENGTH: 5
<212> TYPE: PRT
<213> ORGANISM: Artificial sequence
<220> FEATURE:
<223> OTHER INFORMATION: CDR

<400> SEQUENCE: 87

Arg Ser Asp Met Gly
1               5

<210> SEQ ID NO 88
<211> LENGTH: 16
<212> TYPE: PRT
<213> ORGANISM: Artificial sequence
<220> FEATURE:
<223> OTHER INFORMATION: CDR

<400> SEQUENCE: 88

Val Ile Thr Phe Gly Gly Gly Thr Asp Tyr Ala Asp Ser Val Lys Gly
1               5                   10                  15

<210> SEQ ID NO 89
<211> LENGTH: 20
<212> TYPE: PRT
<213> ORGANISM: Artificial sequence
<220> FEATURE:
<223> OTHER INFORMATION: CDR

<400> SEQUENCE: 89

Gly Phe Arg Gly Ser Arg Trp Ser Thr Ala Ala Arg Arg Lys Glu Asp
1               5                   10                  15

Asp Tyr Ala Phe
20

<210> SEQ ID NO 90
<211> LENGTH: 7
<212> TYPE: PRT
<213> ORGANISM: Artificial sequence
<220> FEATURE:
<223> OTHER INFORMATION: CDR

<400> SEQUENCE: 90

Gly Arg Ala Tyr Ser Arg Ser
1 5

<210> SEQ ID NO 91
<211> LENGTH: 5
<212> TYPE: PRT
<213> ORGANISM: Artificial sequence
<220> FEATURE:
<223> OTHER INFORMATION: CDR

<400> SEQUENCE: 91

Thr Phe Gly Gly Gly
1 5

<210> SEQ ID NO 92
<211> LENGTH: 20
<212> TYPE: PRT
<213> ORGANISM: Artificial sequence
<220> FEATURE:
<223> OTHER INFORMATION: CDR

<400> SEQUENCE: 92

Gly Phe Arg Gly Ser Arg Trp Ser Thr Ala Ala Arg Arg Lys Glu Asp
1 5 10 15

Asp Tyr Ala Phe
20

<210> SEQ ID NO 93
<211> LENGTH: 7
<212> TYPE: PRT
<213> ORGANISM: Artificial sequence
<220> FEATURE:
<223> OTHER INFORMATION: CDR

<400> SEQUENCE: 93

Gly Ser Trp Phe Asn Ile Ala
1 5

<210> SEQ ID NO 94
<211> LENGTH: 8
<212> TYPE: PRT
<213> ORGANISM: Artificial sequence
<220> FEATURE:
<223> OTHER INFORMATION: CDR

<400> SEQUENCE: 94

Ile Arg Trp Ser Asp Ser Lys Thr
1 5

<210> SEQ ID NO 95
<211> LENGTH: 18
<212> TYPE: PRT
<213> ORGANISM: Artificial sequence
<220> FEATURE:
<223> OTHER INFORMATION: CDR

<400> SEQUENCE: 95

Ala Ala Gln Arg Tyr Tyr Arg Gly Ser Tyr Asn Arg Gln Thr Asn Tyr
1 5 10 15

Asp His

<210> SEQ ID NO 96
<211> LENGTH: 4
<212> TYPE: PRT
<213> ORGANISM: Artificial sequence
<220> FEATURE:
<223> OTHER INFORMATION: CDR

<400> SEQUENCE: 96

Ile Ala Met Gly
1

<210> SEQ ID NO 97
<211> LENGTH: 17
<212> TYPE: PRT
<213> ORGANISM: Artificial sequence
<220> FEATURE:
<223> OTHER INFORMATION: CDR

<400> SEQUENCE: 97

Gly Ile Arg Trp Ser Asp Ser Lys Thr Tyr Tyr Ala Asp Ser Val Lys
1 5 10 15

Gly

<210> SEQ ID NO 98
<211> LENGTH: 16
<212> TYPE: PRT
<213> ORGANISM: Artificial sequence
<220> FEATURE:
<223> OTHER INFORMATION: CDR

<400> SEQUENCE: 98

Gln Arg Tyr Tyr Arg Gly Ser Tyr Asn Arg Gln Thr Asn Tyr Asp His
1 5 10 15

<210> SEQ ID NO 99
<211> LENGTH: 6
<212> TYPE: PRT
<213> ORGANISM: Artificial sequence
<220> FEATURE:
<223> OTHER INFORMATION: CDR

<400> SEQUENCE: 99

Gly Ser Trp Phe Asn Ile
1 5

<210> SEQ ID NO 100
<211> LENGTH: 6
<212> TYPE: PRT
<213> ORGANISM: Artificial sequence
<220> FEATURE:
<223> OTHER INFORMATION: CDR

<400> SEQUENCE: 100

Arg Trp Ser Asp Ser Lys
1 5

<210> SEQ ID NO 101
<211> LENGTH: 16
<212> TYPE: PRT
<213> ORGANISM: Artificial sequence

<220> FEATURE:
<223> OTHER INFORMATION: CDR

<400> SEQUENCE: 101

Gln Arg Tyr Tyr Arg Gly Ser Tyr Asn Arg Gln Thr Asn Tyr Asp His
1               5                   10                  15

<210> SEQ ID NO 102
<211> LENGTH: 8
<212> TYPE: PRT
<213> ORGANISM: Artificial sequence
<220> FEATURE:
<223> OTHER INFORMATION: CDR

<400> SEQUENCE: 102

Gly Gly Thr Leu Ser Arg Ile Thr
1               5

<210> SEQ ID NO 103
<211> LENGTH: 8
<212> TYPE: PRT
<213> ORGANISM: Artificial sequence
<220> FEATURE:
<223> OTHER INFORMATION: CDR

<400> SEQUENCE: 103

Ile Lys Trp Gly Gly Ser Ser Thr
1               5

<210> SEQ ID NO 104
<211> LENGTH: 20
<212> TYPE: PRT
<213> ORGANISM: Artificial sequence
<220> FEATURE:
<223> OTHER INFORMATION: CDR

<400> SEQUENCE: 104

Ala Gly Gly Leu Arg Gly Pro Tyr Ser Asp Ser Val Thr Ser Ser Val
1               5                   10                  15

Gln Tyr Asn Tyr
            20

<210> SEQ ID NO 105
<211> LENGTH: 5
<212> TYPE: PRT
<213> ORGANISM: Artificial sequence
<220> FEATURE:
<223> OTHER INFORMATION: CDR

<400> SEQUENCE: 105

Arg Ile Thr Met Gly
1               5

<210> SEQ ID NO 106
<211> LENGTH: 17
<212> TYPE: PRT
<213> ORGANISM: Artificial sequence
<220> FEATURE:
<223> OTHER INFORMATION: CDR

<400> SEQUENCE: 106

Ala Ile Lys Trp Gly Gly Ser Ser Thr Pro Tyr Ser Asp Ser Val Lys
1               5                   10                  15

Gly

<210> SEQ ID NO 107
<211> LENGTH: 18
<212> TYPE: PRT
<213> ORGANISM: Artificial sequence
<220> FEATURE:
<223> OTHER INFORMATION: CDR

<400> SEQUENCE: 107

Gly Leu Arg Gly Pro Tyr Ser Asp Ser Val Thr Ser Ser Val Gln Tyr
1 5 10 15

Asn Tyr

<210> SEQ ID NO 108
<211> LENGTH: 7
<212> TYPE: PRT
<213> ORGANISM: Artificial sequence
<220> FEATURE:
<223> OTHER INFORMATION: CDR

<400> SEQUENCE: 108

Gly Gly Thr Leu Ser Arg Ile
1 5

<210> SEQ ID NO 109
<211> LENGTH: 6
<212> TYPE: PRT
<213> ORGANISM: Artificial sequence
<220> FEATURE:
<223> OTHER INFORMATION: CDR

<400> SEQUENCE: 109

Lys Trp Gly Gly Ser Ser
1 5

<210> SEQ ID NO 110
<211> LENGTH: 18
<212> TYPE: PRT
<213> ORGANISM: Artificial sequence
<220> FEATURE:
<223> OTHER INFORMATION: CDR

<400> SEQUENCE: 110

Gly Leu Arg Gly Pro Tyr Ser Asp Ser Val Thr Ser Ser Val Gln Tyr
1 5 10 15

Asn Tyr

<210> SEQ ID NO 111
<211> LENGTH: 8
<212> TYPE: PRT
<213> ORGANISM: Artificial sequence
<220> FEATURE:
<223> OTHER INFORMATION: CDR

<400> SEQUENCE: 111

Gly Ile Thr Ser Asp Asp Tyr Ala
1 5

<210> SEQ ID NO 112
<211> LENGTH: 8
<212> TYPE: PRT
<213> ORGANISM: Artificial sequence
<220> FEATURE:
<223> OTHER INFORMATION: CDR

<400> SEQUENCE: 112

Met Tyr Ser Ser Asp Gly Ser Thr 1 5

<210> SEQ ID NO 113
<211> LENGTH: 15
<212> TYPE: PRT
<213> ORGANISM: Artificial sequence
<220> FEATURE:
<223> OTHER INFORMATION: CDR

<400> SEQUENCE: 113

Ala Ala Gly Pro Trp Cys Phe Val Thr Gly Val Gly Arg Glu Glu
1 5 10 15

<210> SEQ ID NO 114
<211> LENGTH: 5
<212> TYPE: PRT
<213> ORGANISM: Artificial sequence
<220> FEATURE:
<223> OTHER INFORMATION: CDR

<400> SEQUENCE: 114

Asp Tyr Ala Ile Gly
1 5

<210> SEQ ID NO 115
<211> LENGTH: 17
<212> TYPE: PRT
<213> ORGANISM: Artificial sequence
<220> FEATURE:
<223> OTHER INFORMATION: CDR

<400> SEQUENCE: 115

Cys Met Tyr Ser Ser Asp Gly Ser Thr Tyr Tyr Ala Asp Ser Val Lys
1 5 10 15

Gly

<210> SEQ ID NO 116
<211> LENGTH: 13
<212> TYPE: PRT
<213> ORGANISM: Artificial sequence
<220> FEATURE:
<223> OTHER INFORMATION: CDR

<400> SEQUENCE: 116

Gly Pro Trp Cys Phe Val Thr Gly Val Gly Arg Glu Glu
1 5 10

<210> SEQ ID NO 117
<211> LENGTH: 7
<212> TYPE: PRT
<213> ORGANISM: Artificial sequence
<220> FEATURE:
<223> OTHER INFORMATION: CDR

<400> SEQUENCE: 117

Gly Ile Thr Ser Asp Asp Tyr
1 5

<210> SEQ ID NO 118
<211> LENGTH: 6
<212> TYPE: PRT
<213> ORGANISM: Artificial sequence
<220> FEATURE:
<223> OTHER INFORMATION: CDR

<400> SEQUENCE: 118

Tyr Ser Ser Asp Gly Ser
1 5

<210> SEQ ID NO 119
<211> LENGTH: 13
<212> TYPE: PRT
<213> ORGANISM: Artificial sequence
<220> FEATURE:
<223> OTHER INFORMATION: CDR

<400> SEQUENCE: 119

Gly Pro Trp Cys Phe Val Thr Gly Val Gly Arg Glu Glu
1 5 10

<210> SEQ ID NO 120
<211> LENGTH: 8
<212> TYPE: PRT
<213> ORGANISM: Artificial sequence
<220> FEATURE:
<223> OTHER INFORMATION: CDR

<400> SEQUENCE: 120

Gly Arg Thr Phe Ser Pro Ser Thr
1 5

<210> SEQ ID NO 121
<211> LENGTH: 8
<212> TYPE: PRT
<213> ORGANISM: Artificial sequence
<220> FEATURE:
<223> OTHER INFORMATION: CDR

<400> SEQUENCE: 121

Ile Gly Trp Thr Tyr Gly Asp Thr
1 5

<210> SEQ ID NO 122
<211> LENGTH: 12
<212> TYPE: PRT
<213> ORGANISM: Artificial sequence
<220> FEATURE:
<223> OTHER INFORMATION: CDR

<400> SEQUENCE: 122

Ala Ala Leu Phe Arg Gly Gly Leu Ser Tyr Asn Phe
1 5 10

<210> SEQ ID NO 123
<211> LENGTH: 5
<212> TYPE: PRT
<213> ORGANISM: Artificial sequence
<220> FEATURE:
<223> OTHER INFORMATION: CDR

<400> SEQUENCE: 123

Pro Ser Thr Met Ala
1 5

<210> SEQ ID NO 124
<211> LENGTH: 17
<212> TYPE: PRT
<213> ORGANISM: Artificial sequence
<220> FEATURE:
<223> OTHER INFORMATION: CDR

<400> SEQUENCE: 124

Arg Ile Gly Trp Thr Tyr Gly Asp Thr Tyr Tyr Val Asp Ser Ala Lys 1 5 10 15

Gly

<210> SEQ ID NO 125
<211> LENGTH: 10
<212> TYPE: PRT
<213> ORGANISM: Artificial sequence
<220> FEATURE:
<223> OTHER INFORMATION: CDR

<400> SEQUENCE: 125

Leu Phe Arg Gly Gly Leu Ser Tyr Asn Phe
1 5 10

<210> SEQ ID NO 126
<211> LENGTH: 7
<212> TYPE: PRT
<213> ORGANISM: Artificial sequence
<220> FEATURE:
<223> OTHER INFORMATION: CDR

<400> SEQUENCE: 126

Gly Arg Thr Phe Ser Pro Ser
1 5

<210> SEQ ID NO 127
<211> LENGTH: 6
<212> TYPE: PRT
<213> ORGANISM: Artificial sequence
<220> FEATURE:
<223> OTHER INFORMATION: CDR

<400> SEQUENCE: 127

Gly Trp Thr Tyr Gly Asp
1 5

<210> SEQ ID NO 128
<211> LENGTH: 10
<212> TYPE: PRT
<213> ORGANISM: Artificial sequence
<220> FEATURE:
<223> OTHER INFORMATION: CDR

<400> SEQUENCE: 128

Leu Phe Arg Gly Gly Leu Ser Tyr Asn Phe
1 5 10

<210> SEQ ID NO 129
<211> LENGTH: 8
<212> TYPE: PRT
<213> ORGANISM: Artificial sequence
<220> FEATURE:
<223> OTHER INFORMATION: CDR

<400> SEQUENCE: 129

Gly Arg Thr Phe Tyr Gly Asp Tyr
1 5

<210> SEQ ID NO 130
<211> LENGTH: 8
<212> TYPE: PRT
<213> ORGANISM: Artificial sequence
<220> FEATURE:
<223> OTHER INFORMATION: CDR

<400> SEQUENCE: 130

Ile Ala Val Arg Gly Arg Gly Thr
1 5

<210> SEQ ID NO 131
<211> LENGTH: 22
<212> TYPE: PRT
<213> ORGANISM: Artificial sequence
<220> FEATURE:
<223> OTHER INFORMATION: CDR

<400> SEQUENCE: 131

Ala Ala Asp Ala Gly Ser Tyr Ala Ser Arg Gly Phe Pro Val Arg Glu
1 5 10 15

Thr Gly Arg Tyr Asp Tyr
20

<210> SEQ ID NO 132
<211> LENGTH: 5
<212> TYPE: PRT
<213> ORGANISM: Artificial sequence
<220> FEATURE:
<223> OTHER INFORMATION: CDR

<400> SEQUENCE: 132

Gly Asp Tyr Ile Ala
1 5

<210> SEQ ID NO 133
<211> LENGTH: 17
<212> TYPE: PRT
<213> ORGANISM: Artificial sequence
<220> FEATURE:
<223> OTHER INFORMATION: CDR

<400> SEQUENCE: 133

Ala Ile Ala Val Arg Gly Arg Gly Thr Phe Tyr Gly Asp Ser Val Lys
1 5 10 15

Gly

<210> SEQ ID NO 134
<211> LENGTH: 20
<212> TYPE: PRT
<213> ORGANISM: Artificial sequence
<220> FEATURE:
<223> OTHER INFORMATION: CDR

<400> SEQUENCE: 134

Asp Ala Gly Ser Tyr Ala Ser Arg Gly Phe Pro Val Arg Glu Thr Gly
1 5 10 15

Arg Tyr Asp Tyr
20

<210> SEQ ID NO 135
<211> LENGTH: 7
<212> TYPE: PRT
<213> ORGANISM: Artificial sequence
<220> FEATURE:
<223> OTHER INFORMATION: CDR

<400> SEQUENCE: 135

Gly Arg Thr Phe Tyr Gly Asp
1 5

<210> SEQ ID NO 136
<211> LENGTH: 6

<212> TYPE: PRT
<213> ORGANISM: Artificial sequence
<220> FEATURE:
<223> OTHER INFORMATION: CDR

<400> SEQUENCE: 136

Ala Val Arg Gly Arg Gly
1               5

<210> SEQ ID NO 137
<211> LENGTH: 20
<212> TYPE: PRT
<213> ORGANISM: Artificial sequence
<220> FEATURE:
<223> OTHER INFORMATION: CDR

<400> SEQUENCE: 137

Asp Ala Gly Ser Tyr Ala Ser Arg Gly Phe Pro Val Arg Glu Thr Gly
1               5                   10                  15

Arg Tyr Asp Tyr
            20

<210> SEQ ID NO 138
<211> LENGTH: 8
<212> TYPE: PRT
<213> ORGANISM: Artificial sequence
<220> FEATURE:
<223> OTHER INFORMATION: CDR

<400> SEQUENCE: 138

Gly Arg Thr Leu Ser Thr Ser Thr
1               5

<210> SEQ ID NO 139
<211> LENGTH: 8
<212> TYPE: PRT
<213> ORGANISM: Artificial sequence
<220> FEATURE:
<223> OTHER INFORMATION: CDR

<400> SEQUENCE: 139

Ile Arg Trp Ser Gly Gly Met Gly
1               5

<210> SEQ ID NO 140
<211> LENGTH: 20
<212> TYPE: PRT
<213> ORGANISM: Artificial sequence
<220> FEATURE:
<223> OTHER INFORMATION: CDR

<400> SEQUENCE: 140

Ala Val Ser Thr Val Pro Tyr Tyr Gly Ser Ile Tyr Thr Arg Val Gly
1               5                   10                  15

Asp Tyr Pro Tyr
            20

<210> SEQ ID NO 141
<211> LENGTH: 5
<212> TYPE: PRT
<213> ORGANISM: Artificial sequence
<220> FEATURE:
<223> OTHER INFORMATION: CDR

<400> SEQUENCE: 141

Thr Ser Thr Ile Ala 1 5

<210> SEQ ID NO 142
<211> LENGTH: 17
<212> TYPE: PRT
<213> ORGANISM: Artificial sequence
<220> FEATURE:
<223> OTHER INFORMATION: CDR

<400> SEQUENCE: 142

Ala Ile Arg Trp Ser Gly Gly Met Gly Trp Tyr Ala Asp Ser Val Lys
1 5 10 15

Gly

<210> SEQ ID NO 143
<211> LENGTH: 18
<212> TYPE: PRT
<213> ORGANISM: Artificial sequence
<220> FEATURE:
<223> OTHER INFORMATION: CDR

<400> SEQUENCE: 143

Ser Thr Val Pro Tyr Tyr Gly Ser Ile Tyr Thr Arg Val Gly Asp Tyr
1 5 10 15

Pro Tyr

<210> SEQ ID NO 144
<211> LENGTH: 7
<212> TYPE: PRT
<213> ORGANISM: Artificial sequence
<220> FEATURE:
<223> OTHER INFORMATION: CDR

<400> SEQUENCE: 144

Gly Arg Thr Leu Ser Thr Ser
1 5

<210> SEQ ID NO 145
<211> LENGTH: 6
<212> TYPE: PRT
<213> ORGANISM: Artificial sequence
<220> FEATURE:
<223> OTHER INFORMATION: CDR

<400> SEQUENCE: 145

Arg Trp Ser Gly Gly Met
1 5

<210> SEQ ID NO 146
<211> LENGTH: 18
<212> TYPE: PRT
<213> ORGANISM: Artificial sequence
<220> FEATURE:
<223> OTHER INFORMATION: CDR

<400> SEQUENCE: 146

Ser Thr Val Pro Tyr Tyr Gly Ser Ile Tyr Thr Arg Val Gly Asp Tyr
1 5 10 15

Pro Tyr

<210> SEQ ID NO 147
<211> LENGTH: 8
<212> TYPE: PRT
<213> ORGANISM: Artificial sequence
<220> FEATURE:

<223> OTHER INFORMATION: CDR

<400> SEQUENCE: 147

Gly Asp Thr Val Ser Ile Tyr Tyr
1               5

<210> SEQ ID NO 148
<211> LENGTH: 8
<212> TYPE: PRT
<213> ORGANISM: Artificial sequence
<220> FEATURE:
<223> OTHER INFORMATION: CDR

<400> SEQUENCE: 148

Leu Ser Ala Ser Gly Gln Phe Thr
1               5

<210> SEQ ID NO 149
<211> LENGTH: 18
<212> TYPE: PRT
<213> ORGANISM: Artificial sequence
<220> FEATURE:
<223> OTHER INFORMATION: CDR

<400> SEQUENCE: 149

Ala Val Gln Arg Tyr Gly Trp Val Tyr Arg Thr Asp Lys Thr Met Tyr
1               5                   10                  15

Asn Tyr

<210> SEQ ID NO 150
<211> LENGTH: 5
<212> TYPE: PRT
<213> ORGANISM: Artificial sequence
<220> FEATURE:
<223> OTHER INFORMATION: CDR

<400> SEQUENCE: 150

Ile Tyr Tyr Met Gly
1               5

<210> SEQ ID NO 151
<211> LENGTH: 17
<212> TYPE: PRT
<213> ORGANISM: Artificial sequence
<220> FEATURE:
<223> OTHER INFORMATION: CDR

<400> SEQUENCE: 151

Ala Leu Ser Ala Ser Gly Gln Phe Thr Asp His Ala Asp Ser Val Lys
1               5                   10                  15

Gly

<210> SEQ ID NO 152
<211> LENGTH: 16
<212> TYPE: PRT
<213> ORGANISM: Artificial sequence
<220> FEATURE:
<223> OTHER INFORMATION: CDR

<400> SEQUENCE: 152

Gln Arg Tyr Gly Trp Val Tyr Arg Thr Asp Lys Thr Met Tyr Asn Tyr
1               5                   10                  15

<210> SEQ ID NO 153
<211> LENGTH: 7

<212> TYPE: PRT
<213> ORGANISM: Artificial sequence
<220> FEATURE:
<223> OTHER INFORMATION: CDR

<400> SEQUENCE: 153

Gly Asp Thr Val Ser Ile Tyr
1               5

<210> SEQ ID NO 154
<211> LENGTH: 6
<212> TYPE: PRT
<213> ORGANISM: Artificial sequence
<220> FEATURE:
<223> OTHER INFORMATION: CDR

<400> SEQUENCE: 154

Ser Ala Ser Gly Gln Phe
1               5

<210> SEQ ID NO 155
<211> LENGTH: 16
<212> TYPE: PRT
<213> ORGANISM: Artificial sequence
<220> FEATURE:
<223> OTHER INFORMATION: CDR

<400> SEQUENCE: 155

Gln Arg Tyr Gly Trp Val Tyr Arg Thr Asp Lys Thr Met Tyr Asn Tyr
1               5                   10                  15

<210> SEQ ID NO 156
<211> LENGTH: 8
<212> TYPE: PRT
<213> ORGANISM: Artificial sequence
<220> FEATURE:
<223> OTHER INFORMATION: CDR

<400> SEQUENCE: 156

Gly Phe Thr Phe Ser Asp Tyr Thr
1               5

<210> SEQ ID NO 157
<211> LENGTH: 8
<212> TYPE: PRT
<213> ORGANISM: Artificial sequence
<220> FEATURE:
<223> OTHER INFORMATION: CDR

<400> SEQUENCE: 157

Ile Ser Ser Gly Gly His Phe Lys
1               5

<210> SEQ ID NO 158
<211> LENGTH: 19
<212> TYPE: PRT
<213> ORGANISM: Artificial sequence
<220> FEATURE:
<223> OTHER INFORMATION: CDR

<400> SEQUENCE: 158

Ala Lys Cys Pro Arg Pro Ser Val Tyr Cys Arg Asp Tyr Glu Ser Thr
1               5                   10                  15

Ser Leu Tyr

<210> SEQ ID NO 159

<211> LENGTH: 5
<212> TYPE: PRT
<213> ORGANISM: Artificial sequence
<220> FEATURE:
<223> OTHER INFORMATION: CDR

<400> SEQUENCE: 159

Asp Tyr Thr Met Asn
1               5

<210> SEQ ID NO 160
<211> LENGTH: 17
<212> TYPE: PRT
<213> ORGANISM: Artificial sequence
<220> FEATURE:
<223> OTHER INFORMATION: CDR

<400> SEQUENCE: 160

Glu Ile Ser Ser Gly Gly His Phe Lys Ser Asn Ala Asp Ser Val Lys
1               5                   10                  15

Asp

<210> SEQ ID NO 161
<211> LENGTH: 17
<212> TYPE: PRT
<213> ORGANISM: Artificial sequence
<220> FEATURE:
<223> OTHER INFORMATION: CDR

<400> SEQUENCE: 161

Cys Pro Arg Pro Ser Val Tyr Cys Arg Asp Tyr Glu Ser Thr Ser Leu
1               5                   10                  15

Tyr

<210> SEQ ID NO 162
<211> LENGTH: 7
<212> TYPE: PRT
<213> ORGANISM: Artificial sequence
<220> FEATURE:
<223> OTHER INFORMATION: CDR

<400> SEQUENCE: 162

Gly Phe Thr Phe Ser Asp Tyr
1               5

<210> SEQ ID NO 163
<211> LENGTH: 6
<212> TYPE: PRT
<213> ORGANISM: Artificial sequence
<220> FEATURE:
<223> OTHER INFORMATION: CDR

<400> SEQUENCE: 163

Ser Ser Gly Gly His Phe
1               5

<210> SEQ ID NO 164
<211> LENGTH: 17
<212> TYPE: PRT
<213> ORGANISM: Artificial sequence
<220> FEATURE:
<223> OTHER INFORMATION: CDR

<400> SEQUENCE: 164

Cys Pro Arg Pro Ser Val Tyr Cys Arg Asp Tyr Glu Ser Thr Ser Leu
1               5                   10                  15

Tyr

<210> SEQ ID NO 165
<211> LENGTH: 8
<212> TYPE: PRT
<213> ORGANISM: Artificial sequence
<220> FEATURE:
<223> OTHER INFORMATION: CDR

<400> SEQUENCE: 165

Gly Phe Asp Phe Ser Phe Tyr Thr
1 5

<210> SEQ ID NO 166
<211> LENGTH: 8
<212> TYPE: PRT
<213> ORGANISM: Artificial sequence
<220> FEATURE:
<223> OTHER INFORMATION: CDR

<400> SEQUENCE: 166

Ile Ser Thr Gly Gly Gly Gly Ser
1 5

<210> SEQ ID NO 167
<211> LENGTH: 19
<212> TYPE: PRT
<213> ORGANISM: Artificial sequence
<220> FEATURE:
<223> OTHER INFORMATION: CDR

<400> SEQUENCE: 167

Ala Ser His Arg Arg Gly Tyr Met Phe Val Ser Ser Arg Lys Asn Glu
1 5 10 15

Tyr Asp Tyr

<210> SEQ ID NO 168
<211> LENGTH: 5
<212> TYPE: PRT
<213> ORGANISM: Artificial sequence
<220> FEATURE:
<223> OTHER INFORMATION: CDR

<400> SEQUENCE: 168

Phe Tyr Thr Met Thr
1 5

<210> SEQ ID NO 169
<211> LENGTH: 17
<212> TYPE: PRT
<213> ORGANISM: Artificial sequence
<220> FEATURE:
<223> OTHER INFORMATION: CDR

<400> SEQUENCE: 169

Thr Ile Ser Thr Gly Gly Gly Gly Ser Asn Tyr Ala Asp Ser Val Lys
1 5 10 15

Gly

<210> SEQ ID NO 170
<211> LENGTH: 17
<212> TYPE: PRT
<213> ORGANISM: Artificial sequence
<220> FEATURE:
<223> OTHER INFORMATION: CDR

<400> SEQUENCE: 170

His Arg Arg Gly Tyr Met Phe Val Ser Ser Arg Lys Asn Glu Tyr Asp
1 5 10 15

Tyr

<210> SEQ ID NO 171
<211> LENGTH: 7
<212> TYPE: PRT
<213> ORGANISM: Artificial sequence
<220> FEATURE:
<223> OTHER INFORMATION: CDR

<400> SEQUENCE: 171

Gly Phe Asp Phe Ser Phe Tyr
1 5

<210> SEQ ID NO 172
<211> LENGTH: 6
<212> TYPE: PRT
<213> ORGANISM: Artificial sequence
<220> FEATURE:
<223> OTHER INFORMATION: CDR

<400> SEQUENCE: 172

Ser Thr Gly Gly Gly Gly
1 5

<210> SEQ ID NO 173
<211> LENGTH: 17
<212> TYPE: PRT
<213> ORGANISM: Artificial sequence
<220> FEATURE:
<223> OTHER INFORMATION: CDR

<400> SEQUENCE: 173

His Arg Arg Gly Tyr Met Phe Val Ser Ser Arg Lys Asn Glu Tyr Asp
1 5 10 15

Tyr

<210> SEQ ID NO 174
<211> LENGTH: 8
<212> TYPE: PRT
<213> ORGANISM: Artificial sequence
<220> FEATURE:
<223> OTHER INFORMATION: CDR

<400> SEQUENCE: 174

Gly Arg Ala Ser Gly Ser Gly Ala
1 5

<210> SEQ ID NO 175
<211> LENGTH: 8
<212> TYPE: PRT
<213> ORGANISM: Artificial sequence
<220> FEATURE:
<223> OTHER INFORMATION: CDR

<400> SEQUENCE: 175

Ile Glu Trp Ser Ser Gly Gly Pro
1 5

<210> SEQ ID NO 176
<211> LENGTH: 15
<212> TYPE: PRT

<213> ORGANISM: Artificial sequence
<220> FEATURE:
<223> OTHER INFORMATION: CDR

<400> SEQUENCE: 176

Ala Ala Ala Pro Trp Val Phe Ser Ser Pro Asp Asp Tyr Met Tyr
1 5 10 15

<210> SEQ ID NO 177
<211> LENGTH: 5
<212> TYPE: PRT
<213> ORGANISM: Artificial sequence
<220> FEATURE:
<223> OTHER INFORMATION: CDR

<400> SEQUENCE: 177

Ser Gly Ala Met Gly
1 5

<210> SEQ ID NO 178
<211> LENGTH: 17
<212> TYPE: PRT
<213> ORGANISM: Artificial sequence
<220> FEATURE:
<223> OTHER INFORMATION: CDR

<400> SEQUENCE: 178

Gly Ile Glu Trp Ser Ser Gly Gly Pro Val Tyr Ala Asp Ser Val Lys
1 5 10 15

Gly

<210> SEQ ID NO 179
<211> LENGTH: 13
<212> TYPE: PRT
<213> ORGANISM: Artificial sequence
<220> FEATURE:
<223> OTHER INFORMATION: CDR

<400> SEQUENCE: 179

Ala Pro Trp Val Phe Ser Ser Pro Asp Asp Tyr Met Tyr
1 5 10

<210> SEQ ID NO 180
<211> LENGTH: 7
<212> TYPE: PRT
<213> ORGANISM: Artificial sequence
<220> FEATURE:
<223> OTHER INFORMATION: CDR

<400> SEQUENCE: 180

Gly Arg Ala Ser Gly Ser Gly
1 5

<210> SEQ ID NO 181
<211> LENGTH: 6
<212> TYPE: PRT
<213> ORGANISM: Artificial sequence
<220> FEATURE:
<223> OTHER INFORMATION: CDR

<400> SEQUENCE: 181

Glu Trp Ser Ser Gly Gly
1 5

<210> SEQ ID NO 182
<211> LENGTH: 13

<212> TYPE: PRT
<213> ORGANISM: Artificial sequence
<220> FEATURE:
<223> OTHER INFORMATION: CDR

<400> SEQUENCE: 182

Ala Pro Trp Val Phe Ser Ser Pro Asp Asp Tyr Met Tyr
1 5 10

<210> SEQ ID NO 183
<211> LENGTH: 8
<212> TYPE: PRT
<213> ORGANISM: Artificial sequence
<220> FEATURE:
<223> OTHER INFORMATION: CDR

<400> SEQUENCE: 183

Gly Leu Thr Phe Ser Tyr Tyr Gly
1 5

<210> SEQ ID NO 184
<211> LENGTH: 8
<212> TYPE: PRT
<213> ORGANISM: Artificial sequence
<220> FEATURE:
<223> OTHER INFORMATION: CDR

<400> SEQUENCE: 184

Ile Asn Trp Ser Gly Thr Ser Thr
1 5

<210> SEQ ID NO 185
<211> LENGTH: 19
<212> TYPE: PRT
<213> ORGANISM: Artificial sequence
<220> FEATURE:
<223> OTHER INFORMATION: CDR

<400> SEQUENCE: 185

Ala Ala Arg Lys Tyr Ser Ser Ser Gln Ala Met Gly Leu Pro Asn Asp
1 5 10 15

Ile Asp Tyr

<210> SEQ ID NO 186
<211> LENGTH: 5
<212> TYPE: PRT
<213> ORGANISM: Artificial sequence
<220> FEATURE:
<223> OTHER INFORMATION: CDR

<400> SEQUENCE: 186

Tyr Tyr Gly Met Gly
1 5

<210> SEQ ID NO 187
<211> LENGTH: 17
<212> TYPE: PRT
<213> ORGANISM: Artificial sequence
<220> FEATURE:
<223> OTHER INFORMATION: CDR

<400> SEQUENCE: 187

Ala Ile Asn Trp Ser Gly Thr Ser Thr Tyr Tyr Ala Asp Ser Val Lys
1 5 10 15

Asp

<210> SEQ ID NO 188
<211> LENGTH: 17
<212> TYPE: PRT
<213> ORGANISM: Artificial sequence
<220> FEATURE:
<223> OTHER INFORMATION: CDR

<400> SEQUENCE: 188

Arg Lys Tyr Ser Ser Ser Gln Ala Met Gly Leu Pro Asn Asp Ile Asp
1               5                   10                  15

Tyr

<210> SEQ ID NO 189
<211> LENGTH: 7
<212> TYPE: PRT
<213> ORGANISM: Artificial sequence
<220> FEATURE:
<223> OTHER INFORMATION: CDR

<400> SEQUENCE: 189

Gly Leu Thr Phe Ser Tyr Tyr
1               5

<210> SEQ ID NO 190
<211> LENGTH: 6
<212> TYPE: PRT
<213> ORGANISM: Artificial sequence
<220> FEATURE:
<223> OTHER INFORMATION: CDR

<400> SEQUENCE: 190

Asn Trp Ser Gly Thr Ser
1               5

<210> SEQ ID NO 191
<211> LENGTH: 17
<212> TYPE: PRT
<213> ORGANISM: Artificial sequence
<220> FEATURE:
<223> OTHER INFORMATION: CDR

<400> SEQUENCE: 191

Arg Lys Tyr Ser Ser Ser Gln Ala Met Gly Leu Pro Asn Asp Ile Asp
1               5                   10                  15

Tyr

<210> SEQ ID NO 192
<211> LENGTH: 8
<212> TYPE: PRT
<213> ORGANISM: Artificial sequence
<220> FEATURE:
<223> OTHER INFORMATION: CDR

<400> SEQUENCE: 192

Thr Arg Ile Phe Arg Ser Tyr Val
1               5

<210> SEQ ID NO 193
<211> LENGTH: 8
<212> TYPE: PRT
<213> ORGANISM: Artificial sequence
<220> FEATURE:
<223> OTHER INFORMATION: CDR

<400> SEQUENCE: 193

Ile Arg Trp Ser Asn Asp Thr Gly
1 5

<210> SEQ ID NO 194
<211> LENGTH: 17
<212> TYPE: PRT
<213> ORGANISM: Artificial sequence
<220> FEATURE:
<223> OTHER INFORMATION: CDR

<400> SEQUENCE: 194

Ala Ala Asp Ser Pro Pro Trp Gly Arg Thr Trp Tyr Thr Gly Tyr Asp
1 5 10 15

Tyr

<210> SEQ ID NO 195
<211> LENGTH: 5
<212> TYPE: PRT
<213> ORGANISM: Artificial sequence
<220> FEATURE:
<223> OTHER INFORMATION: CDR

<400> SEQUENCE: 195

Ser Tyr Val Met Gly
1 5

<210> SEQ ID NO 196
<211> LENGTH: 17
<212> TYPE: PRT
<213> ORGANISM: Artificial sequence
<220> FEATURE:
<223> OTHER INFORMATION: CDR

<400> SEQUENCE: 196

Ser Ile Arg Trp Ser Asn Asp Thr Gly Thr Tyr Ala Asp Ser Val Lys
1 5 10 15

Gly

<210> SEQ ID NO 197
<211> LENGTH: 15
<212> TYPE: PRT
<213> ORGANISM: Artificial sequence
<220> FEATURE:
<223> OTHER INFORMATION: CDR

<400> SEQUENCE: 197

Asp Ser Pro Pro Trp Gly Arg Thr Trp Tyr Thr Gly Tyr Asp Tyr
1 5 10 15

<210> SEQ ID NO 198
<211> LENGTH: 7
<212> TYPE: PRT
<213> ORGANISM: Artificial sequence
<220> FEATURE:
<223> OTHER INFORMATION: CDR

<400> SEQUENCE: 198

Thr Arg Ile Phe Arg Ser Tyr
1 5

<210> SEQ ID NO 199
<211> LENGTH: 6
<212> TYPE: PRT
<213> ORGANISM: Artificial sequence
<220> FEATURE:
<223> OTHER INFORMATION: CDR

<400> SEQUENCE: 199

Arg Trp Ser Asn Asp Thr
1 5

<210> SEQ ID NO 200
<211> LENGTH: 15
<212> TYPE: PRT
<213> ORGANISM: Artificial sequence
<220> FEATURE:
<223> OTHER INFORMATION: CDR

<400> SEQUENCE: 200

Asp Ser Pro Pro Trp Gly Arg Thr Trp Tyr Thr Gly Tyr Asp Tyr
1 5 10 15

<210> SEQ ID NO 201
<211> LENGTH: 8
<212> TYPE: PRT
<213> ORGANISM: Artificial sequence
<220> FEATURE:
<223> OTHER INFORMATION: CDR

<400> SEQUENCE: 201

Gly Arg Pro Phe Asp Trp Leu Thr
1 5

<210> SEQ ID NO 202
<211> LENGTH: 8
<212> TYPE: PRT
<213> ORGANISM: Artificial sequence
<220> FEATURE:
<223> OTHER INFORMATION: CDR

<400> SEQUENCE: 202

Ile Ser Gln Ser Gly Gly Arg Ile
1 5

<210> SEQ ID NO 203
<211> LENGTH: 18
<212> TYPE: PRT
<213> ORGANISM: Artificial sequence
<220> FEATURE:
<223> OTHER INFORMATION: CDR

<400> SEQUENCE: 203

Ala Ala Gln Met Arg Gly Tyr Ser Arg Ala Ala Tyr Pro Asp Glu Tyr
1 5 10 15

Asp Tyr

<210> SEQ ID NO 204
<211> LENGTH: 5
<212> TYPE: PRT
<213> ORGANISM: Artificial sequence
<220> FEATURE:
<223> OTHER INFORMATION: CDR

<400> SEQUENCE: 204

Trp Leu Thr Val Gly
1 5

<210> SEQ ID NO 205
<211> LENGTH: 17
<212> TYPE: PRT
<213> ORGANISM: Artificial sequence
<220> FEATURE:

<223> OTHER INFORMATION: CDR

<400> SEQUENCE: 205

Ala Ile Ser Gln Ser Gly Gly Arg Ile Phe Tyr Ser Asp Ser Val Lys
1 5 10 15

Gly

<210> SEQ ID NO 206
<211> LENGTH: 16
<212> TYPE: PRT
<213> ORGANISM: Artificial sequence
<220> FEATURE:
<223> OTHER INFORMATION: CDR

<400> SEQUENCE: 206

Gln Met Arg Gly Tyr Ser Arg Ala Ala Tyr Pro Asp Glu Tyr Asp Tyr
1 5 10 15

<210> SEQ ID NO 207
<211> LENGTH: 7
<212> TYPE: PRT
<213> ORGANISM: Artificial sequence
<220> FEATURE:
<223> OTHER INFORMATION: CDR

<400> SEQUENCE: 207

Gly Arg Pro Phe Asp Trp Leu
1 5

<210> SEQ ID NO 208
<211> LENGTH: 6
<212> TYPE: PRT
<213> ORGANISM: Artificial sequence
<220> FEATURE:
<223> OTHER INFORMATION: CDR

<400> SEQUENCE: 208

Ser Gln Ser Gly Gly Arg
1 5

<210> SEQ ID NO 209
<211> LENGTH: 16
<212> TYPE: PRT
<213> ORGANISM: Artificial sequence
<220> FEATURE:
<223> OTHER INFORMATION: CDR

<400> SEQUENCE: 209

Gln Met Arg Gly Tyr Ser Arg Ala Ala Tyr Pro Asp Glu Tyr Asp Tyr
1 5 10 15

<210> SEQ ID NO 210
<211> LENGTH: 8
<212> TYPE: PRT
<213> ORGANISM: Artificial sequence
<220> FEATURE:
<223> OTHER INFORMATION: CDR

<400> SEQUENCE: 210

Gly Arg Thr Ala Thr Ile Ser Thr
1 5

<210> SEQ ID NO 211
<211> LENGTH: 8
<212> TYPE: PRT
<213> ORGANISM: Artificial sequence

<220> FEATURE:
<223> OTHER INFORMATION: CDR

<400> SEQUENCE: 211

Ile Asp Trp Ser Ala Glu Ser Thr
1 5

<210> SEQ ID NO 212
<211> LENGTH: 12
<212> TYPE: PRT
<213> ORGANISM: Artificial sequence
<220> FEATURE:
<223> OTHER INFORMATION: CDR

<400> SEQUENCE: 212

Ala Ala Ile Val Val Arg Glu Arg Ser Tyr Lys Tyr
1 5 10

<210> SEQ ID NO 213
<211> LENGTH: 5
<212> TYPE: PRT
<213> ORGANISM: Artificial sequence
<220> FEATURE:
<223> OTHER INFORMATION: CDR

<400> SEQUENCE: 213

Ile Ser Thr Met Gly
1 5

<210> SEQ ID NO 214
<211> LENGTH: 17
<212> TYPE: PRT
<213> ORGANISM: Artificial sequence
<220> FEATURE:
<223> OTHER INFORMATION: CDR

<400> SEQUENCE: 214

Arg Ile Asp Trp Ser Ala Glu Ser Thr Tyr Ile Val Asp Ser Val Lys
1 5 10 15

Gly

<210> SEQ ID NO 215
<211> LENGTH: 10
<212> TYPE: PRT
<213> ORGANISM: Artificial sequence
<220> FEATURE:
<223> OTHER INFORMATION: CDR

<400> SEQUENCE: 215

Ile Val Val Arg Glu Arg Ser Tyr Lys Tyr
1 5 10

<210> SEQ ID NO 216
<211> LENGTH: 7
<212> TYPE: PRT
<213> ORGANISM: Artificial sequence
<220> FEATURE:
<223> OTHER INFORMATION: CDR

<400> SEQUENCE: 216

Gly Arg Thr Ala Thr Ile Ser
1 5

<210> SEQ ID NO 217
<211> LENGTH: 6
<212> TYPE: PRT

-continued

```
<213> ORGANISM: Artificial sequence
<220> FEATURE:
<223> OTHER INFORMATION: CDR

<400> SEQUENCE: 217

Asp Trp Ser Ala Glu Ser
1               5


<210> SEQ ID NO 218
<211> LENGTH: 10
<212> TYPE: PRT
<213> ORGANISM: Artificial sequence
<220> FEATURE:
<223> OTHER INFORMATION: CDR

<400> SEQUENCE: 218

Ile Val Val Arg Glu Arg Ser Tyr Lys Tyr
1               5                   10
```